United States Patent
Kajihara et al.

(10) Patent No.: US 8,765,669 B2
(45) Date of Patent: Jul. 1, 2014

(54) GLYCOSYLATED GLP-1 PEPTIDE

(75) Inventors: Yasuhiro Kajihara, Toyonaka (JP); Takashi Tsuji, Nagareyama (JP); Izumi Sakamoto, Tokushima (JP); Yuri Nambu, Tokushima (JP); Naohiro Hayashi, Tokushima (JP); Kazuyuki Ishii, Tokushima (JP); Kazuhiro Fukae, Tokushima (JP); Katsunari Tezuka, Tokushima (JP); Hiroaki Asai, Tokushima (JP)

(73) Assignee: Glytech, Inc., Kyoto (JP)

( * ) Notice: Subject to any disclaimer, the term of this patent is extended or adjusted under 35 U.S.C. 154(b) by 514 days.

(21) Appl. No.: 12/999,654

(22) PCT Filed: Jun. 15, 2009

(86) PCT No.: PCT/JP2009/002709
§ 371 (c)(1),
(2), (4) Date: Mar. 2, 2011

(87) PCT Pub. No.: WO2009/153960
PCT Pub. Date: Dec. 23, 2009

(65) Prior Publication Data
US 2011/0195897 A1    Aug. 11, 2011

(30) Foreign Application Priority Data
Jun. 17, 2008  (JP) ................. 2008-157583
Dec. 22, 2008  (JP) ................. 2008-326609

(51) Int. Cl.
| A61K 38/26 | (2006.01) |
| A61P 3/10 | (2006.01) |
| A61P 7/12 | (2006.01) |
| C07K 14/605 | (2006.01) |
| C07K 1/00 | (2006.01) |
| C07K 14/00 | (2006.01) |
| C07K 17/00 | (2006.01) |

(52) U.S. Cl.
USPC ................. 514/7.2; 514/11.7; 530/395

(58) Field of Classification Search
CPC .................... A61K 38/00; C07K 14/0605
See application file for complete search history.

(56) References Cited

U.S. PATENT DOCUMENTS

| 7,985,731 B2* | 7/2011 | Kajihara et al. ............... 514/7.2 |
| 2004/0181054 A1 | 9/2004 | Kajihara et al. |
| 2008/0044411 A1 | 2/2008 | O'Neil et al. |
| 2008/0146494 A1* | 6/2008 | DeFrees et al. ................ 514/8 |
| 2008/0242607 A1 | 10/2008 | DeFrees |
| 2008/0248959 A1 | 10/2008 | DeFrees |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2009/0082266 A1 | 3/2009 | Nakamura et al. |
| 2009/0111739 A1 | 4/2009 | Kajihara et al. |
| 2010/0016547 A1* | 1/2010 | Ito et al. .................... 530/324 |

FOREIGN PATENT DOCUMENTS

| EP | 1771066 A2 | 4/2007 |
| EP | 1857467 A1 | 11/2007 |
| EP | 1961764 A1 | 8/2008 |
| EP | 2049144 A2 | 4/2009 |
| EP | 2049567 A2 | 4/2009 |
| EP | 2172479 A1 | 4/2010 |
| WO | 2005/087797 A1 | 9/2005 |
| WO | 2006/010143 A2 | 1/2006 |
| WO | 2006/082184 A2 | 8/2006 |
| WO | 2006/095775 A1 | 9/2006 |
| WO | 2007/063907 A1 | 6/2007 |
| WO | 2008/011446 A2 | 1/2008 |
| WO | 2008/011633 A2 | 1/2008 |
| WO | 2008/155900 A1 | 12/2008 |

OTHER PUBLICATIONS

Meurer, Janet A., et al., "Properties of Native and In Vitro Glycosylated Forms of the Glucagon-Like Peptide-1 Receptor Antagonist Exendin(9-39)"; Metabolism, vol. 48, No. 6 (Jun. 1999); pp. 716-724.
Sinclaire, Angus M., et al., "Glycoengineering: The Effect of Glycosylation on the Properties of Therapeutic Proteins"; Journal of Pharmaceutical Sciences, vol. 94, No. 8, Aug. 2005; pp. 1626-1635.
Ueda, Taichi, et al., "Chemoenzymatic Synthesis of Glycosylated Glucagon-like Peptide 1: Effect of Glycosylation on Proteolytic Resistance and in Vivo Blood Glucose-Lowering Activity"; Journal of the American Chemical Society, 2009, 131, pp. 6237-5245.
Ueda, Taichi, et al., "Improved Proteolytic Stability and Blood Glucose-lowering Activity of Glycosylated Glucagon-like Peptide 1"; Peptide Science 2008: M. Nomiza (Ed.), The Japanese Peptide Society (2009); pp. 293-296.
Ceaglio, N., et al., "Novel long-lasting interferon alpha derivatives designed by glycoengineering"; The Japanese Peptide Society, Peptide Science 2008; Elsevier.com; ScienceDirect, www.sciencedirect.com; Biochimie 90 (2008); pp. 437-449.

(Continued)

Primary Examiner — Marcela M Cordero Garcia
(74) Attorney, Agent, or Firm — Osha Liang LLP

(57) ABSTRACT

Oligosaccharide chain added GLP-1 peptides are more stable in blood and more active in controlling blood-sugar levels than GLP-1 peptides without added oligosaccharides. Oligosaccharide chain added GLP-1 peptides having GLP-1 activity include at least one or at least two amino acids each substituted with an oligosaccharide chain added amino acid in GLP-1; a peptide having the amino acid sequence of GLP-1 with deletion, substitution or addition of one or several amino acids; or a GLP-1 analog. Oligosaccharide chain added GLP-1 peptides with at least one amino acid substituted with an oligosaccharide chain added amino acid include an oligosaccharide chain with oligo hyaluronic acid. Oligosaccharide chain added amino acids include oligosaccharide chains attached to amino acids via linkers.

15 Claims, 3 Drawing Sheets

(56) References Cited

OTHER PUBLICATIONS

Bendele, Alison, et al., "Short Communication: Renal Tubular Vacuolation in Animals Treated with Polyethylene-Glycol-Conjugated Proteins"; Toxicological Sciences 42, Article No. TX972396, (1998); pp. 152-157.

Eng, John, et al., "Isolation and Characterization of Exendin-4, an Exendin-3 Analogue, from *Heloderma suspectum* Venom (Further Evidence For An Exendin Receptor On Dispersed Acini From Guinea Pig Pancreas)"; The Journal of Biological Chemistry, vol. 267, No. 11, Issue of Apr. 15, 1992; pp. 7402-7406.

Schnabel, Catherine A., et al., "Metabolic effects of the incretin mimetic exenatide in the treatment of type 2 diabetes"; Vascular Health and Risk Management 2006:2(1), 2006 Dove Medical Press Limited; pp. 69-77.

Amori, MD, Renee E., et al., "Efficacy and Safety of Incretin Therapy in Type 2 Diabetes (Systematic Review and Meta-analysis)"; Journal of the American Medical Association, vol. 298, No. 2 (reprinted), Jul. 11, 2007; pp. 194-206.

Wajchenberg, Bernardo L., "b-Cell Failure in Diabetes and Preservation by Clinical Treatment"; Endocrine Reviews, The Endocrine Socitey, 2007 28: pp. 187-218 (originally published online Mar. 12, 2007; doi: 10.1210/10.1210/er.2006-0038, http://edrv.endojournals.org//subscriptions/).

International Search Report dated Sep. 8, 2009, issued in related International Application No. PCT/JP2009/002709, with English translation (9 pages) [NOTE: All non-patent literature documents referenced in this ISR were previously submitted to the USPTO in the IDS filed Mar. 2, 2011.].

Extended European Search Report dated Jul. 4, 2011, issued by the European Patent Office in related European Patent Application No. 09766408.0 (7 pages).

Young, Andrew A., et al., "Glucose-Lowering and Insulin-Sensitizing Actions of Exendin-4 Studies in Obese Diabetic (ob/ob, db/db) Mice, Diabetic Fatty Zuker Rats, and diabetic Rhesus Monkeys (*Macaca mulatta*)"; Diabetes, vol. 48, American Diabetes Association, May 1, 1999; XP-000971924, ISSN: 0012-1797, DOI: 10.2337/Diabetes.48.5.1026; pp. 1026-1034.

Biochemistry: Textbook; For Universities, Ed. Severin E.S., 2003, 779 p.; pp. 34-35 and 39-40.

Office Action, with English translation, issued Feb. 8, 2013, by the Russian Patent Office in related Russian Patent Application No. 2011101464. (11 pages)

Official Action dated Jun. 10, 2013, issued by the Russian Patent Office in related Russian Patent Application No. 2011101464/10(001825), with an English translation (10 pages).

First Official Action dated Nov. 26, 2013, issued by the Japan Patent Office in related Japanese Patent Application No. JP2010-517710 (3 pages).

Notification on results of test of invention for patentability (3rd Official Action) dated Jan. 10, 2014, issued by the Russia Patent Office in corresponding Russian Patent Application No. 2011101464, with English translation (13 pages).

Hui, Hongxiang, et al., "The short half-life of glucagon-like peptide-1 in plasma does not reflect its long-lasting beneficial effects"; The European Journal of Endocrinology (2002), No. 146; ISSN0804-4643; pp. 863-869.

Frankel, Arthur E., et al., "Characterization of diphtheria fusion proteins targeted to the human interleukin-3 receptor"; Protein Engineering, vol. 13, No. 8, (2000); pp. 575-581.

* cited by examiner

GLYCOSYLATED GLP-1 PEPTIDE

TECHNICAL FIELD

The present invention relates to an oligosaccharide chain added GLP-1 peptide.

BACKGROUND ART

GLP-1 (glucagon-like peptide-1) is a peptide of intestinal origin that is deeply involved in regulation of glucose homeostasis. GLP-1 is synthesized in intestinal L-cells by the tissue-specific post-translational processing of preproglucagon which is a glucagon precursor and released into circulation in response to food intake. This peptide serves as main mediators of the enteroinsular axis and act through the binding to particular receptors.

GLP-1 has been known to act mainly on the pancreas and promote the insulin release of β cells in a glucose concentration-dependent manner. It has also been suggested that GLP-1 is likely to suppress glucagon secretion, delay gastric emptying, and enhance peripheral glucose disposal.

The administration of GLP-1 to patients with non-insulin-dependent diabetes mellitus can normalize postprandial glucose levels, suggesting that GLP-1 may be used as a therapeutic drug. GLP-1 also has the effect of improving glycemic control in patients with insulin-dependent diabetes mellitus. Since the effect of promoting insulin release by GLP-1 depends on plasma glucose concentrations, GLP-1 mediates reduced insulin release at a low plasma glucose concentration and therefore advantageously causes no serious hypoglycemia. Thus, the highly safe treatment of diabetes can be achieved by controlling the amount of GLP-1 in blood as necessary. However, the half-life of GLP-1 in blood is as extremely short as 2 to 6 minutes, presenting the problem of its limited possibility as a therapeutic agent.

To solve such a problem, an attempt has been made to modify GLP-1. For example, Patent Document 1 discloses a PEGylated GLP-1 compound comprising a GLP-1 compound conjugated to at least 1 polyethylene glycol (PEG) molecule. In the PEGylated GLP-1 compound, each PEG is bound with the GLP-1 compound at the Cys or Lys amino acid or at the carboxyl-terminal amino acid. The PEGylated GLP-1 compound has an elimination half-life of at least 1 hour.

According to Patent Document 1, the obtained biologically active peptide has a longer half-life and highly delayed clearance compared to those of unPEGylated peptides. It has also been shown that the PEGylated GLP-1 compound and composition are useful in the treatment of the health condition such as diabetes, obesity and irritable bowel syndrome as well as reducing blood sugar level, suppressing gastric and/or intestinal motility, gastric and/or intestinal emptying, and controlling food intake (e.g., Non-patent document 1).

However, PEG is a compound that is not metabolized in vivo. Therefore, the continuous administration of the PEGylated GLP-1 compound accumulates PEG in vivo and might cause adverse reaction in the living bodies (Non-patent document 1).

Moreover, to prolong the half-life, a method for adding an oligosaccharide chain to GLP-1 or modified GLP-1 has also been proposed (e.g., Patent Documents 3 and 4). Patent Document 3 discloses a method which comprises introducing an oligosaccharide chain added amino acid to positions 26, 34 and/or 37 of GLP-1, etc. However, the type of the oligosaccharide chain and the oligosaccharide chain added sites are less than optimal. On the other hand, Patent Document 4 discloses a method which comprises binding modified hyaluronic acid having a molecular weight of about 200 KDa to a GLP-1 analog. However, when such big hyaluronic acid molecules are produced in large amounts, it is difficult to make their lengths or structures uniform. Thus, the actual hyaluronic acids may largely vary in structure or length. Oligosaccharide chain added peptides of uniform length or structure are required for pharmaceutical use.

Exendin-4 found from the saliva of a lizard (Heloderma) is a compound that is structurally similar to GLP-1 and has similar activity and high stability in blood (Non-patent Document 2) which has been placed on the market in U.S. However, exendin-4 has a nonhuman sequence and might induce neutralizing antibodies attributed to long-term administration, leading to attenuated efficacy ((Non-patent Documents 3-5).

On the other hand, it has become evident that oligosaccharide chains play various roles in vivo. They have been less well studied due to their complicated and diverse structures, though the importance of the studies is recognized. An attempt has been made on a method for obtaining a glycopeptide having constant composition (Patent Document 2). However, this production method is still less than sufficient from the viewpoint of convenience or large-scale production and is not practical method particularly for long oligosaccharide chains existing in vivo.

[Patent Document 1] National Publication of International Patent Application No. 2006-520818
[Patent Document 2] WO 2005-095331
[Non-patent document 1] Toxicological Science, 42, 152-157 (1998)
[Non-patent document 2] J Biol. Chem. 267, 7402-5 (1992)
[Non-patent Document 3] Vascular Health and Risk Management 2, 69-77 (2006)
[Non-patent Document 4] JAMA. 298, 194-206 (2007)
[Non-patent Document 5] Endocrine Reviews 28, 187-218 (2007)

SUMMARY OF THE INVENTION

Problem to be Solved by the Invention

An object of the present invention is to provide an oligosaccharide chain added GLP-1 peptide that has higher stability in blood than that of GLP-1 and, more preferably, exhibits higher activity of controlling blood-sugar levels than that of GLP-1.

Means for Solving Problem

The present invention can have the following characteristics to solve the problem.

Specifically, the present invention provides an oligosaccharide chain added GLP-1 peptide having GLP-1 activity, wherein at least two amino acid is substituted with an oligosaccharide chain added amino acid, in (a) GLP-1;
(b) a peptide having the amino acid sequence of GLP-1 with deletion, substitution or addition of one or several amino acids; or
(c) a GLP-1 analog.

The present invention also provides an oligosaccharide chain added GLP-1 peptide having GLP-1 activity, wherein at least two amino acid is substituted with an oligosaccharide chain added amino acid, in (a) GLP-1; or (b) a peptide having the amino acid sequence of GLP-1 with deletion, substitution or addition of one or several amino acids and having GLP-1 activity.

The present invention also provides an oligosaccharide chain added GLP-1 peptide having GLP-1 activity, wherein the oligosaccharide chain added GLP-1 peptide is (a) an oligosaccharide chain added GLP-1 peptide wherein at least two amino acids of GLP-1 are each substituted with an oligosaccharide chain added amino acid and at least one of the substituted sites is position 18, 20, 22, 26, 30, 34 or 36 of GLP-1; or (b) an oligosaccharide chain added GLP-1 peptide having the amino acid sequence of the oligosaccharide chain added GLP-1 peptide defined in (a) with deletion, substitution or addition of one or several amino acids except the oligosaccharide chain added amino acids.

The present invention also provides an oligosaccharide chain added GLP-1 peptide having GLP-1 activity, wherein the oligosaccharide chain added GLP-1 peptide is (a) an oligosaccharide chain added GLP-1 peptide wherein at least two amino acids of GLP-1 are each substituted with an oligosaccharide chain added amino acid and each of the substituted sites is position 18, 20, 22, 26, 30, 34 or 36 of GLP-1; or (b) an oligosaccharide chain added GLP-1 peptide having the amino acid sequence of the oligosaccharide chain added GLP-1 peptide defined in (a) with deletion, substitution or addition of one or several amino acids except the oligosaccharide chain added amino acids.

In the present invention, the oligosaccharide chain added amino acid can be preferably, but not limited to, oligosaccharide chain added Asn or oligosaccharide chain added Cys, depending on embodiments.

In the present invention, the oligosaccharide chain added amino acids linked to the oligosaccharide chain added GLP-1 peptide may be the same or different in the type of the oligosaccharide chain or the amino acid.

In the present invention, in the oligosaccharide chain added amino acid, the oligosaccharide chain may be linked to the amino acid via a linker or without a linker. Preferably, the oligosaccharide chain is linked to the amino acid without a linker (i.e., directly), depending on embodiments.

In the present invention, the oligosaccharide chain is generally preferably an oligosaccharide chain consisting of four or more sugars. However, an oligosaccharide chain consisting of five to eleven sugars may be preferable, depending on embodiments.

In the present invention, the oligosaccharide chain may be preferably, but not limited to, biantennary complex-type oligosaccharide chain, depending on embodiments. The oligosaccharide chain may be preferably, but not limited to, an oligosaccharide chain selected from the group consisting of disialo, monosialo, asialo, diGlcNAc and dimannose oligosaccharide chains, depending on embodiments.

In the present invention, the oligosaccharide chain may be preferably, but not limited to, an oligosaccharide chain represented by the following formula, depending on embodiments:

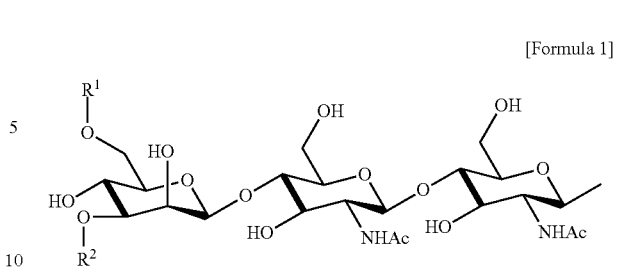

[Formula 1]

wherein $R^1$ and $R^2$ are the same or different and each represents

[Formula 2]

and

Ac represents an acetyl group.

The present invention also provides an oligosaccharide chain added GLP-1 peptide wherein at least one amino acid of the parent peptide is substituted with an oligosaccharide chain added amino acid and the oligosaccharide chain is oligo hyaluronic acid. Examples of the oligo hyaluronic acid may include an oligosaccharide chain having 2 (tetrasaccharide) or more and 8 or less of units each consisting of N-acetylglucosamine and glucuronic acid. The oligo hyaluronic acid can have 2 (tetrasaccharide) or 4 (octasaccharide) of the units.

The present invention also provides an oligosaccharide chain added GLP-1 peptide wherein the oligosaccharide chain is linked to at least one amino acid via a linker. Examples of the amino acid of the GLP-1 peptide bound to the linker may include Lys. In this case, the linker may contain an amino acid at the terminal bound to the oligosaccharide chain. Example of the amino acid contained at the oligosaccharide chain-bound terminal of the linker may include Asn.

In the present invention, the oligosaccharide chain is, preferably, substantially uniform and preferably has, e.g., at least 90% or at least 99% uniformity.

The oligosaccharide chain added GLP-1 peptide of the present invention, preferably, has higher stability in blood than that of GLP-1.

The oligosaccharide chain added GLP-1 peptide of the present invention can have the activity of controlling blood-sugar levels preferably at least 5 times, more preferably at least 10 times, even more preferably at least 20 times that of GLP-1 in OGTT (Oral Glucose Tolerance Test).

The oligosaccharide chain added GLP-1 peptide of the present invention can have DPP-IV resistance preferably at least 20 times, more preferably at least 30 times, even more preferably at least 50 times that of GLP-1.

The oligosaccharide chain added GLP-1 peptide of the present invention can be used as a novel active ingredient in medical application. Such medical application encompasses the treatment or prevention of diseases associated with GLP-1. Such diseases are typified by, e.g., diabetes.

Of course, one or any combination of the of the present invention described above is also incorporated in the oligosaccharide chain added GLP-1 peptide of the present invention.

Effect of the Invention

The oligosaccharide chain added GLP-1 peptide of the present invention has higher stability in blood than that of GLP-1. In one aspect of the present invention, the oligosaccharide chain added GLP-1 peptide of the present invention has higher activity of controlling blood-sugar levels than that of GLP-1. Accordingly, the oligosaccharide chain added GLP-1 peptide of the present invention can be administered at a lower dose and a smaller number of doses than those of GLP-1.

The oligosaccharide chain to be added to the oligosaccharide chain added GLP-1 peptide of the present invention is easily degraded in vivo and therefore, does not cause adverse reaction attributed to its accumulation in the living bodies.

Some or all of the added oligosaccharide chains in the oligosaccharide chain added GLP-1 peptide of the present invention are oligosaccharide chains existing in vivo in mammals including humans, birds, etc., or modified oligosaccharide chains thereof. They can hardly exhibit side effects or antigenicity, when administered to living bodies. Therefore, they do not present the problem of allergic reactions, antibody production, or a loss of efficacy attributed thereto.

Most of the oligosaccharide chains used in the present invention are relatively short. Therefore, those having uniform structure can be obtained without complicated production steps. Thus, a high-quality oligosaccharide chain added GLP-1 peptide of pharmaceutical level can be obtained stably in large amounts.

DETAILED DESCRIPTION OF THE PREFERRED EMBODIMENTS

Figure 1:
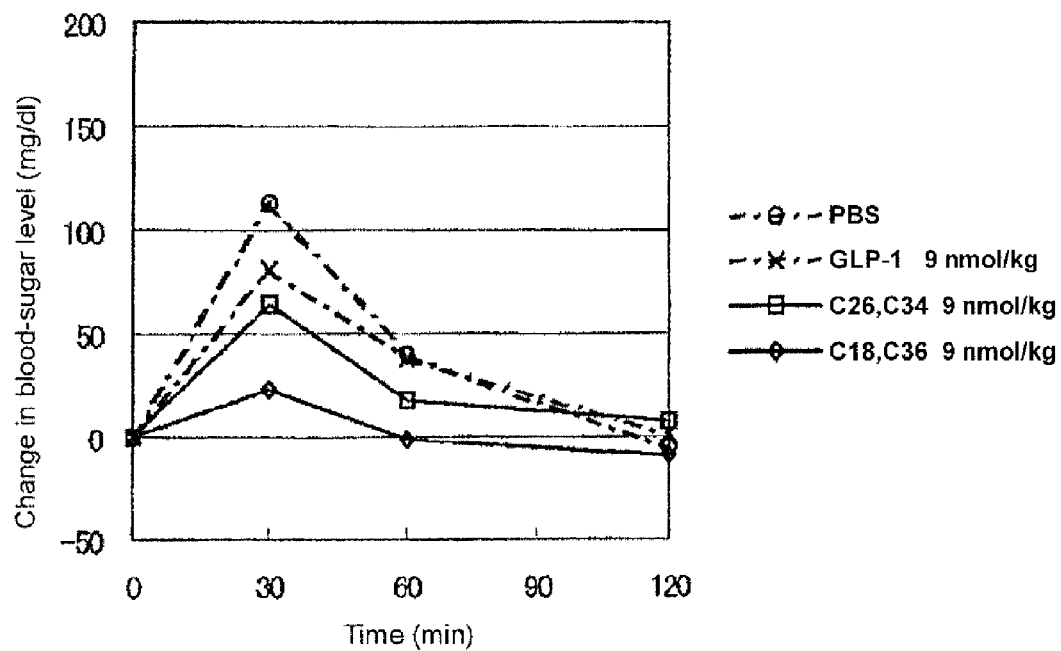
FIG. 1 shows the results of measuring, by Oral Glucose Tolerance Test (OGTT), the effect of suppressing rise in blood-sugar levels by the administration of an oligosaccharide chain added GLP-1 peptide (26 and 34Cys-disialo oligosaccharide chain added GLP-1 or 18 and 36Cys-disialo oligosaccharide chain added GLP-1) or GLP-1. The 26 and 34Cys-disialo oligosaccharide chain added GLP-1 or the 18 and 36Cys-disialo oligosaccharide chain added GLP-1 is administered at a dose of 0.9 nmol/kg, while the GLP-1 is administered at a dose of 9 nmol/kg.
Figure 2:
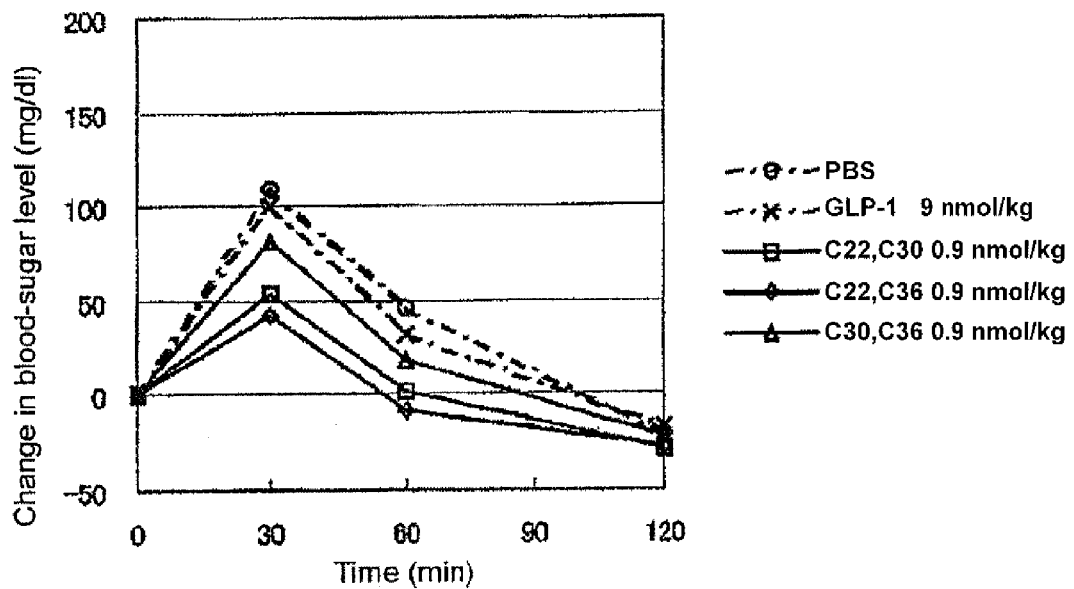
FIG. 2 shows the results of measuring, by Oral Glucose Tolerance Test (OGTT), the effect of suppressing rise in blood-sugar levels by the administration of an oligosaccharide chain added GLP-1 peptide (22 and 30Cys-disialo oligosaccharide chain added GLP-1, 22 and 36Cys-disialo oligosaccharide chain added GLP-1 or 30 and 36Cys-disialo oligosaccharide chain added GLP-1) or GLP-1. The 22 and 30Cys-disialo oligosaccharide chain added GLP-1, the 22 and 36Cys-disialo oligosaccharide chain added GLP-1 or the 30 and 36Cys-disialo oligosaccharide chain added GLP-1 is administered at a dose of 0.9 nmol/kg, while the GLP-1 is administered at a dose of 9 nmol/kg.
Figure 3:
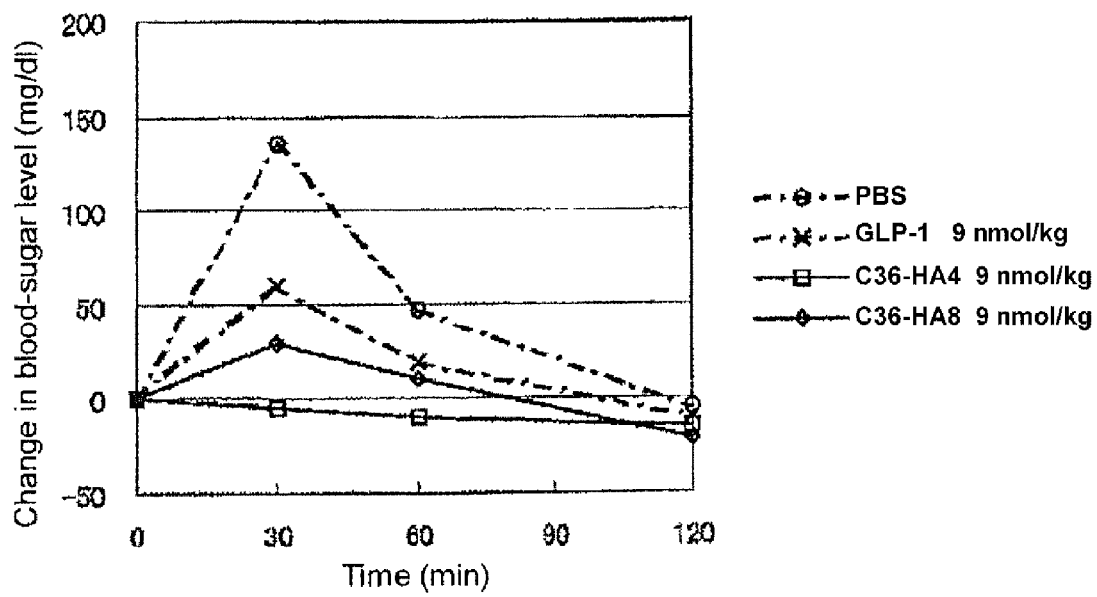
FIG. 3 shows the results of measuring, by Oral Glucose Tolerance Test (OGTT), the effect of suppressing rise in blood-sugar levels by the administration of an oligosaccharide chain added GLP-1 peptide (36Cys-hyaluronic acid tetrasaccharide added GLP-1 or 36Cys-hyaluronic acid octasaccharide added GLP-1) or GLP-1. The 36Cys-hyaluronic acid tetrasaccharide added GLP-1 or the 36Cys-hyaluronic acid octasaccharide added GLP-1 and the GLP-1 are respectively administered at a dose of 9 nmol/kg.
Figure 4:
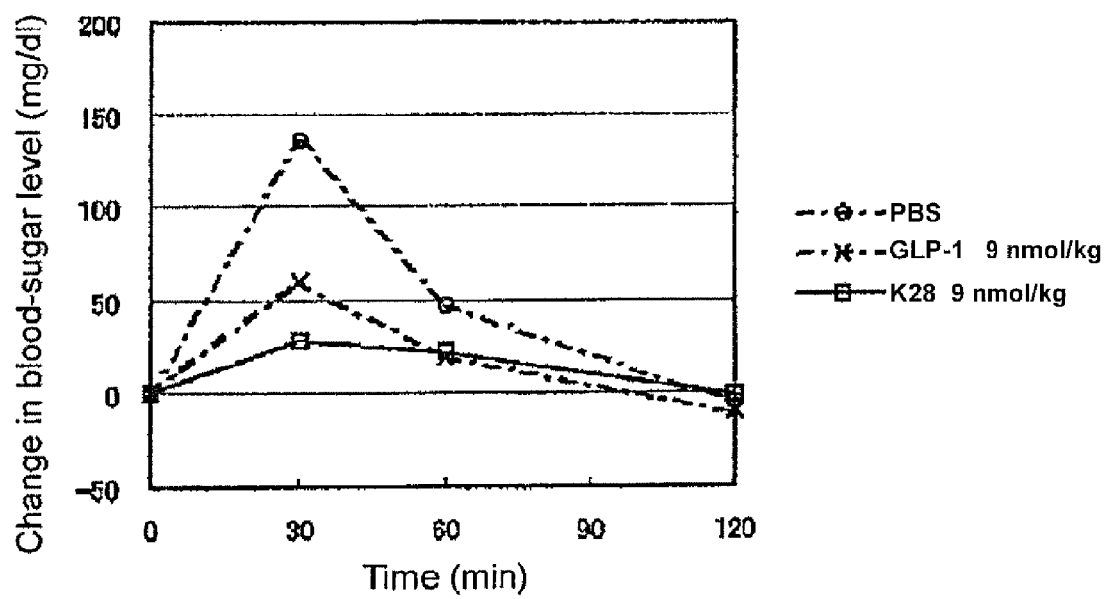
FIG. 4 shows the results of measuring, by Oral Glucose Tolerance Test (OGTT), the effect of suppressing rise in blood-sugar levels by the administration of an oligosaccharide chain added GLP-1 peptide (26Lys-asialo oligosaccharide chain Asn linker-modified GLP-1) or GLP-1. The 26Lys-asialo oligosaccharide chain Asn linker-modified GLP-1 and the GLP-1 are respectively administered at a dose of 9 nmol/kg.

"GLP=1" used herein represents glucagon-like peptide-1 and refers to GLP-1 (7-37).

The GLP-1 (7-37) has the amino acid sequence of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 2).

In the present invention, a "GLP-1 analog" is a peptide structurally similar to GLP-1 and/or a peptide structurally overlapping with GLP-1. Examples of such peptides include: a peptide having the amino acid sequence of GLP-1 with deletion, substitution or addition of one or more amino acids; a peptide having the amino acid sequence of GLP-1 with conservative substitution of one or several amino modified GLP-1; a GLP-1 fragment having GLP-1 activity; elongated GLP-1 having GLP-1 activity; and exendin-4 ("Ex-4" means exedin-4 in this specification) and its analog (Curr. Opin. Investig. Drugs 8, 842-8 (2007), J. Pharmacol. Exp. Ther. 307, 490-496 (2003), Diabetes 50, 2530-9 (2001), etc.).

The "amino acid" used herein is used in the broadest sense and encompasses not only natural amino acids but also normatural amino acids such as amino acid variants and derivatives. Taking this broad definition into consideration, those skilled in the art can understand that examples of the amino acid used herein include: natural proteogenic L-amino acids; D-amino acids; chemically modified amino acids such as amino acid variants and derivatives; natural nonproteogenic amino acids such as norleucine, β-alanine and ornithine; and chemically synthesized compounds having properties characteristic of amino acids known in the art. Examples of the normatural amino acids include α-methyl amino acids (α-methylalanine etc.), D-amino acids, histidine-like amino acids (2-amino-histidine, β-hydroxy-histidine, homohistidine, α-fluoromethyl-histidine and α-methyl-histidine, etc.), amino acids having extra methylene in the side chain ("homo"amino acids) and amino acids having a carboxylic acid functional group in the side chain substituted with a sulfonic acid group (cysteic acid etc.). Some GLP-1 analogs having GLP-1 activity have been known to contain normatural amino acids. In a preferable aspect, the amino acids contained in the compound of the present invention consist only of natural amino acids.

In the phrase "deletion, substitution or addition of one or several amino acids" used herein, the number of amino acids substituted, etc. is not particularly limited as long as GLP-1 activity is maintained. The number of amino acids substituted, etc. is 1 to about 9, preferably 1 to about 5, more preferably 1 to about 3 or corresponds to within 20%, preferably within 10% of the whole length. The amino acids substituted or added may be natural amino acids, normatural amino acids or amino acid analogs and are preferably natural amino acids. Examples of a GLP-1 peptide having "deletion, substitution or addition of one or several amino acids" include BIM51077 wherein 8Ala and 35Gly of GLP-1 are each substituted with a normatural amino acid α-methylalanine (also called aminoisobutanoic acid or Aib); 37Gly thereof is deleted; and 36Arg thereof is amidated (Curr. Opin. Investig. Drugs 8, 842-8 (2007)).

The "conservative substitution of one or several amino acids" used herein refers to amino acid substitution that substitutes the original amino acid with an amino acid having hydrophilicity and/or hydrophobicity indexes similar thereto and does not produce evident reduction or loss of GLP-1 activity after the substitution.

The "modified GLP-1" used herein is a compound wherein GLP-1 is naturally or artificially modified. Examples of such modification include alkylation, acylation (e.g., acetylation), amidation, carboxylation, esterification, disulfide bond formation, glycosylation, lipidation, phosphorylation, hydroxylation and labeling of one or several amino acid residues of GLP-1.

The "GLP-1 fragment having GLP-1 activity" used herein is a peptide that has deletion of one or more amino acids from the N terminal and/or C terminal of GLP-1 and maintains GLP-1 activity.

The "elongated GLP-1 having GLP-1 activity" used herein is a peptide that has addition of one or more amino acids to the N terminal and/or C terminal of GLP-1 and maintains GLP-1 activity (see e.g., Endocrinology, 125, 3109-14 (1989)).

In the phrase "peptide having one or several amino acids further added to the C terminal (position 37) of GLP-1" used herein, amino acids added to the C terminal of GLP-1 are sequentially referred to as an amino acid at position 38, an amino acid at position 39, . . . etc. In the "peptide having one or several amino acids further added to the N terminal (position 7) of GLP-1", amino acids added to the N terminal of GLP-1 are sequentially referred to as an amino acid at position 6, an amino acid at position 5, . . . etc. Examples of the "peptide having one amino acid further added to the C terminal (position 37) of GLP-1" include a peptide having Asn or Cys added to 37Gly of GLP-1.

The "oligosaccharide chain added GLP-1 peptide (glycosylated GLP-1 peptide, sugar chain added GLP-1 peptide)" of the present invention is characterized in that at least one amino acid is substituted with an oligosaccharide chain added amino acid.

The "oligosaccharide chain added GLP-1 peptide" used herein encompasses a peptide wherein at least one amino acid of GLP-1 is substituted with an oligosaccharide chain added amino acid and a peptide wherein at least one amino acid of the GLP-1 analog is substituted with an oligosaccharide chain added amino acid. These peptides are incorporated in the oligosaccharide chain added GLP-1 peptide, even when they further have deletion, substitution or addition of one or several amino acids except the oligosaccharide chain added amino acids. A peptide wherein the C terminal of any of these peptides is amidated (e.g., GLP-1 (7-36)NH$_2$ having the amino acid sequence of His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ (SEQ ID NO: 3), wherein at least one amino acid is substituted with an oligosaccharide chain added amino acid) is also incorporated in the oligosaccharide chain added GLP-1 peptide. Salts of these peptides are also incorporated in the oligosaccharide chain added GLP-1 peptide.

The salts used herein may be any of acid addition and base addition salts. Acids usually used for forming the acid addition salts are inorganic acids such as hydrochloric acid, hydrobromic acid, hydroiodic acid, sulfuric acid and phosphoric acid and organic acids such as p-toluenesulfonic acid, methanesulfonic acid, oxalic acid, p-bromophenylsulfonic acid, carboxylic acid, succinic acid, citric acid, benzoic acid and acetic acid. Examples of the base addition salts include salts derived from ammonium hydroxide or alkali or alkaline-earth metal hydroxides and salts derived from inorganic bases such as carbonate and bicarbonate. Particularly, pharmaceutically acceptable salts are preferable.

The "oligosaccharide chain added amino acid" used herein is an amino acid linked to an oligosaccharide chain. In this context, the oligosaccharide chain may be linked to the amino acid via a linker. The site of the oligosaccharide chain to which the amino acid is linked is not particularly limited. Preferably, the amino acid is linked to the reducing terminal of the oligosaccharide chain.

The type of the amino acid linked to the oligosaccharide chain is not particularly limited, and both natural and normatural amino acids can be used. From the viewpoint that the oligosaccharide chain added amino acid is structurally the same as or similar to those existing in a form of glycopeptide (glycoprotein) in vivo, the oligosaccharide chain added amino acid is preferably oligosaccharide chain added Asn such as an N-linked oligosaccharide chain or oligosaccharide chain added Ser and oligosaccharide chain added Thr such as an O-linked oligosaccharide chain, particularly preferably oligosaccharide chain added Asn.

When the oligosaccharide chain is linked to the amino acid via a linker, the amino acid in the oligosaccharide chain added amino acid is preferably: an amino acid having two or more carboxyl groups in the molecule, such as aspartic acid or glutamic acid; an amino acid having two or more amino groups in the molecule, such as lysine, arginine, histidine or tryptophan; an amino acid having a hydroxyl group in the molecule, such as serine, threonine or tyrosine; an amino acid having a thiol group in the molecule, such as or an amino acid having an amide group in the molecule, such as asparagine or glutamine, from the viewpoint of easy binding with the linker. Particularly, aspartic acid, glutamic acid, lysine, arginine, serine, threonine, cysteine, asparagine or glutamine is preferable from the viewpoint of reactivity.

The oligosaccharide chain added GLP-1 peptides of the present invention exhibits no large difference in the activity of suppressing rise in blood-sugar levels between oligosaccharide chain added Asn (without a linker) and oligosaccharide chain added Cys (via a linker) as an oligosaccharide chain added amino acid, when they had the same oligosaccharide chain structures, the same structures except oligosaccharide chain structures, the same oligosaccharide chain added sites and the same numbers of oligosaccharide chains to be added.

When the oligosaccharide chain is linked to the amino acid via a linker, any linkers widely used in the art can be used. Examples thereof may include: —NH—(CO)—$(CH_2)_a$—$CH_2$— wherein "a" represents an integer, preferably an integer of 0 to 4, but not limited to these numbers unless linker functions of interest are inhibited; $C_{1-10}$ polymethylene and —$CH_2$—R— wherein R is a group formed by removing one hydrogen atom from a group selected from the group consisting of alkyl, substituted alkyl, alkenyl, substituted alkenyl, alkynyl, substituted alkynyl, aryl, substituted aryl, a carbocyclic group, a substituted carbocyclic group, a heterocyclic group and a substituted heterocyclic group; and —(CO)—$(CH_2)_a$—(CO)— wherein "a" represents an integer, preferably an integer of 0 to 4, but not limited to these numbers unless linker functions of interest are inhibited.

In the oligosaccharide chain added amino acid, when the oligosaccharide chain is linked to the amino acid on the GLP-1 skeleton via a linker, the linker also preferably contains an amino acid at the terminal bound to the oligosaccharide chain. Preferable examples of the type of the amino acid may include, but not particularly limited to, Asn.

The oligosaccharide chain added GLP-1 peptide having the oligosaccharide chain added amino acid wherein the oligosaccharide chain is linked to the amino acid without a linker can have lower antigenicity than that of the oligosaccharide chain added GLP-1 peptide wherein the oligosaccharide chain is linked to the amino acid via a linker. The oligosaccharide chain added GLP-1 peptide having the oligosaccharide chain added amino acid wherein the oligosaccharide chain is linked to the amino acid via a linker can have higher stability in blood than that of the oligosaccharide chain added GLP-1 peptide wherein the oligosaccharide chain is linked to the amino acid without a linker.

A process for producing the oligosaccharide chain added GLP-1 peptide of the present invention is not limited by any means by the description (e.g., the description stating "oligosaccharide chain added GLP-1 peptide wherein an amino acid is substituted with an oligosaccharide chain added amino acid). An oligosaccharide chain added GLP-1 peptide produced by any of following Processes A-C is incorporated in the "oligosaccharide chain added GLP-1 peptide wherein an amino acid is substituted with a oligosaccharide chain added amino acid". Moreover, e.g.: an oligosaccharide chain added GLP-1 peptide wherein an amino acid-unlinked oligosaccharide chain is linked directly or via a linker to an amino acid in the peptide; an oligosaccharide chain added GLP-1 peptide wherein an oligosaccharide chain already added is further elongated by the addition of a sugar or oligosaccharide chain thereto; an oligosaccharide chain added GLP-1 peptide wherein one or several amino acids bound with amino and/or carboxyl groups of the oligosaccharide chain added amino acid are further linked to one or several GLP-1 fragments; and an oligosaccharide chain added GLP-1 peptide wherein an amino acid-linked oligosaccharide chain is linked via a linker to an amino acid in the peptide are also incorporated in the oligosaccharide chain added GLP-1 peptide of the present invention as long as their final structures are in agreement therewith.

The number of substitutions that substitute an amino acid of GLP-1 with an oligosaccharide chain added amino acid may be adjusted appropriately according to stability in blood, biological activities (e.g., the activity of controlling blood-sugar levels), the number of amino acids existing in the final oligosaccharide chain added GLP-1 peptide, the molecular weights of the oligosaccharide chain added GLP-1 peptide before and after the addition of oligosaccharide chain, etc. For example, 1 to 5 substitutions are preferable, and 1 to 3 substitutions are more preferable. In one aspect of the present invention, at least 2 substitutions, e.g., 2 to 5 substitutions are preferable, and 2 to 3 substitutions are more preferable. Preferably, one substitution may be selected from the viewpoint of convenience as long as this one substitution produces the desired activity. In general, an oligosaccharide chain added GLP-1 peptide wherein one amino acid of GLP-1 is substituted with an oligosaccharide chain added amino acid tends to exhibit enhanced stability in blood and reduced activity of controlling blood-sugar levels, when one or more amino acids except the oligosaccharide chain added amino acids are further substituted with an nligosaccharide chain added amino acid (however, the reduced activity of controlling blood-sugar levels can be compensated by the enhanced stability in blood).

In the oligosaccharide chain added GLP-1 peptide of the present invention, the substitution site of an amino acid with an oligosaccharide chain added amino acid can be adjusted appropriately according to stability in blood or the activity of controlling blood-sugar levels.

In one aspect of the present invention, the substitution site of an amino acid of GLP-1 with an oligosaccharide chain added amino acid can be selected from any sites of GLP-1 according to the desired activity and is, e.g., at least one site selected from positions 8, 9, 12, 18, 19, 20, 22, 26, 30, 34, 36 and 38 (=addition of an oligosaccharide chain added amino acid to an amino acid at position 37) of GLP1, preferably at least one site selected from positions 18, 20, 22, 26, 30, 34, 36 and 38, e.g., at least one site selected from positions 18, 26, 30, 34 and 36, and particularly at least one site selected from positions 30 and 36.

In one aspect of the present invention, from the viewpoint of the stability of the oligosaccharide chain added GLP-1 peptide in blood, the substitution site of an amino acid with an oligosaccharide chain added amino acid can be selected from any sites of GLP-1 and is, e.g., at least one site selected from positions 9, 10, 11, 12, 14, 16, 18, 19, 20, 22, 24, 25, 26, 27, 28, 30, 32, 34, 36 and 38 (=addition of an oligosaccharide chain added amino acid to an amino acid at position 37) of GLP-1, preferably at least one site selected from positions 9, 10, 11, 12, 14 and 28, and particularly preferably at least one site selected from positions 9, 10, 11 and 12. Particularly, substitution of an amino acid at a site close to the N terminal of GLP-1 is also preferable. Particularly, examples of the substitution sites of at least two amino acids of GLP-1 with oligosaccharide chain added amino acids may include substitution of positions 18 and 36, substitution of positions 26 and 34, substitution of positions 22 and 30, substitution of positions 22 and 36, and substitution of positions 30 and 36 of GLP-1.

In one aspect of the present invention, from the viewpoint of the effect of controlling blood-sugar levels by the oligosaccharide chain added GLP-1 peptide, the substitution site of an amino acid with an oligosaccharide chain added amino acid is, e.g., at least one site selected from positions 18, 20, 22, 26, 30, 34, 36 and 38 (=addition of an oligosaccharide chain added amino acid to an amino acid at position 37) of GLP-1, preferably at least one site selected from positions 18, 26, 30, 34 and 36, and particularly at least one site selected from positions 30 and 36. Particularly, examples of the substitution sites of at least two amino acids of GLP-1 with oligosaccharide chain added amino acids may include substitution of positions 18 and 36, substitution of positions 26 and 34, substitution of positions 22 and 30, substitution of positions 22 and 36, and substitution of positions 30 and 36 of GLP-1, from the viewpoint of the effect of controlling blood-sugar levels by the oligosaccharide chain added GLP-1 peptide.

In one aspect of the present invention, from the viewpoint of the ability to synthesize cAMP, of the GLP-1 activities of the oligosaccharide chain added GLP-1 peptide, the substitution site of an amino acid with an oligosaccharide chain added amino acid is preferably at least one site selected from positions 22, 26, 27, 30, 34, 36 and 38 (=addition of an oligosaccharide chain added amino acid to an amino acid at position 37), and more preferably at least one site selected from positions 22, 26, 30, 34, 36 and 38.

In one aspect of the present invention, the substitution site of an amino acid with an oligosaccharide chain added amino acid is at least one site selected from sites except positions 8, 9 and 12 of GLP-1.

In one aspect of the present invention, the substitution site of an amino acid with an oligosaccharide chain added amino acid is at least one site selected from sites except positions 7, 10, 13, 15, 19, 21, 28 and 29 of GLP-1, and particularly at least one site selected from sites except positions 7, 10, 15 and 28.

In one aspect of the present invention, the substitution site of an amino acid with an oligosaccharide chain added amino acid can be determined from the binding sites of GLP-1 to a GLP-1 receptor.

In one aspect of the present invention, when two or more amino acids are substituted with oligosaccharide chain added amino acids, the substitution sites of the amino acids with oligosaccharide chain added amino acids can be selected from, but not limited to, any of combinations of the sites described above. For example, a combination wherein one site is selected from the preferable sites and the other sites are selected from any sites of GLP-1, and a combination wherein one site is selected from the preferable sites and the other sites are selected from any sites of one or several amino acids further added to the C terminal (position 37) of GLP-1 are also incorporated in a preferable aspect of the present invention.

In one aspect of the present invention, preferable examples of the deletion, substitution or addition of one or several amino acids except the oligosaccharide chain added amino acid(s) in GLP-1 may include, but not limited to:

substitution of 8Ala with an amino acid selected from the group consisting of Gly, Ser, Thr, Leu, Ile, Val, Glu, Asp and Lys;

substitution of 9Glu with an amino acid selected from the group consisting of Asp and Lys; substitution of 11Thr with an amino acid selected from the group consisting of Ala, Gly, Ser, Leu, Ile, Val, Glu, Asp and Lys;

substitution of 12Phe with an amino acid selected from the group consisting of Trp and Tyr;

substitution of 13Thr with Ser;

substitution of 14Ser with an amino acid selected from the group consisting of Ala, Gly, Thr, Leu, Ile, Val, Glu, Asp and Lys;

substitution of 15Asp with Glu;

substitution of 16Val with an amino acid selected from the group consisting of Phe, Ala, Gly, Ser, Thr, Leu, Ile, Tyr, Glu, Asp and Lys;

substitution of 17Ser with an amino acid selected from the group consisting of Ala, Gly, Thr, Leu, Ile, Val, Glu, Asp and Lys;

substitution of 18Ser with an amino acid selected from the group consisting of Ala, Gly, Thr, Leu, Ile, Val, Glu, Asp and Lys;

substitution of 19Tyr with an amino acid selected from the group consisting of Phe, Trp, Glu, Asp and Lys;

substitution of 20Leu with an amino acid selected from the group consisting of Ala, Gly, Ser, Thr, Leu, Ile, Val, Glu, Asp and Lys substitution of 21Glu with an amino acid selected from the group consisting of Asp and Lys;

substitution of 22Gly with an amino acid selected from the group consisting of Ala, Ser, Thr, Leu, Ile, Val, Glu, Asp and Lys;

substitution of 23Gln with an amino acid selected from the group consisting of Asn, Arg, Glu, Asp and Lys;

substitution of 24Ala with an amino acid selected from the group consisting of Gly, Ser, Thr, Leu, Ile, Val, Arg, Glu, Asp and Lys;

substitution of 25Ala with an amino acid selected from the group consisting of Gly, Ser, Thr, Leu, Ile, Val, Glu, Asp and Lys;

substitution of 26Lys with an amino acid selected from the group consisting of Arg, Gln, Glu, Asp and His;

substitution of 27Glu with an amino acid selected from the group consisting of Asp, Ile and Lys;

substitution of 28Phe with Trp;

substitution of 29Ile with an amino acid selected from the group consisting of Leu, Val and Ala;

substitution of 30Ala with an amino acid selected from the group consisting of Gly, Ser, Thr, Leu, Ile, Val, Glu, Asp and Lys;

substitution of 31Trp with an amino acid selected from the group consisting of Phe, Tyr, Glu, Asp and Lys;

substitution of 32Leu with an amino acid selected from the group consisting of Gly, Ala, Ser, Thr, Ile, Val, Glu, Asp and Lys;

substitution of 33Val with an amino acid selected from the group consisting of Gly, Ala, Ser, Thr, Leu, Ile, Glu, Asp and Lys;

substitution of 34Lys with an amino acid selected from the group consisting of Arg, Glu, Asp and His;

substitution of 35Gly with an amino acid selected from the group consisting of Ala, Ser, Thr, Leu, Ile, Val, Glu, Asp and Lys;

substitution of 36Arg with an amino acid selected from the group consisting of Lys, Glu, Asp and His; and/or substitution of 37Gly with an amino acid selected from the group consisting of Ala, Ser, Thr, Leu, Ile, Val, Glu, Asp and Lys.

In one aspect of the present invention, a site of the deletion, substitution or addition of amino acids except the oligosaccharide chain added amino acids is preferably at least one site selected from sites except positions 7, 10, 13, 15, 19, 21, 28 and 29 of GLP-1, e.g., at least one site selected from sites except positions 7, 10, 15 and 28, (Structure-Activity Studies of Glucagon-like Peptide-1, THE JOURNAL OF BIOLOGICAL CHEMISTRY Vol. 269, No. 9, Issue of March 4, pp. 6276-6278. 1994).

Examples of the oligosaccharide chain added GLP-1 peptide of the present invention include an oligosaccharide chain added GLP-1 peptide represented by the general formula (1):

```
His-Ala-Glu-Gly-Thr-Phe-Thr-Ser-Asp-Val-Ser-
Xaa18-Xaa19-Leu-Glu-Xaa22-Gln-Ala-Ala-Xaa26-
Glu-Phe-Ile-Xaa30-Trp-Leu-Val-Xaa34-Gly-Xaa36-
Xaa37
``` wherein:

$Xaa_{18}$ represents Ser, oligosaccharide chain added Cys or oligosaccharide chain added Asn;

$Xaa_{19}$ represents Tyr, oligosaccharide chain added Cys or oligosaccharide chain added Asn;

$Xaa_{22}$ represents Gly, oligosaccharide chain added Cys or oligosaccharide chain added Asn;

$Xaa_{26}$ represents Lys, oligosaccharide chain added Cys, oligosaccharide chain added Asn or oligosaccharide chain added Lys;

$Xaa_{30}$ represents Ala, oligosaccharide chain added Cys or oligosaccharide chain added Asn;

$Xaa_{34}$ represents Lys, oligosaccharide chain added Cys, oligosaccharide chain added Asn or oligosaccharide chain added Lys;

$Xaa_{36}$ represents Arg, oligosaccharide chain added Cys or oligosaccharide chain added Asn;

$Xaa_{37}$ represents Gly, $NH_2$, Gly-oligosaccharide chain added Cys or Gly-oligosaccharide chain added Asn, and when $Xaa_{18}$ is Ser, $Xaa_{19}$ is Tyr, $Xaa_{22}$ is Gly, $Xaa_{26}$ is Lys, $Xaa_{30}$ is Ala, $Xaa_{34}$ is Lys, and $Xaa_{36}$ is Arg, then $Xaa_{37}$ represents Gly-oligosaccharide chain added Cys or Gly-oligosaccharide chain added Asn, wherein: at least two amino acids of the parent peptide are each substituted with an oligosaccharide chain added amino acid; the oligosaccharide chain is oligo hyaluronic acid; and/or the oligosaccharide chain is a high-mannose type oligosaccharide chain. Each of the oligosaccharide chain added Cys, the oligosaccharide chain added Asn and the oligosaccharide chain added Lys may contain a linker between the oligosaccharide chain and the amino acid. The peptide represented by the general formula (1) is represented by SEQ ID NO: 1 herein.

Specific examples of the oligosaccharide chain added GLP-1 peptide of the present invention include:

(a1) a peptide represented by the general formula (1) wherein $Xaa_{18}$ represents oligosaccharide chain added Cys, $Xaa_{19}$ represents Tyr, $Xaa_{22}$ represents Gly, $Xaa_{26}$ represents Lys, $Xaa_{30}$ represents Ala, $Xaa_{34}$ represents Lys, $Xaa_{36}$ represents Arg and $Xaa_{37}$ represents Gly (SEQ ID NO: 4);

(a2) a peptide represented by the general formula (1) wherein $Xaa_{18}$ represents Ser, $Xaa_{19}$ represents Tyr, $Xaa_{22}$ represents oligosaccharide chain added Cys, $Xaa_{26}$ represents Lys, $Xaa_{30}$ represents Ala, $Xaa_{34}$ represents Lys, $Xaa_{36}$ represents Arg and $Xaa_{37}$ represents Gly (SEQ ID NO: 5);

(a3) a peptide represented by the general formula (1) wherein $Xaa_{18}$ represents Ser, $Xaa_{19}$ represents Tyr, $Xaa_{22}$ represents Gly, $Xaa_{26}$ represents oligosaccharide chain added Cys, $Xaa_{30}$ represents Ala, $Xaa_{34}$ represents Lys, $Xaa_{36}$ represents Arg and $Xaa_{37}$ represents Gly (SEQ ID NO: 6);

(a4) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{30}$ represents oligosaccharide chain added Cys, $Xaa_{34}$ represents Lys, $Xaa_{36}$ represents Arg and $Xaa_{37}$ represents Gly (SEQ ID NO: 7);

(a5) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{30}$ represents Ala, $Xaa_{34}$ represents oligosaccharide chain added Cys, $Xaa_{36}$ represents Arg and $Xaa_{37}$ represents Gly (SEQ ID NO: 8);

(a6) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{30}$ represents Ala, $Xaa_{34}$ represents Lys, $Xaa_{36}$ represents oligosaccharide chain added Cys and $Xaa_{37}$ represents Gly (SEQ ID NO: 9);

(a7) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{30}$ represents Ala, $Xaa_{34}$ represents Lys, $Xaa_{36}$ represents Arg and $Xaa_{37}$ represents Gly-oligosaccharide chain added Cys (SEQ ID NO: 10);

(a8) a peptide represented by the general formula (1) wherein $Xaa_{18}$ represents Ser, $Xaa_{19}$ represents oligosaccharide chain added Cys, $Xaa_{22}$ represents Gly, $Xaa_{26}$ represents Lys, $Xaa_{30}$ represents Ala, $Xaa_{34}$ represents Lys, $Xaa_{36}$ represents Arg and $Xaa_{37}$ represents Gly (SEQ ID NO: 11);

(a9) a peptide represented by the general formula (1) wherein $Xaa_{18}$ represents oligosaccharide chain added Asn, $Xaa_{19}$ represents Tyr, $Xaa_{22}$ represents Gly, $Xaa_{26}$ represents Lys, $Xaa_{30}$ represents Ala, $Xaa_{34}$ represents Lys, $Xaa_{36}$ represents Arg and $Xaa_{37}$ represents Gly (SEQ ID NO: 12);

(a10) a peptide represented by the general formula (1) wherein $Xaa_{18}$ represents Ser, $Xaa_{19}$ represents Tyr, $Xaa_{22}$ represents oligosaccharide chain added Asn, $Xaa_{26}$ represents Lys, $Xaa_{30}$ represents Ala, $Xaa_{34}$ represents Lys, $Xaa_{36}$ represents Arg and $Xaa_{37}$ represents Gly (SEQ ID NO: 13);

(a11) a peptide represented by the general formula (1) wherein $Xaa_{18}$ represents Ser, $Xaa_{19}$ represents Tyr, $Xaa_{22}$ represents Gly, $Xaa_{26}$ represents oligosaccharide chain added Asn, $Xaa_{30}$ represents Ala, $Xaa_{34}$ represents Lys, $Xaa_{36}$ represents Arg and $Xaa_{37}$ represents Gly (SEQ ID NO: 14);

(a12) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{30}$ represents oligosaccharide chain added Asn, $Xaa_{34}$ represents Lys, $Xaa_{36}$ represents Arg and $Xaa_{37}$ represents Gly (SEQ ID NO: 15);

(a13) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{30}$ represents Ala, $Xaa_{34}$ represents oligosaccharide chain added Asn, $Xaa_{36}$ represents Arg and $Xaa_{37}$ represents Gly (SEQ ID NO: 16);

(a14) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{30}$ represents Ala, $Xaa_{34}$ represents Lys, $Xaa_{36}$ represents oligosaccharide chain added Asn and $Xaa_{37}$ represents Gly (SEQ ID NO: 17);

(a15) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{30}$ represents Ala, $Xaa_{34}$ represents Lys, $Xaa_{36}$ represents Arg and $Xaa_{37}$ represents Gly-oligosaccharide chain added Asn (SEQ ID NO: 18);

(a16) a peptide represented by the general formula (1) wherein $Xaa_{18}$ represents Ser, $Xaa_{19}$ represents oligosaccharide chain added Asn, $Xaa_{22}$ represents Gly, $Xaa_{26}$ represents Lys, $Xaa_{30}$ represents Ala, $Xaa_{34}$ represents Lys, $Xaa_{36}$ represents Arg and $Xaa_{37}$ represents Gly (SEQ ID NO: 19);

(a17) a peptide represented by the general formula (1) wherein $Xaa_{18}$ represents oligosaccharide chain added Cys, $Xaa_{19}$ represents Tyr, $Xaa_{22}$ represents Gly, $Xaa_{26}$ represents Lys, Xaa$_{30}$ represents Ala, Xaa$_{34}$ represents Lys, Xaa$_{36}$ represents Arg and Xaa$_{37}$ represents NH$_2$ (SEQ ID NO: 20);

(a18) a compound represented by the general formula (1) wherein Xaa$_{18}$ represents Ser, Xaa$_{19}$ represents Tyr, Xaa$_{22}$ represents oligosaccharide chain added Cys, Xaa$_{26}$ represents Lys, Xaa$_{30}$ represents Ala, Xaa$_{34}$ represents Lys, Xaa$_{36}$ represents Arg and Xaa$_{37}$ represents NH$_2$ (SEQ ID NO: 21);

(a19) a compound represented by the general formula (1) wherein Xaa$_{18}$ represents Ser, Xaa$_{19}$ represents Tyr, Xaa$_{22}$ represents Gly, Xaa$_{26}$ represents oligosaccharide chain added Cys, Xaa$_{30}$ represents Ala, Xaa$_{34}$ represents Lys, Xaa$_{36}$ represents Arg and Xaa$_{37}$ represents NH$_2$ (SEQ ID NO: 22);

(a20) a compound represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents oligosaccharide chain added Cys, Xaa$_{34}$ represents Lys, Xaa$_{36}$ represents Arg and Xaa$_{37}$ represents NH$_2$ (SEQ ID NO: 23);

(a21) a compound represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents Ala, Xaa$_{34}$ represents oligosaccharide chain added Cys, Xaa$_{36}$ represents Arg and Xaa$_{37}$ represents NH$_2$ (SEQ ID NO: 24);

(a22) a peptide represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents Ala, Xaa$_{34}$ represents Lys, Xaa$_{36}$ represents oligosaccharide chain added Cys and Xaa$_{37}$ represents NH$_2$ (SEQ ID NO: 25);

(a23) a peptide represented by the general formula (1) wherein Xaa$_{18}$ represents Ser, Xaa$_{19}$ represents oligosaccharide chain added Xaa$_{22}$ represents Gly, Xaa$_{26}$ represents Lys, Xaa$_{30}$ represents Ala, Xaa$_{34}$ represents Lys, Xaa$_{36}$ represents Arg and Xaa$_{37}$ represents NH$_2$ (SEQ ID NO: 26);

(a24) a peptide represented by the general formula (1) wherein Xaa$_{18}$ represents oligosaccharide chain added Asn, Xaa$_{19}$ represents Tyr, Xaa$_{22}$ represents Gly, Xaa$_{26}$ represents Lys, Xaa$_{30}$ represents Ala, Xaa$_{34}$ represents Lys, Xaa$_{36}$ represents Arg and Xaa$_{37}$ represents NH$_2$ (SEQ ID NO: 27);

(a25) a peptide represented by the general formula (1) wherein Xaa$_{18}$ represents Ser, Xaa$_{19}$ represents Tyr, Xaa$_{22}$ represents oligosaccharide chain added Asn, Xaa$_{26}$ represents Lys, Xaa$_{30}$ represents Ala, Xaa$_{34}$ represents Lys, Xaa$_{36}$ represents Arg and Xaa$_{37}$ represents NH$_2$ (SEQ ID NO: 28);

(a26) a peptide represented by the general formula (1) wherein Xaa$_{18}$ represents Ser, Xaa$_{19}$ represents Tyr, Xaa$_{22}$ represents Gly, Xaa$_{26}$ represents oligosaccharide chain added Asn, Xaa$_{30}$ represents Ala, Xaa$_{34}$ represents Lys, Xaa$_{36}$ represents Arg and Xaa$_{37}$ represents NH$_2$ (SEQ ID NO: 29);

(a27) a peptide represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents oligosaccharide chain added Asn, Xaa$_{34}$ represents Lys, Xaa$_{36}$ represents Arg and Xaa$_{37}$ represents NH$_2$ (SEQ ID NO: 30);

(a28) a peptide represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents Ala, Xaa$_{34}$ represents oligosaccharide chain added Asn, Xaa$_{36}$ represents Arg and Xaa$_{37}$ represents NH$_2$ (SEQ ID NO: 31);

(a29) a peptide represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents Ala, Xaa$_{34}$ represents Lys, Xaa$_{36}$ represents oligosaccharide chain added Asn and Xaa$_{37}$ represents NH$_2$ (SEQ ID NO: 32); and (a30) a peptide represented by the general formula (1) wherein Xaa$_{18}$ represents Ser, Xaa$_{19}$ represents oligosaccharide chain added Asn, Xaa$_{22}$ represents Gly, Xaa$_{26}$ represents Lys, Xaa$_{30}$ represents Ala, Xaa$_{34}$ represents Lys, Xaa$_{36}$ represents Arg and Xaa$_{37}$ represents NH$_2$ (SEQ ID NO: 33).

In these examples of the oligosaccharide chain added GLP-1 peptide, the oligosaccharide chain is preferably, for example, oligo hyaluronic acid or a high-mannose type oligosaccharide chain.

Examples of the oligosaccharide chain added GLP-1 peptide of the present invention also include:

(a31) a peptide represented by the general formula (1) wherein Xaa$_n$ represents Ser, Xaa$_{19}$ represents Tyr, Xaa$_{22}$ represents Gly, Xaa$_{26}$ represents oligosaccharide chain added Lys, Xaa$_{30}$ represents Ala, Xaa$_{34}$ represents Lys, Xaa$_{36}$ represents Arg and Xaa$_{37}$ represents Gly (SEQ ID NO: 34); and (a32) a peptide represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents Ala, Xaa$_{34}$ represents oligosaccharide chain added Lys, Xaa$_{36}$ represents Arg and Xaa$_{37}$ represents Gly (SEQ ID NO: 35).

In these examples of the oligosaccharide chain added GLP-1 peptide, the oligosaccharide chain is preferably linked to Lys via a linker, for example, in the oligosaccharide chain added Lys.

Examples of the oligosaccharide chain added GLP-1 peptide of the present invention also include:

(a33) a peptide represented by the general formula (1) wherein Xaa$_{IE}$, represents oligosaccharide chain added Cys, Xaa$_{19}$ represents Tyr, Xaa$_{22}$ represents Gly, Xaa$_{26}$ represents Lys, Xaa$_{30}$ represents Ala, Xaa$_{34}$ represents Lys, Xaa$_{36}$ represents oligosaccharide chain added Cys and Xaa$_{37}$ represents Gly (SEQ ID NO: 36);

(a34) a peptide represented by the general formula (1) wherein Xaa$_{18}$ represents Ser, Xaa$_{19}$ represents Tyr, Xaa$_{22}$ represents oligosaccharide chain added Cys, Xaa$_{26}$ represents Lys, Xaa$_{30}$ represents oligosaccharide chain added Cys, Xaa$_{34}$ represents Lys, Xaa$_{36}$ represents Arg and Xaa$_{37}$ represents Gly (SEQ ID NO: 37);

(a35) a peptide represented by the general formula (1) wherein Xaa$_{18}$ represents Ser, Xaa$_{19}$ represents Tyr, Xaa$_{22}$ represents oligosaccharide chain added Cys, Xaa$_{26}$ represents Lys, Xaa$_{30}$ represents Ala, Xaa$_{34}$ represents Lys, Xaa$_{36}$ represents oligosaccharide chain added Cys and Xaa$_{37}$ represents Gly (SEQ ID NO: 38);

(a36) a peptide represented by the general formula (1) wherein Xaa$_{18}$ represents Ser, Xaa$_{19}$ represents Tyr, Xaa$_{22}$ represents Gly, Xaa$_{26}$ represents oligosaccharide chain added Cys, Xaa$_{30}$ represents Ala, Xaa$_{34}$ represents oligosaccharide chain added Cys, Xaa$_{36}$ represents Arg and Xaa$_{37}$ represents Gly (SEQ ID NO: 39);

(a37) a peptide represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents oligosaccharide chain added Cys, Xaa$_{34}$ represents Lys, Xaa$_{36}$ represents oligosaccharide chain added Cys and Xaa$_{37}$ represents Gly (SEQ ID NO: 40);

(a38) a peptide represented by the general formula (1) wherein Xaa$_{19}$ represents oligosaccharide chain added Asn, Xaa$_{19}$ represents Tyr, Xaa$_{22}$ represents Gly, Xaa$_{26}$ represents Lys, Xaa$_{30}$ represents Ala, Xaa$_{34}$ represents Lys, Xaa$_{36}$ represents oligosaccharide chain added Asn and Xaa$_{37}$ represents Gly (SEQ ID NO: 41);

(a39) a peptide represented by the general formula (1) wherein Xaa$_{18}$ represents Ser, Xaa$_{19}$ represents Tyr, Xaa$_{22}$ represents oligosaccharide chain added Asn, Xaa$_{26}$ represents Lys, Xaa$_{30}$ represents oligosaccharide chain added Asn, Xaa$_{34}$ represents Lys, Xaa$_{36}$ represents Arg and Xaa$_{37}$ represents Gly (SEQ ID NO: 42);

(a40) a peptide represented by the general formula (1) wherein Xaa$_{18}$ represents Ser, Xaa$_{19}$ represents Tyr, Xaa$_{22}$ represents oligosaccharide chain added Asn, Xaa$_{26}$ represents Lys, Xaa$_{30}$ represents Ala, Xaa$_{34}$ represents Lys, Xaa$_{36}$ represents oligosaccharide chain added Asn and Xaa$_{37}$ represents Gly (SEQ ID NO: 43);

(a41) a peptide represented by the general formula (1) wherein Xaa$_{18}$ represents Ser, Xaa$_{19}$ represents Tyr, Xaa$_{22}$ represents Gly, Xaa$_{26}$ represents oligosaccharide chain added Asn, Xaa$_{30}$ represents Ala, Xaa$_{34}$ represents oligosaccharide chain added Asn, Xaa$_{36}$ represents Arg and Xaa$_{37}$ represents Gly (SEQ ID NO: 44); and (a42) a peptide represented by the general formula (1) wherein Xaa$_{18}$ represents Ser, Xaa$_{19}$ represents Tyr, Xaa$_{22}$ represents Gly, Xaa$_{26}$ represents Lys, Xaa$_{30}$ represents oligosaccharide chain added Asn, Xaa$_{34}$ represents Lys, Xaa$_{36}$ represents oligosaccharide chain added Asn and Xaa$_{37}$ represents Gly (SEQ ID NO: 45).

In these examples of the oligosaccharide chain added GLP-1 peptide, the oligosaccharide chain is preferably, for example, a biantennary complex-type oligosaccharide chain.

Examples of the oligosaccharide chain added GLP-1 peptide of the present invention also include:

(a43) a peptide represented by the general formula (1) wherein Xaa$_{18}$ represents oligosaccharide chain added Cys, Xaa$_{19}$ represents Tyr, Xaa$_{22}$ represents oligosaccharide chain added Cys, Xaa$_{26}$ represents Lys, Xaa$_{30}$ represents Ala, Xaa$_{34}$ represents Lys, Xaa$_{36}$ represents Arg and Xaa$_{37}$ represents Gly-oligosaccharide chain added Cys (SEQ ID NO: 46);

(a44) a peptide represented by the general formula (1) wherein Xaa$_{18}$ represents oligosaccharide chain added Cys, Xaa$_{19}$ represents Tyr, Xaa$_{22}$ represents oligosaccharide chain added Cys, Xaa$_{26}$ represents oligosaccharide chain added Cys, Xaa$_{30}$ represents Ala, Xaa$_{34}$ represents Lys, Xaa$_{36}$ represents Arg and Xaa$_{37}$ represents Gly (SEQ ID NO: 47);

(a45) a peptide represented by the general formula (1) wherein Xaa$_{18}$ represents Ser, Xaa$_{19}$ represents Tyr, Xaa$_{22}$ represents Gly, Xaa$_{26}$ represents oligosaccharide chain added Asn, Xaa$_{30}$ represents Ala, Xaa$_{34}$ represents Lys, Xaa$_{36}$ represents oligosaccharide chain added Asn and Xaa$_{37}$ represents Gly-oligosaccharide chain added Asn (SEQ ID NO: 48); and (a46) a peptide represented by the general formula (1) wherein Xaa$_{18}$ represents oligosaccharide chain added Asn, Xaa$_{19}$ represents Tyr, Xaa$_{22}$ represents oligosaccharide chain added Asn, Xaa$_{26}$ represents oligosaccharide chain added Asn, Xaa$_{30}$ represents Ala, Xaa$_{34}$ represents Lys, Xaa$_{36}$ represents Arg and Xaa$_{37}$ represents NH$_2$ (SEQ ID NO: 49).

In these examples of the oligosaccharide chain added GLP-1 peptide, the oligosaccharide chain is preferably, for example, a biantennary complex-type oligosaccharide chain.

Examples of the oligosaccharide chain added GLP-1 peptide analog of the present invention may include exendin-4 having the amino acid sequence of H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO: 50) and having an oligosaccharide chain added thereto.

The oligosaccharide chain added exendin-4 is represented by, for example, the general formula (2):

```
H-His-Gly-Glu-Gly-Thr-Phe-Thr-Ser-Asp-Leu-Ser-

Xaa₁₂-Gln-Xaa₁₄-Glu-Xaa₁₆-Glu-Ala-Val-Xaa₂₀-Leu-

Phe-Ile-Xaa₂₄-Trp-Leu-Lys-Xaa₂₈-Gly-Xaa₃₀-Pro-

Ser-Ser-Gly-Ala-Pro-Pro-Pro-Ser-NH₂
``` wherein:

Xaa$_{12}$ represents Lys, oligosaccharide chain added Cys or oligosaccharide chain added Asn;

Xaa$_{14}$ represents Met, oligosaccharide chain added Cys or oligosaccharide chain added Asn;

Xaa$_{16}$ represents Glu, oligosaccharide chain added Cys or oligosaccharide chain added Asn;

Xaa$_{20}$ represents Arg, oligosaccharide chain added Cys or oligosaccharide chain added Asn;

Xaa$_{24}$ represents Glu, oligosaccharide chain added Cys or oligosaccharide chain added Asn;

Xaa$_{28}$ represents Asn, oligosaccharide chain added Cys or oligosaccharide chain added Asn;

Xaa$_{30}$ represents Gly, oligosaccharide chain added Cys or oligosaccharide chain added Asn; and at least one of Xaa$_{12}$, Xaa$_{14}$, Xaa$_{16}$, Xaa$_{20}$, Xaa$_{24}$, Xaa$_{28}$ and Xaa$_{30}$ is oligosaccharide chain added Cys or oligosaccharide chain added Asn (SEQ ID NO: 51).

Among them, for example, Xaa$_{24}$ and/or Xaa$_{30}$ are preferably oligosaccharide chain added Cys or oligosaccharide chain added Asn. Particularly, Xaa$_{30}$ is preferably oligosaccharide chain added Cys.

Examples of an oligosaccharide chain added GLP-1 peptide having deletion, substitution or addition of one or several amino acids in GLP-1, which is the oligosaccharide chain added GLP-1 of the present invention, may include BIM51077 having the amino acid sequence of His-R2-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-R2-Arg-NH$_2$ wherein R$^2$ represents α-methylalanine (SEQ ID NO: 52) and having an oligosaccharide chain added thereto.

The oligosaccharide chain added BIM51077 is represented by, for example, the general formula (3):

```
His-R2-Glu-Gly-Thr-Phe-Thr-Ser-Asp-Val-Ser-

Xaa₁₈-Tyr-Xaa₂₀-Glu-Xaa₂₂-Gln-Ala-Ala-Xaa₂₆-

Glu-Phe-Ile-Xaa₃₀-Trp-Leu-Val-Xaa₃₄-R2-Xaa₃₆-NH₂
``` wherein:

R2 represents α-methylalanine;

Xaa$_{18}$ represents Ser, oligosaccharide chain added Cys or oligosaccharide chain added Asn;

Xaa$_{20}$ represents Leu, oligosaccharide chain added Cys or oligosaccharide chain added Asn;

Xaa$_{22}$ represents Gly, oligosaccharide chain added Cys or oligosaccharide chain added Asn;

Xaa$_{26}$ represents Lys, oligosaccharide chain added Cys, oligosaccharide chain added Asn or oligosaccharide chain added Lys;

Xaa$_{30}$ represents Ala, oligosaccharide chain added Cys or oligosaccharide chain added Asn;

Xaa$_{34}$ represents Lys, oligosaccharide chain added Cys, oligosaccharide chain added Asn or oligosaccharide chain added Lys;

Xaa$_{36}$ represents Arg, oligosaccharide chain added Cys or oligosaccharide chain added Asn, and at least one of Xaa$_{18}$, Xaa$_{20}$, Xaa$_{22}$, Xaa$_{26}$, Xaa$_{30}$, Xaa$_{34}$ and Xaa$_{36}$ is oligosaccharide chain added Cys or oligosaccharide chain added Asn (SEQ ID NO: 53).

When an oligosaccharide chain added amino acid wherein an oligosaccharide chain is added to an amino acid at the C terminal of a peptide originally having an amidated C terminal, such as exendin-4 and BIM51077, is synthesized, the C terminal may not be amidated.

The "oligosaccharide chain" used herein refers to a compound composed of at least one sugar unit (monosaccharide and/or its derivative). When two or more sugar units are linked, these sugar units are bound by dehydrating condensation through a glycosidic linkage between them. Examples of such a oligosaccharide chain include, but not limited to, monosaccharides and polysaccharides (glucose, galactose, mannose, fucose, xylose, N-acetylglucosamine, N-acetylgalactosamine, sialic acid and their complexes and derivatives) contained in living bodies as well as a wide range of oligosaccharide chains such as degraded polysaccharides and those degraded or derived from complex biological molecules such as glycoproteins, proteoglycans, glycosaminoglycans and glycolipids. The oligosaccharide chain may be linear or branched.

The "oligosaccharide chain" used herein also encompasses oligosaccharide chain derivatives. Examples of the oligosaccharide chain derivatives include, but not limited to, oligosaccharide chains composed of a sugar having a carboxyl group (e.g., aldonic acid which is carboxylic acid formed by oxidation at C-1 position (e.g., D-gluconic acid formed by the oxidation of D-glucose) and uronic acid wherein the terminal carbon atom has been oxidized to a carboxyl group (D-glucuronic acid formed by the oxidation of D-glucose)); a sugar having an amino group or amino group derivative (e.g., acetylated amino group) (e.g., N-acetyl-D-glucosamine and N-acetyl-D-galactosamine); a sugar having both amino and carboxyl groups (e.g., N-acetylneuraminic acid (sialic acid) and N-acetylmuramic acid); a deoxy sugar (e.g., 2-deoxy-D-ribose); a sulfated sugar containing a sulfuric acid group; and a phosphorylated sugar containing a phosphoric acid group.

In the present invention, preferable oligosaccharide chains enhance stability of GLP-1 in blood and, more preferably, do not delete the activity of controlling blood-sugar levels of GLP-1, when added to GLP-1 (i.e., when an amino acid of GLP-1 is substituted with an oligosaccharide chain added amino acid). In one aspect of the present invention, preferable oligosaccharide chains enhance the activity of controlling blood-sugar levels of GLP-1, when added to GLP-1 (i.e., when an amino acid of GLP-1 is substituted with an oligosaccharide chain added amino acid).

The oligosaccharide chain in the oligosaccharide chain added GLP-1 peptide of the present invention is not particularly limited and may or may not exist in vivo in a form of complex carbohydrate (glycopeptide (or glycoprotein), proteoglycan, glycolipid, etc.).

The oligosaccharide chain that exists in vivo in a form of complex carbohydrate is preferable from the viewpoint that the oligosaccharide chain added GLP-1 peptide of the present invention is administered to living bodies. Examples of such an oligosaccharide chain include an N-linked oligosaccharide chain and an O-linked oligosaccharide chain, which are bound in vivo to a peptide (or protein) to form a glycopeptide (or glycoprotein). Preferably, the N-linked oligosaccharide chain is used. Examples of the N-linked oligosaccharide chain may include a high-mannose type, a complex type and a hybrid type. The complex type is particularly preferable.

Examples of preferable complex-type oligosaccharide chains usable in the present invention include an oligosaccharide chain represented by the following general formula:

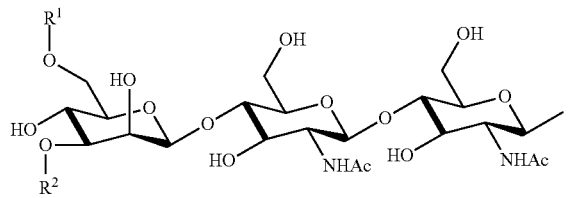

[Formula 3]

wherein $R^1$ and $R^2$ are the same or different and each represents

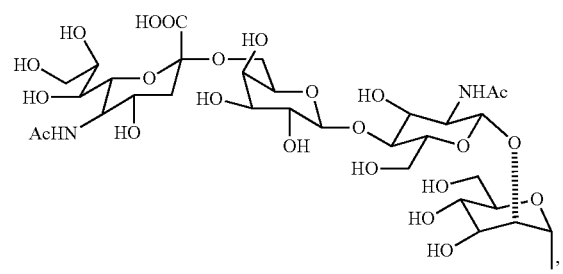

[Formula 4]

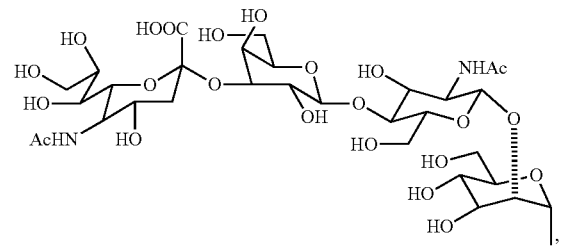

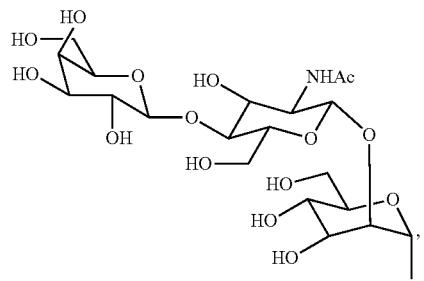

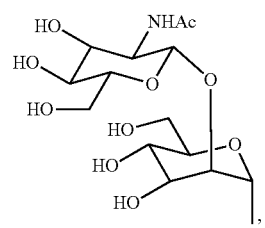

and

Ac represents an acetyl group.

In the oligosaccharide chain added GLP-1 peptide of the present invention, the oligosaccharide chain may exist in vivo in a form of complex carbohydrate or may be bound to the GLP-1 peptide in a manner other than O-linkage and N-linkage. For example, oligosaccharide chain added GLP-1 peptides wherein the oligosaccharide chain is linked to Cys or Lys via a linker, as described above, are also incorporated in the oligosaccharide chain added GLP-1 peptide of the present invention.

In a preferable aspect of the present invention, the oligosaccharide chain is relatively low-molecular-weight glycosaminoglycan including hyaluronic acid, chondroitin, chondroitin sulfates A to C, heparin, heparan sulfate and keratan sulfate. These oligosaccharide chains have linearly linked repeats of disaccharide units consisting of an amino sugar (N-acetylglucosamine or N-acetylgalactosamine) and uronic acid (glucuronic acid or L-iduronic acid). The relatively low-molecular-weight glycosaminoglycan used herein means that, for example, the molecular weight is about 10 kDa or lower, preferably about 6 kDa or lower, more preferably about 4 kDa or lower or the number of sugars therein is about 50 or less, preferably 30 or less, more preferably 20 or less.

In one aspect of the present invention, the oligosaccharide chain in the oligosaccharide chain added GLP-1 peptide of the present invention is preferably an oligosaccharide chain consisting of four or more sugars, e.g., five or more, seven or more, particularly, nine or more or eleven or more sugars.

In a preferable aspect of the present invention, the oligosaccharide chain in the oligosaccharide chain added GLP-1 peptide of the present invention consists of five to eleven, nine to eleven or eleven sugars.

In a preferable aspect of the present invention, the oligosaccharide chain in the oligosaccharide chain added GLP-1 peptide of the present invention is a biantennary complex-type oligosaccharide chain. The complex-type oligosaccharide chain is characterized by comprising two or more types of monosaccharides and having the following basic structure and a lactosamine structure represented by Galβ1-4GlcNAc:

[Formula 5]

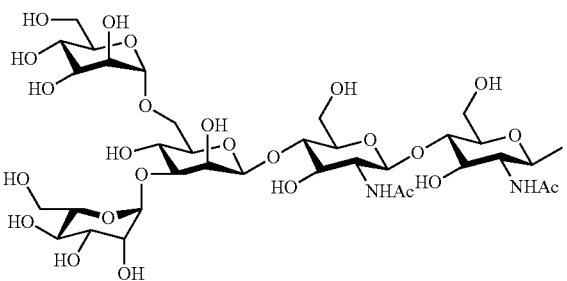

The biantennary complex-type oligosaccharide chain refers to those wherein a monoantenna oligosaccharide chain consisting of 0 to 3 sugars is linked to each of two terminal mannoses of the basic structure. The biantennary complex-type oligosaccharide chain is preferably, for example, the following disialo oligosaccharide chain:

[Formula 6]

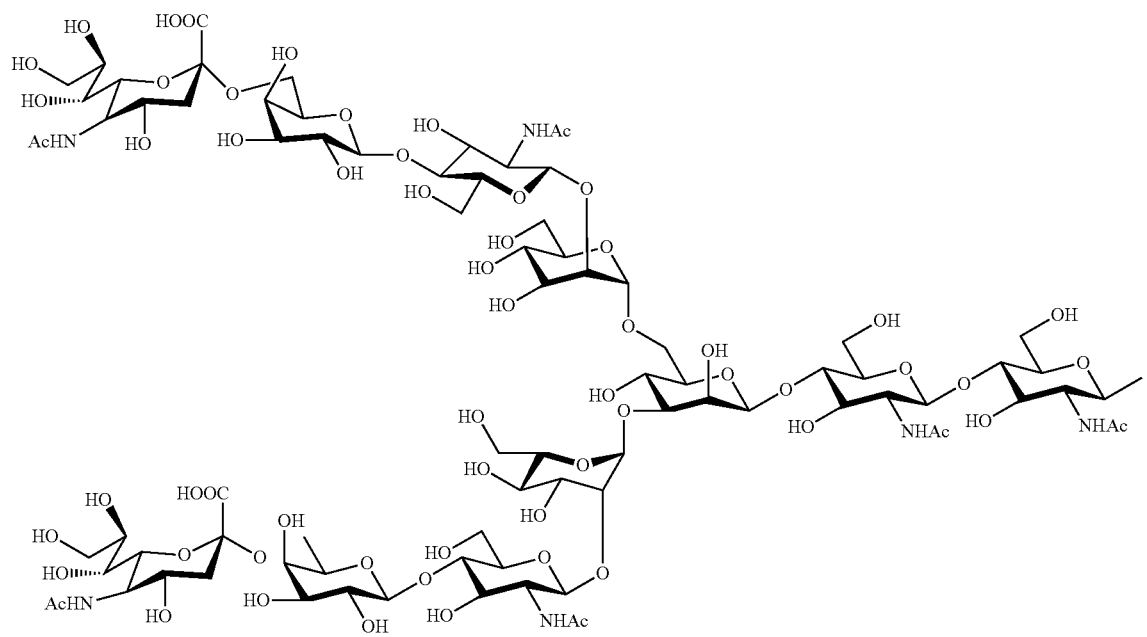

the monosialo oligosaccharide chain:
[Formula 7]
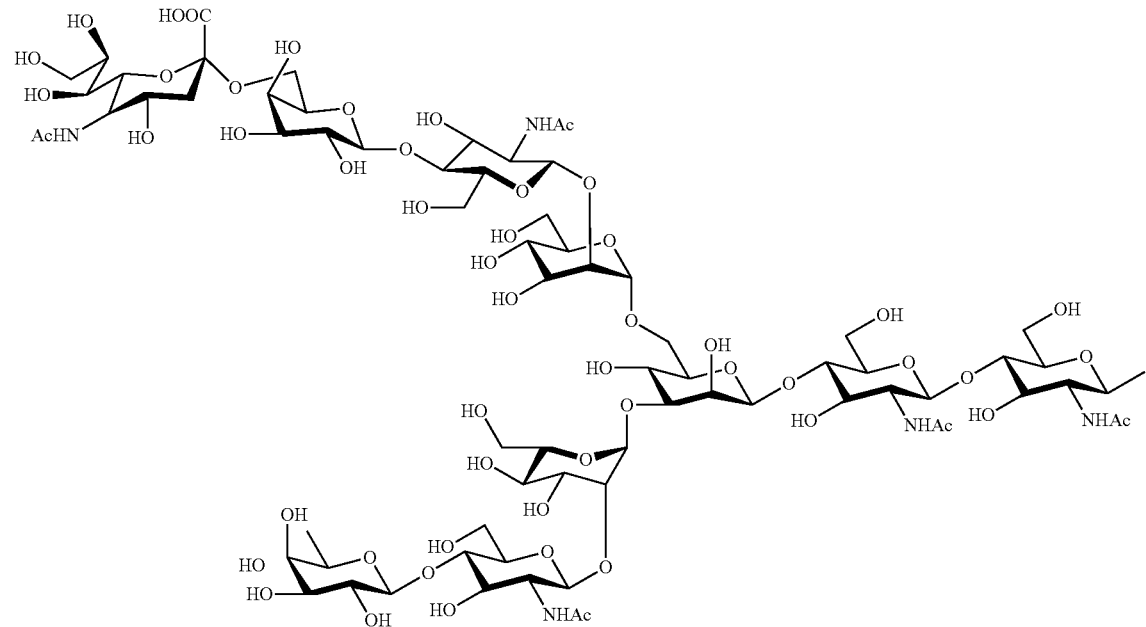
the asialo oligosaccharide chain:
[Formula 8]
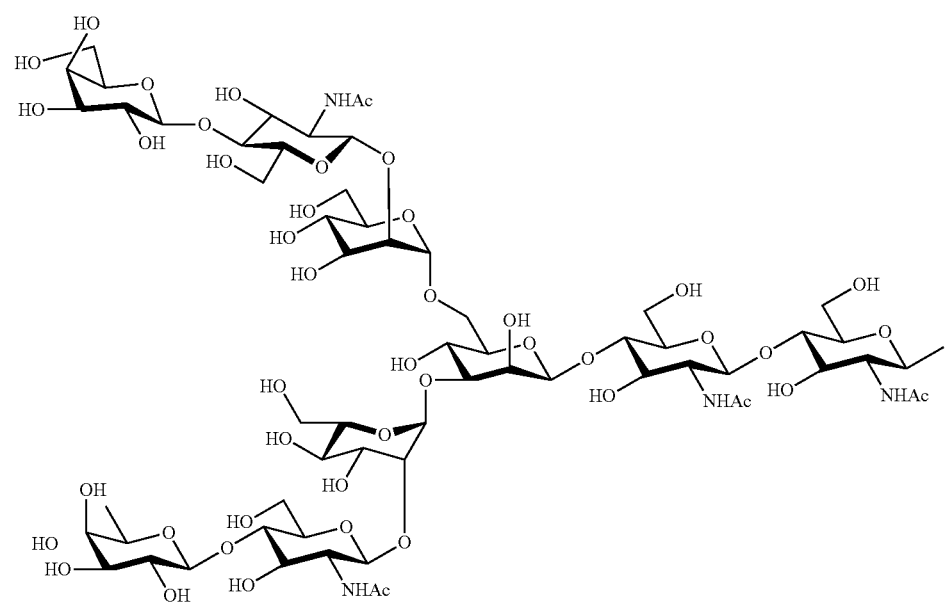

the diGlcNAc oligosaccharide chain:

[Formula 9]

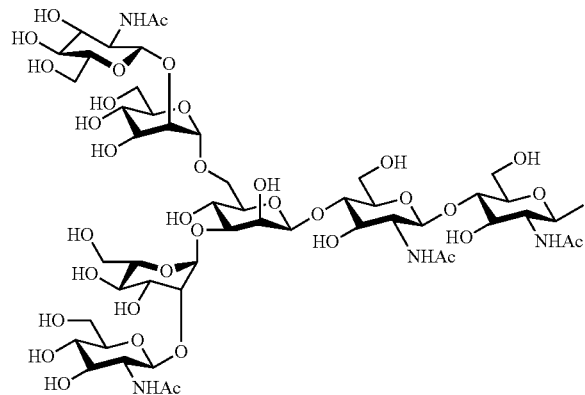

the dimannose oligosaccharide chain:

[Formula 10]

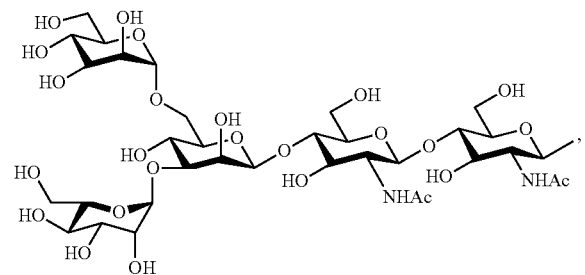

etc.

The disialo oligosaccharide chain is more preferable.

The "disialo oligosaccharide chain", the "monosialo oligosaccharide chain", the "asialo oligosaccharide chain", the "diGlcNAc oligosaccharide chain", and the "dimannose oligosaccharide chain" used herein also encompass, in addition to those shown above by the chemical formulas, oligosaccharide chains having patterns of linkages different from those shown in the chemical formulas. Such an oligosaccharide chain is also preferably used as the oligosaccharide chain of the present invention. Examples of such an oligosaccharide chain include a disialo oligosaccharide chain or asialo oligosaccharide chain wherein sialic acid is linked to galactose via ($\alpha 2 \rightarrow \alpha 3$) linkage.

The high-mannose type oligosaccharide chain used in the present invention is an oligosaccharide chain wherein two or more mannoses are further linked to the basic structure of the complex-type oligosaccharide chain. Since the high-mannose type oligosaccharide chain is bulky, the binding of the high-mannose type oligosaccharide chain to the peptide can more highly enhance stability in blood. An oligosaccharide chain containing 5 to 9 mannoses, such as a mammalian high-mannose type oligosaccharide chain, is preferable. An oligosaccharide chain containing more mannoses, such as a yeast high-mannose type oligosaccharide chain, may be used. Examples of high-mannose type oligosaccharide chains preferably used in the present invention may include:

the high mannose-5 (M-5):

[Formula 11]

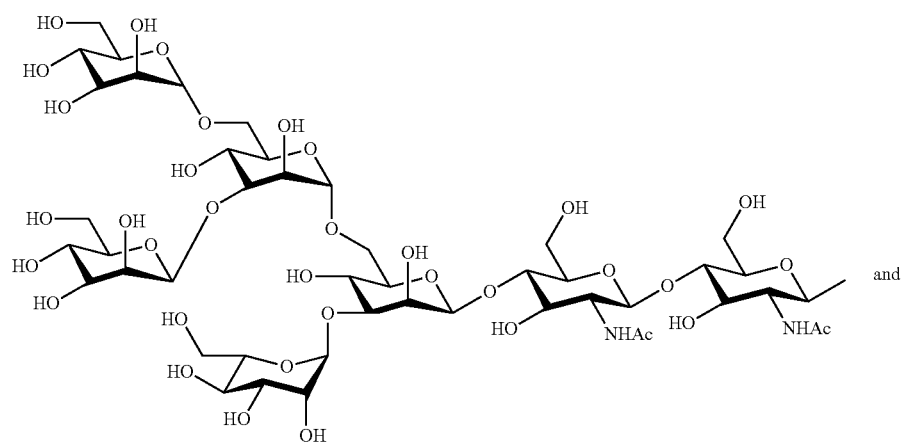

the high mannose-9 (M-9)

[Formula 12]

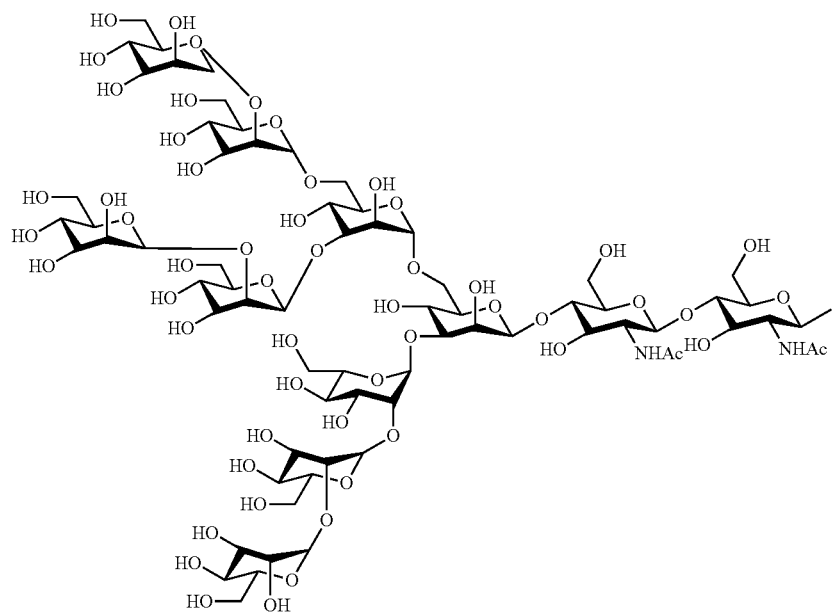

In the present invention, examples of preferable oligosaccharide chains may include oligosaccharide chains structurally the same as (oligosaccharide chains having the same types of constituent sugars and the same patterns of linkages of the sugars) oligosaccharide chains which are bound to a protein to form a glycoprotein in human bodies (e.g., oligosaccharide chains described in "FEBS LETTERS Vol. 50, No. 3, February 1975"), or oligosaccharide chains lacking one or several sugars from the nonreducing end thereof, which are described in Tables 1 to 4 below.

TABLE 1

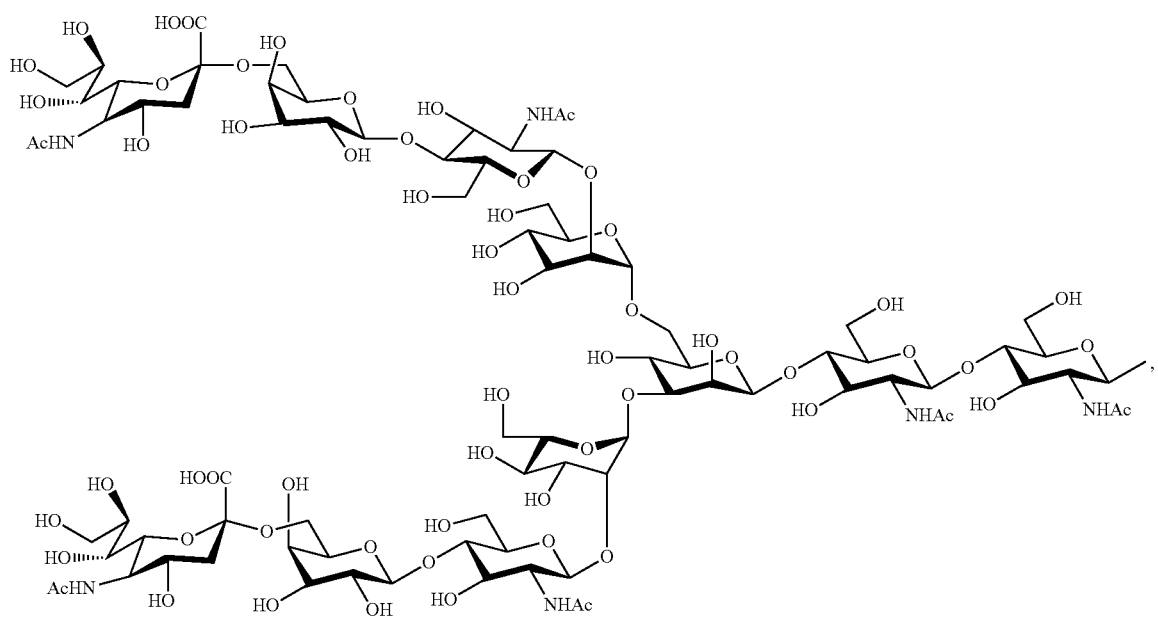

IS2S-11NC, 1

TABLE 1-continued
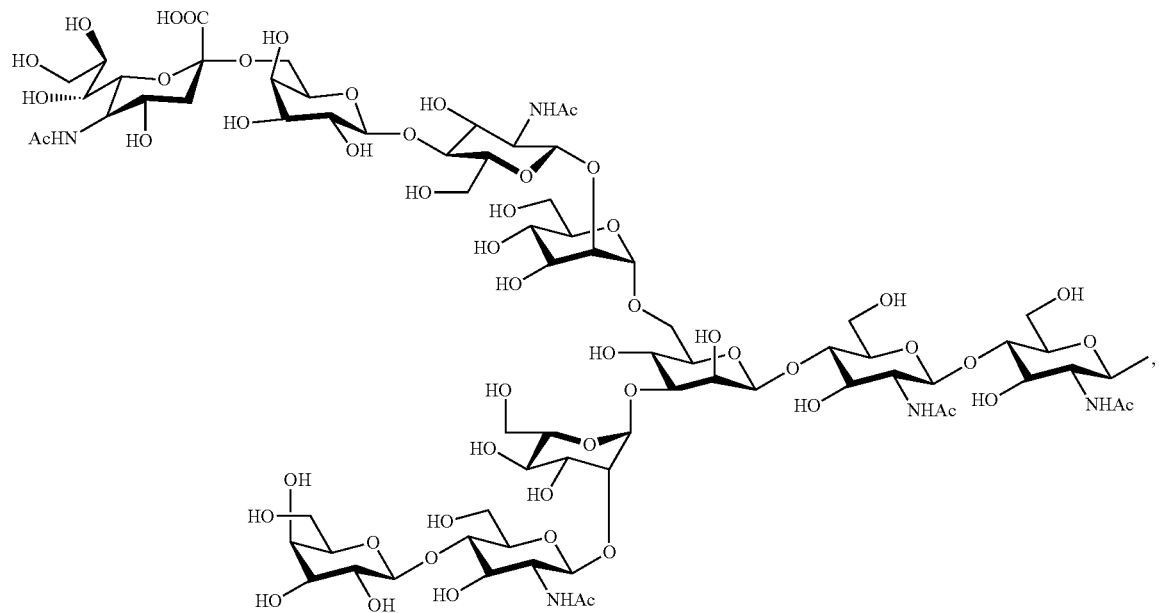
IS2G-10NC, 2
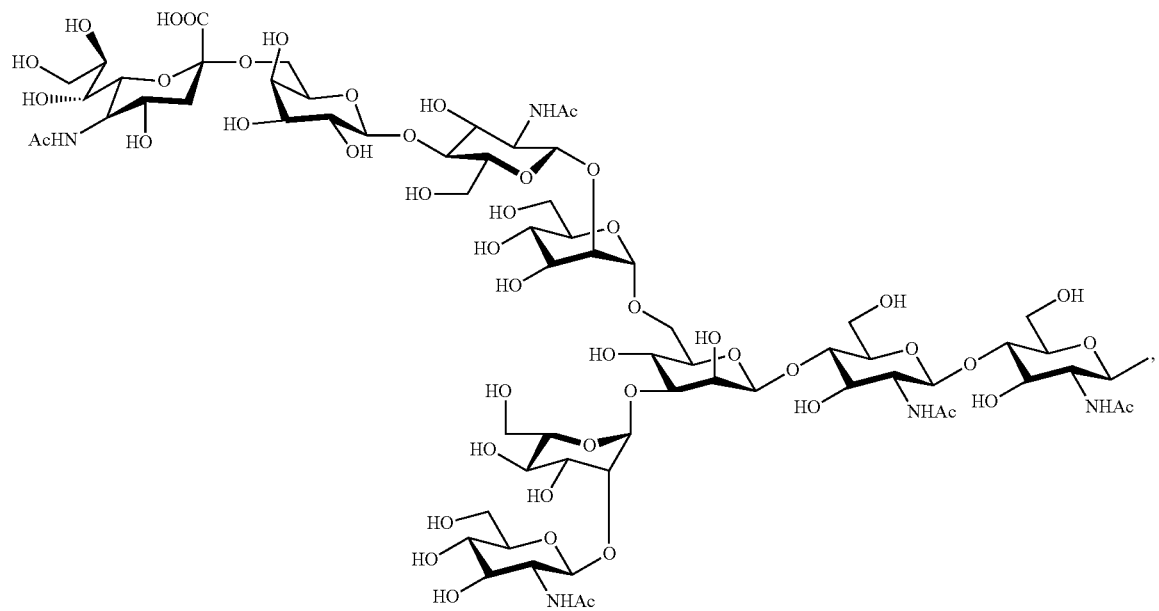
1S2GN-9NC, 3

TABLE 1-continued
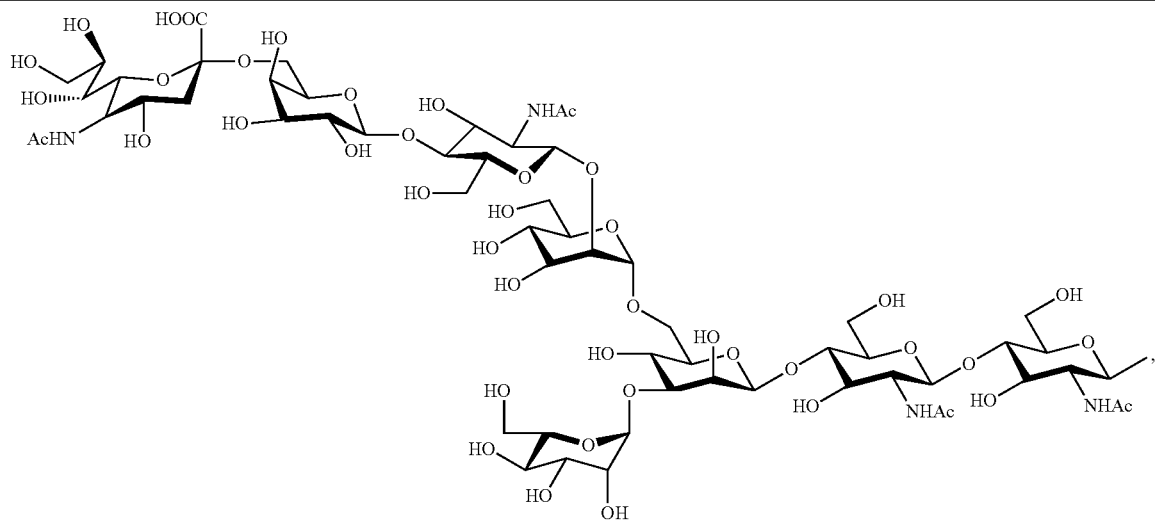
1S2M-8NC, 4
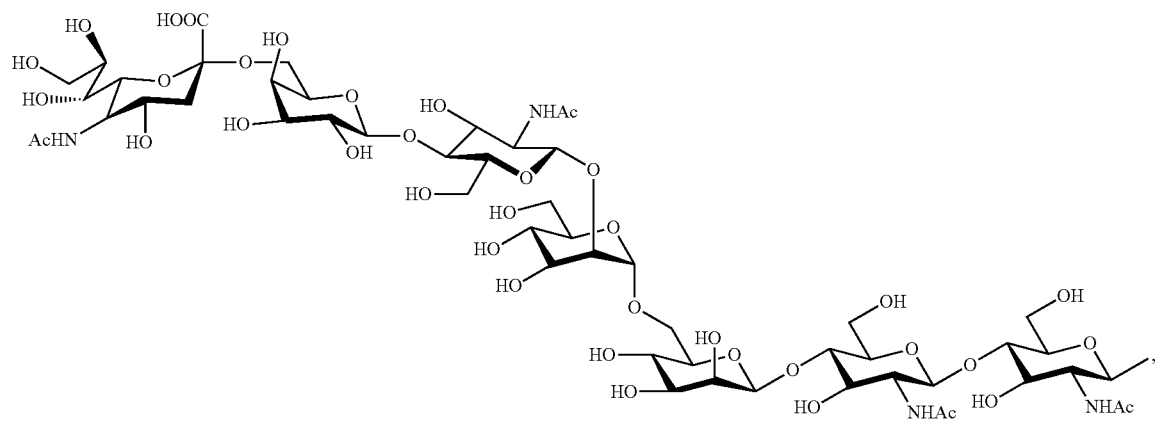
1S-7NC, 5
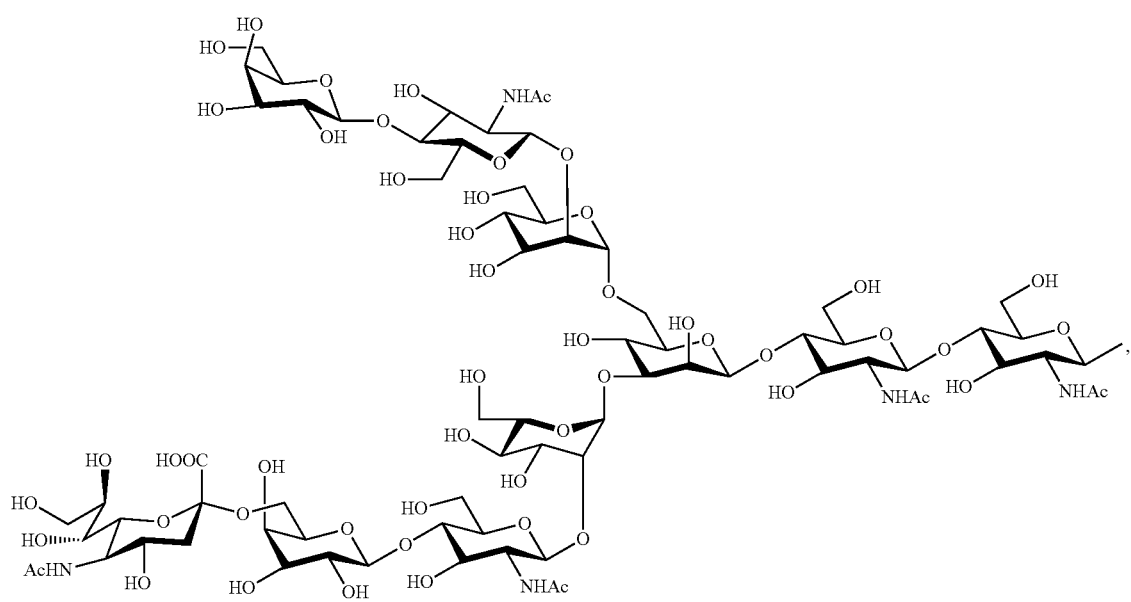
1G2S-10NC, 6

TABLE 1-continued
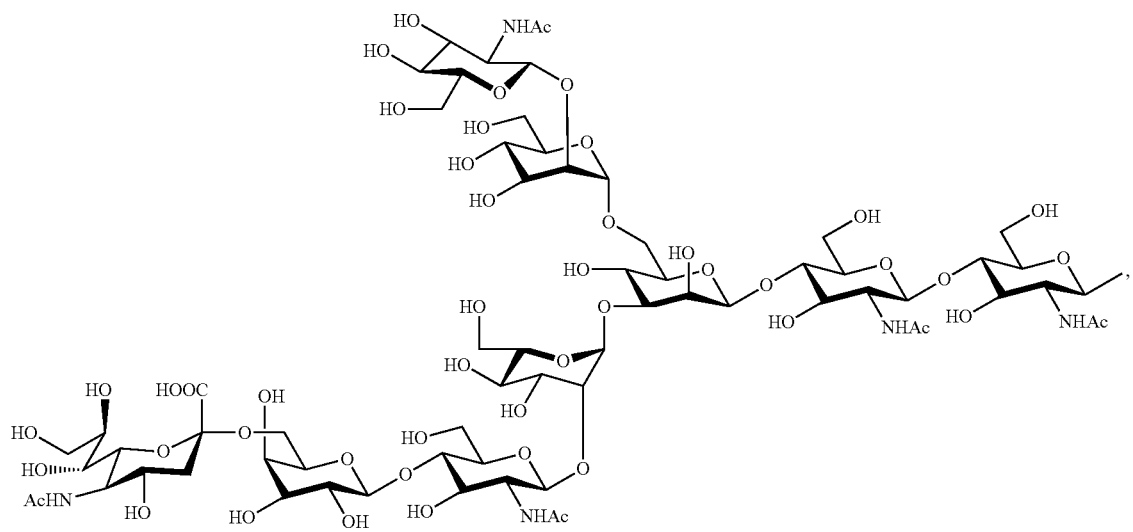
1GN2S-9NC, 7
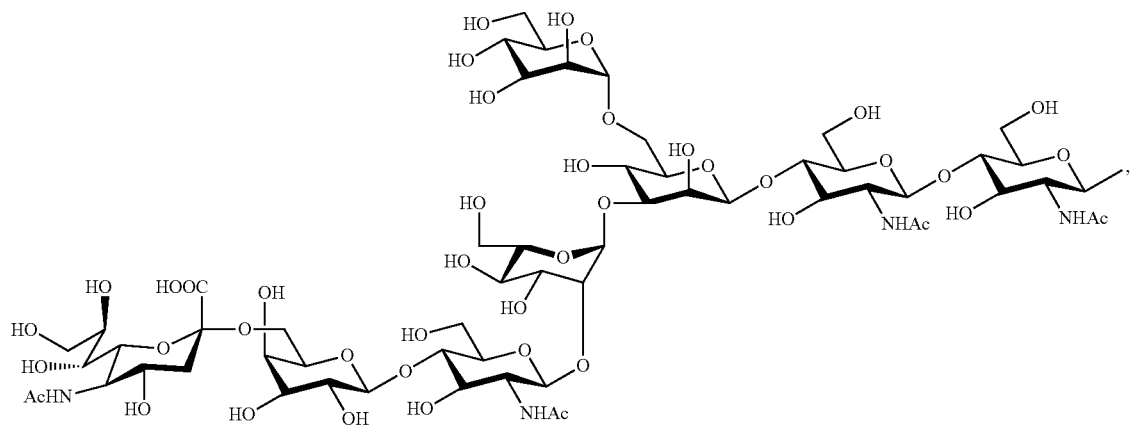
1M2S-8NC, 8
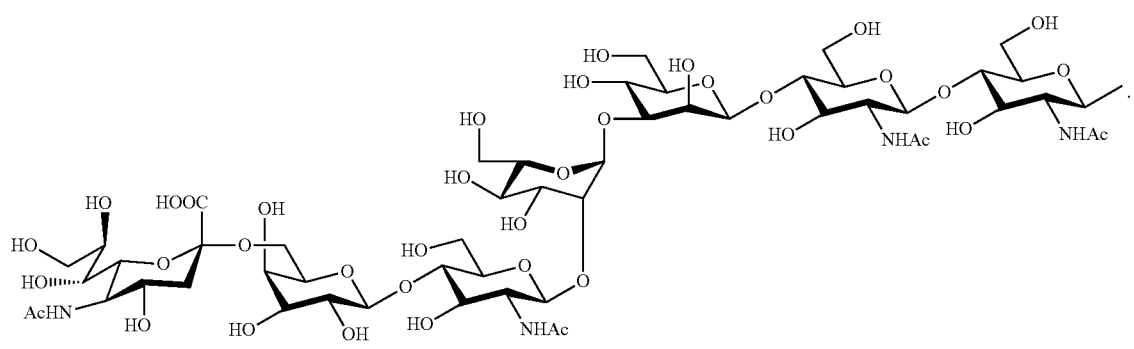
2S-7NC, 9

TABLE 2
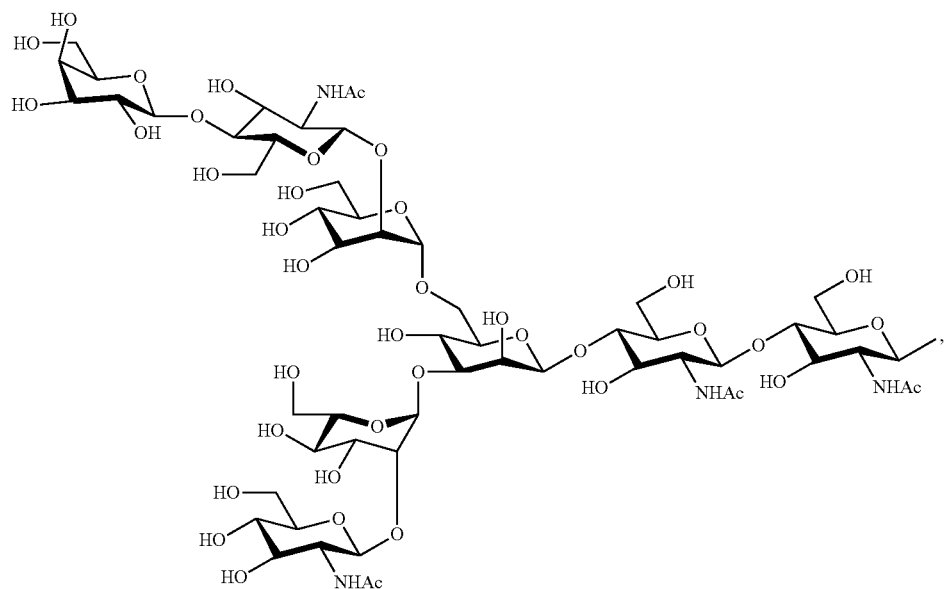
1G2GN-8NC, 10
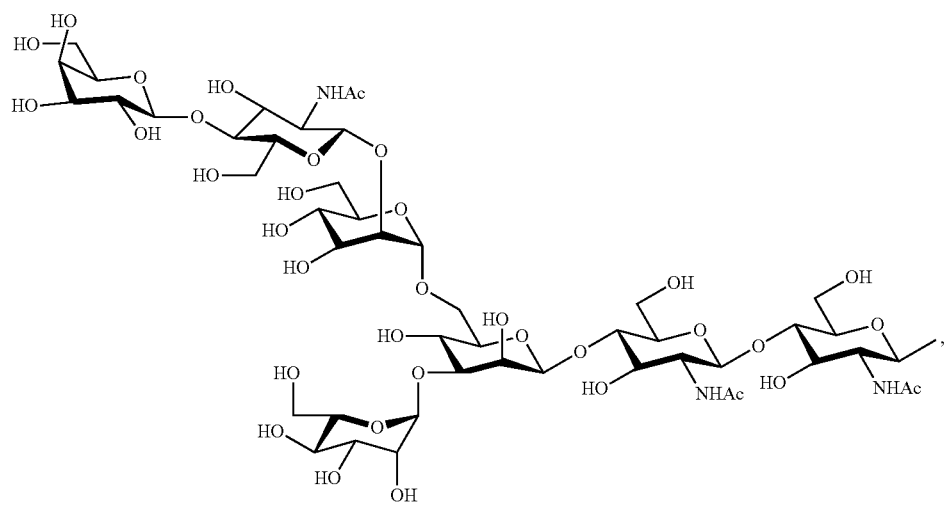
1G2M-7NC, 11
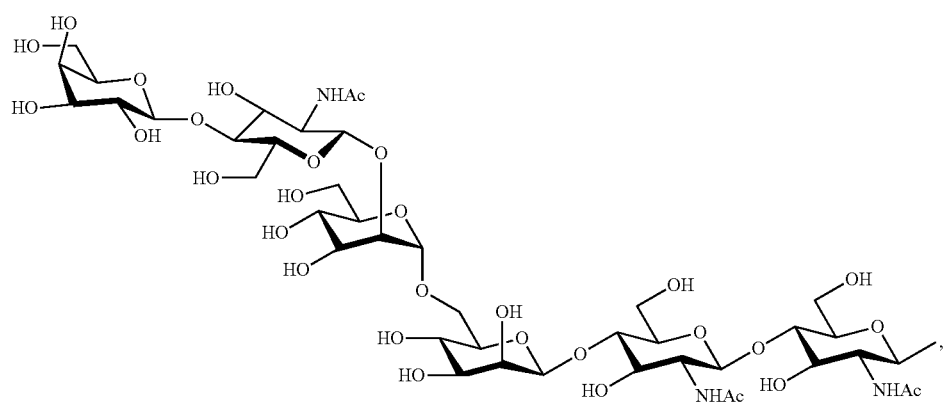
1G-6NC, 12

TABLE 2-continued
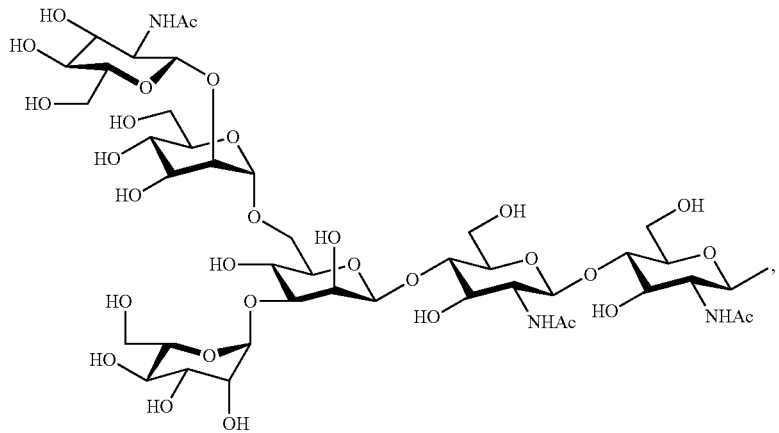
1GN2M-6NC, 13
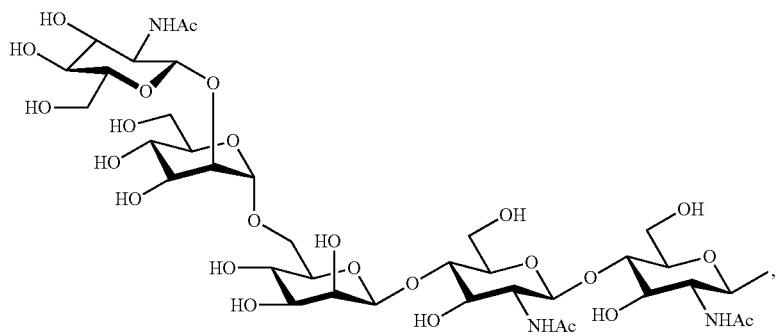
1GN-5NC, 14
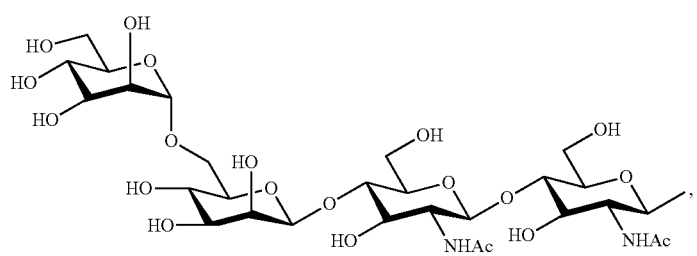
1M-4NC, 15

TABLE 2-continued
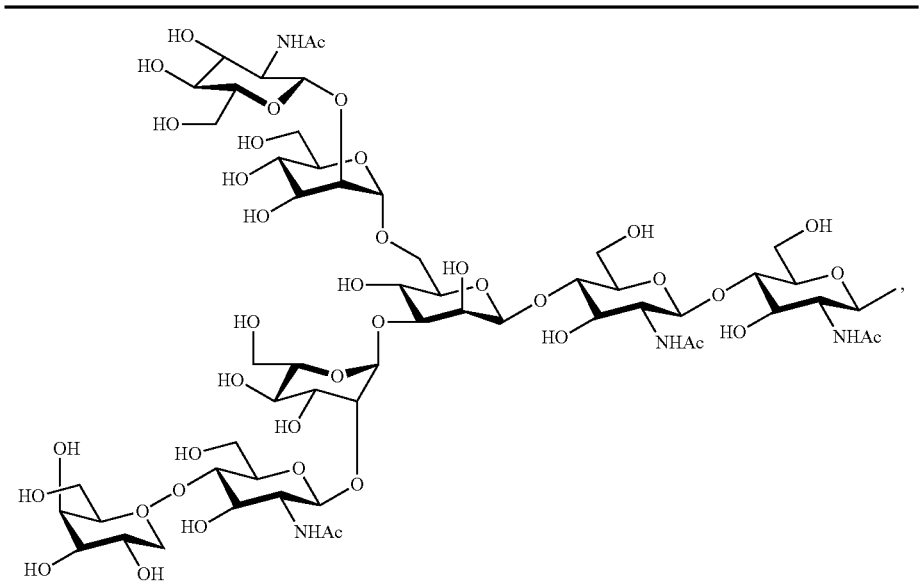
1GN2G-8NC, 16
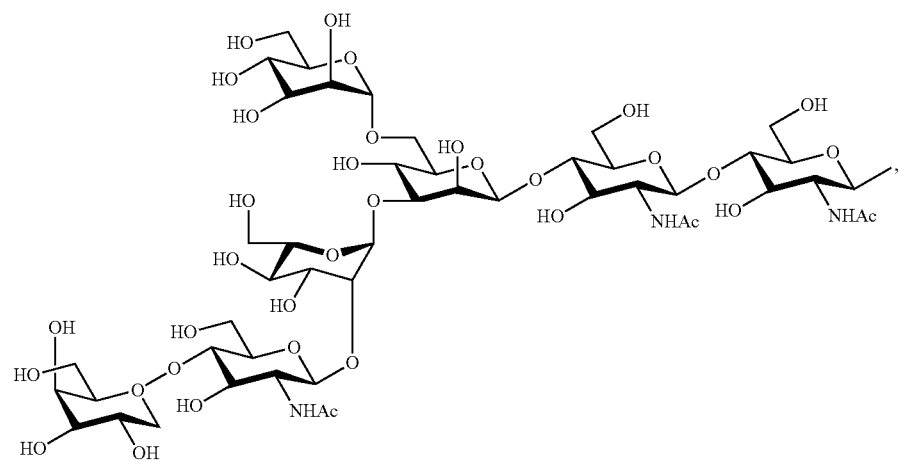
1M2G-7NC, 17
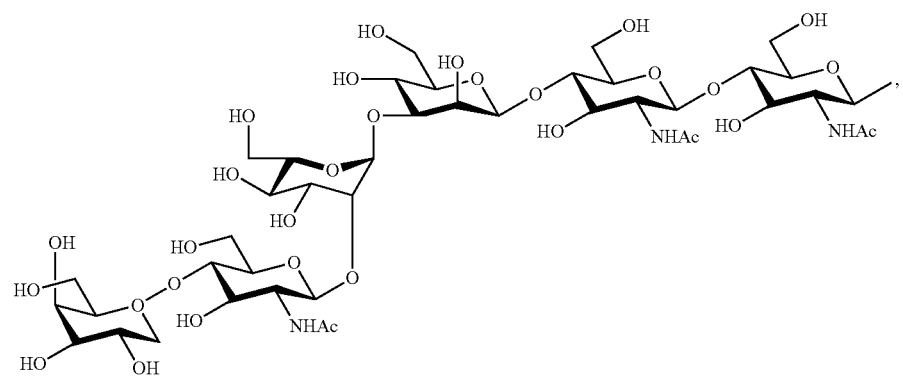
2G-6NC, 18

TABLE 2-continued
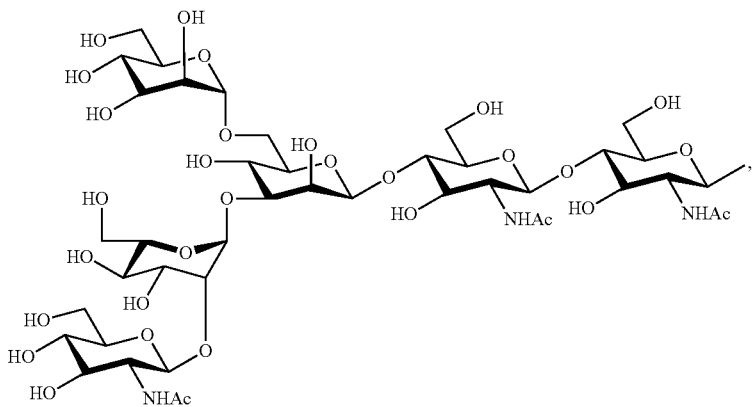
1M2GN-5NC, 19
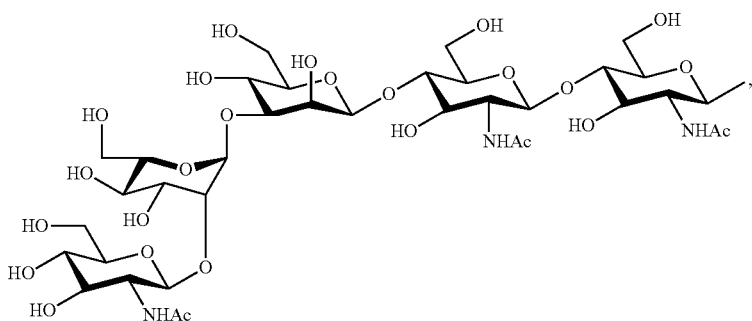
2GN-5NC, 20
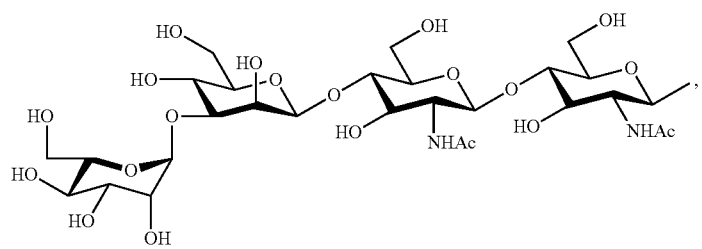
2M-4NC, 21

TABLE 2-continued
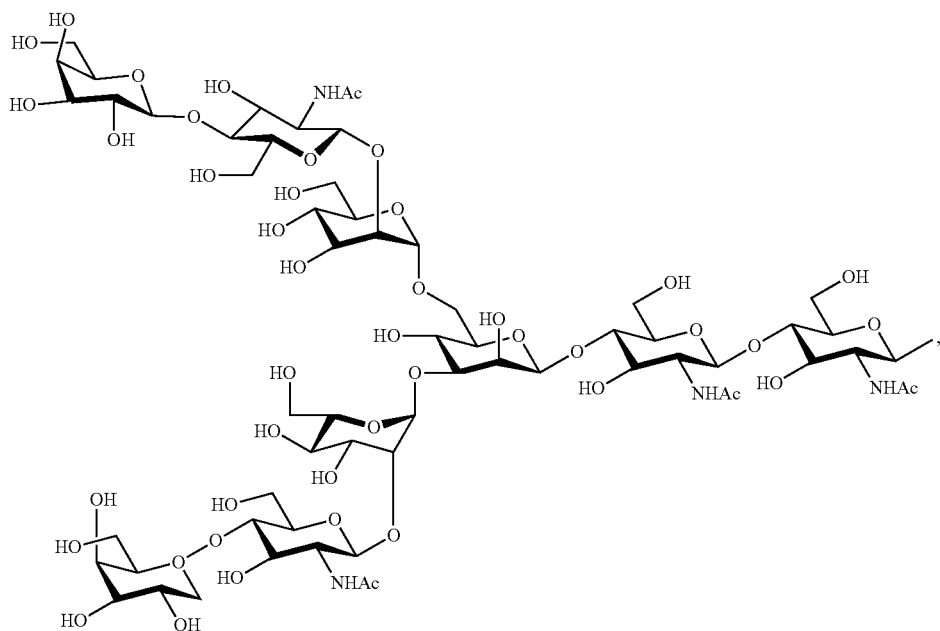
1G2G-9NC, 22
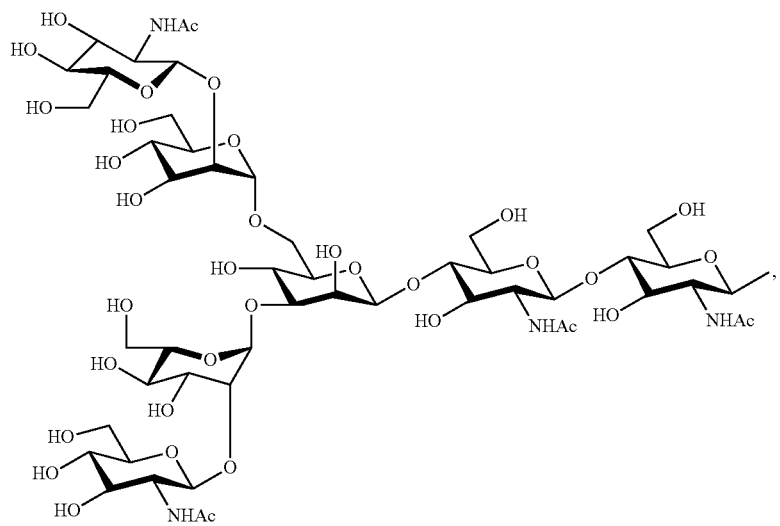
1GN2GN-7NC, 23
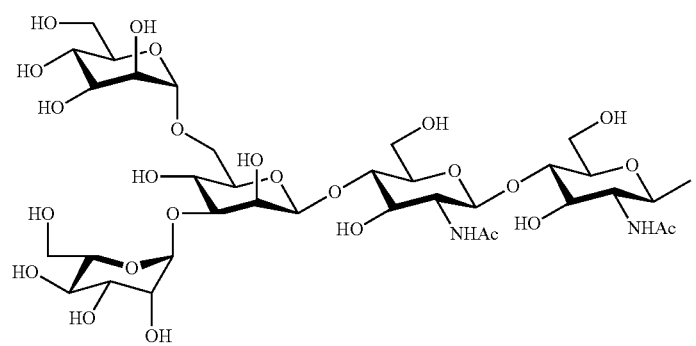
1M2M-5NC, 24

TABLE 3
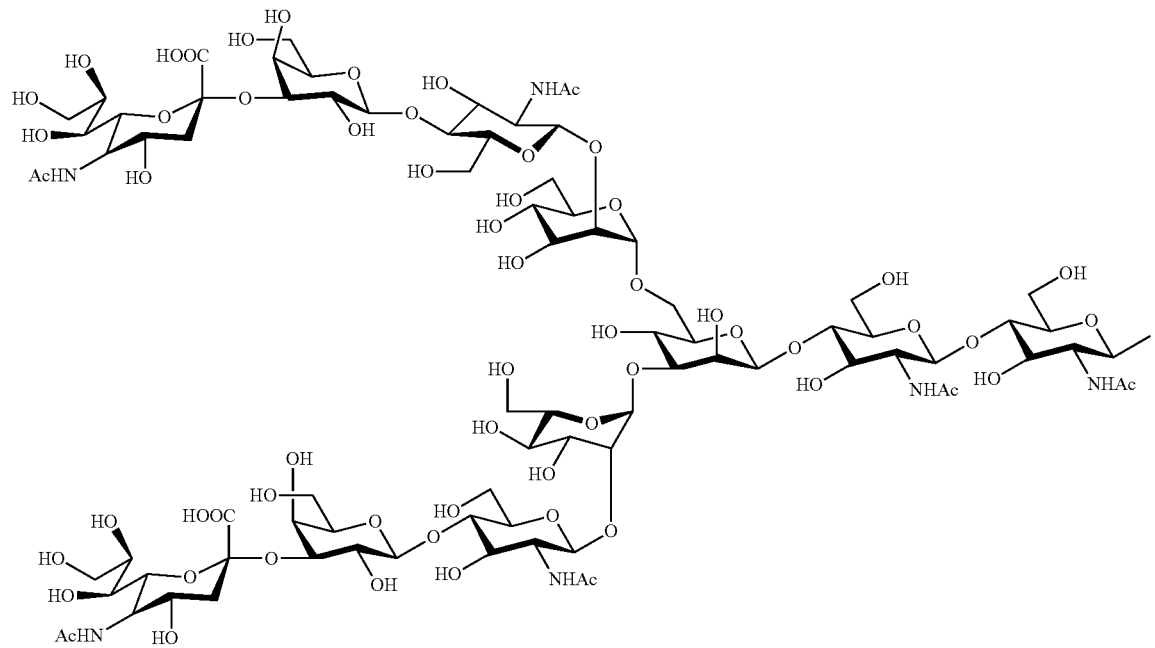
1S(3)2S(3)-11NC, 25
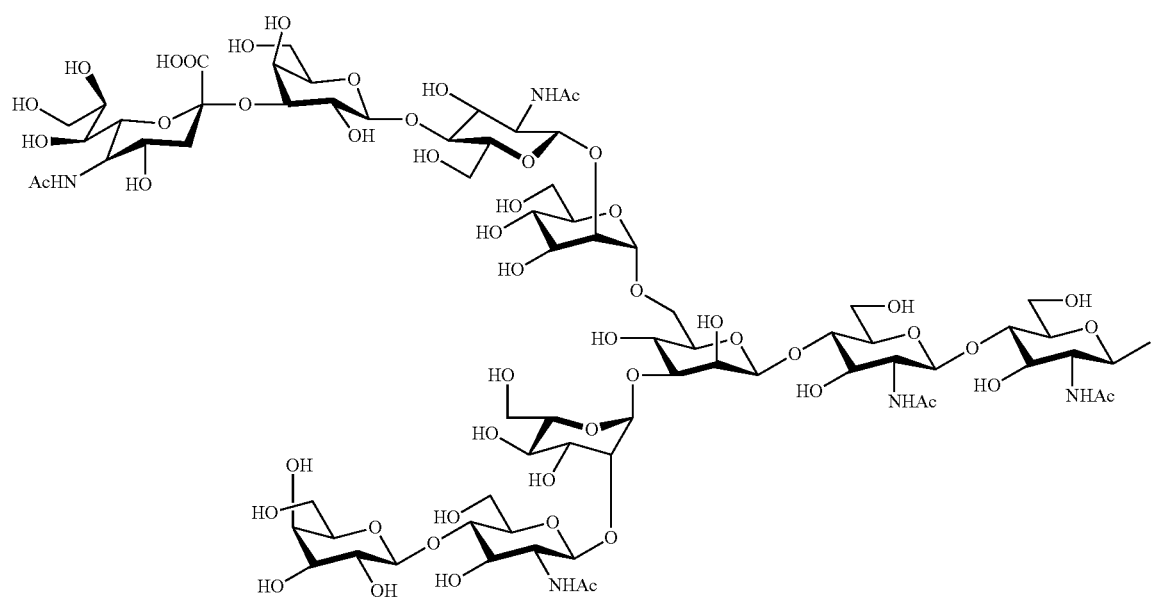
1S(3)2G-10NC, 26

TABLE 3-continued
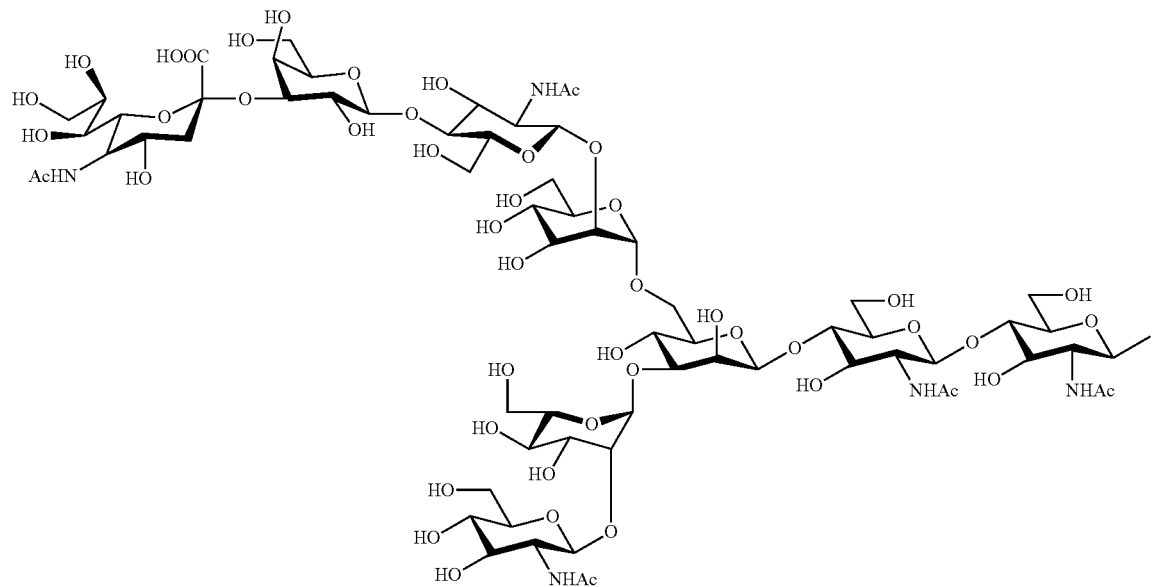
1S(3)2GN-9NC, 27
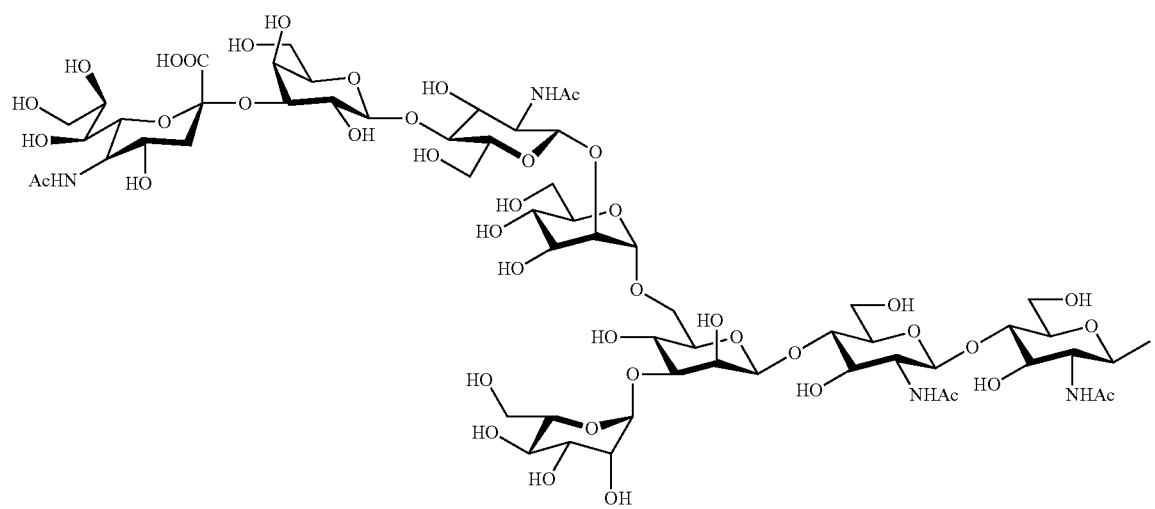
1S(3)2M-8NC, 28

TABLE 3-continued
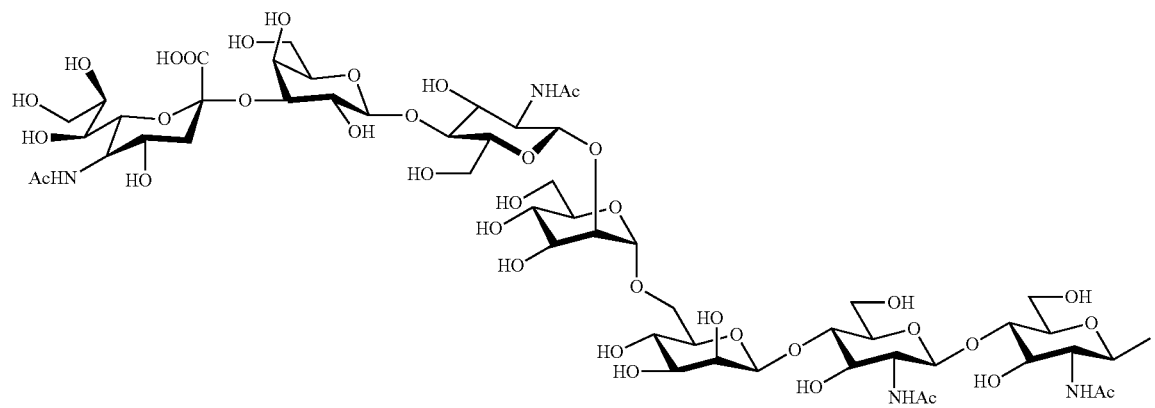
1S(3)-7NC, 29
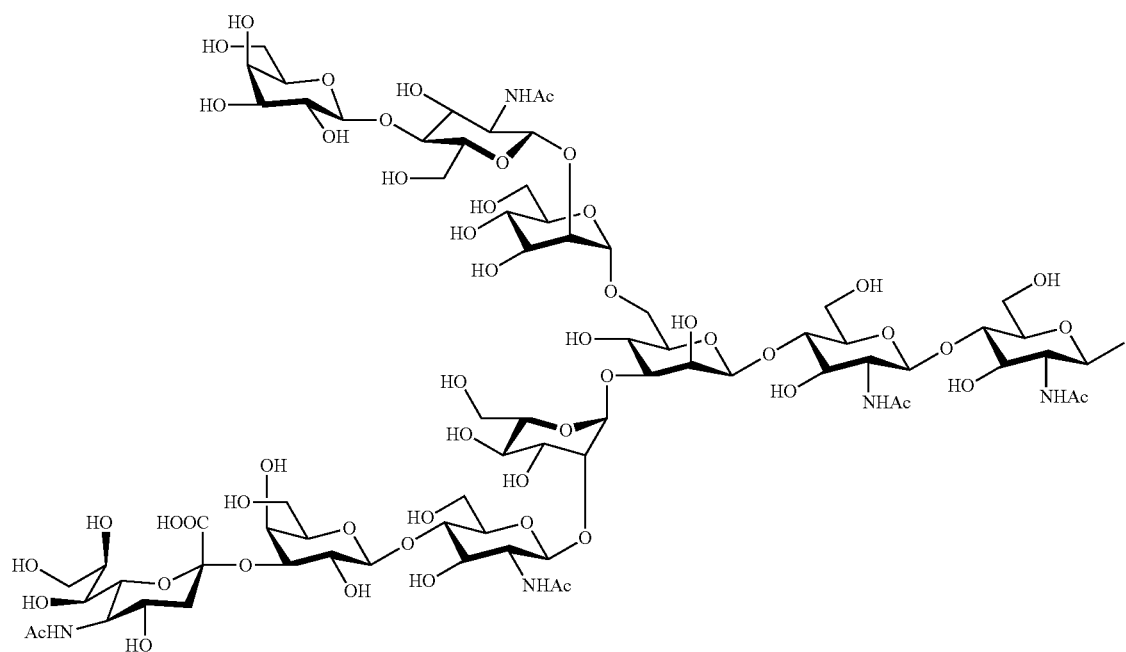
1G2S(3)-10NC, 30

TABLE 3-continued
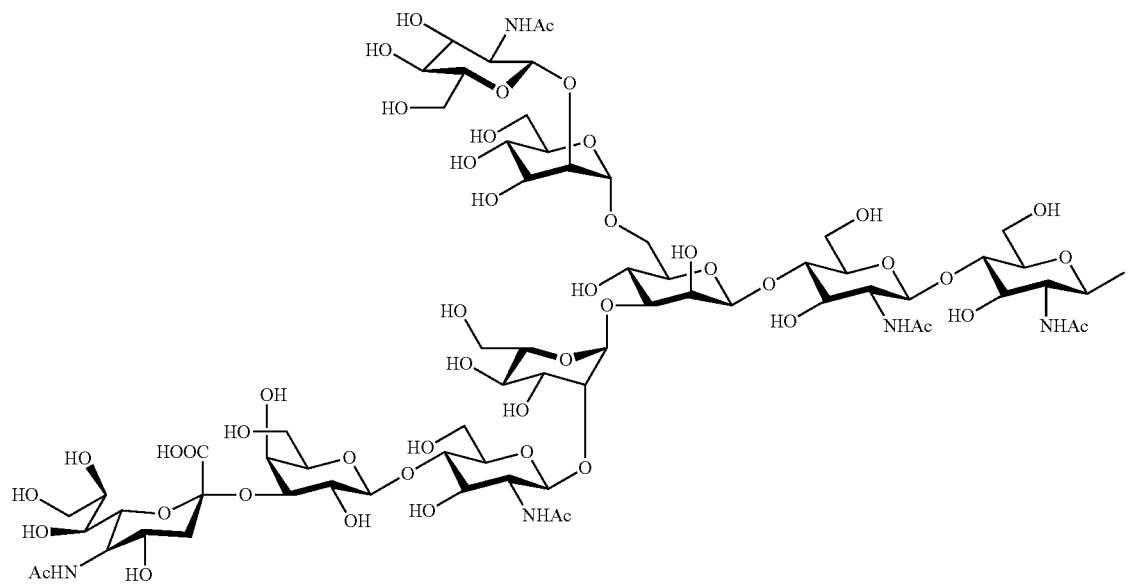
1GN2S(3)-9NC, 31
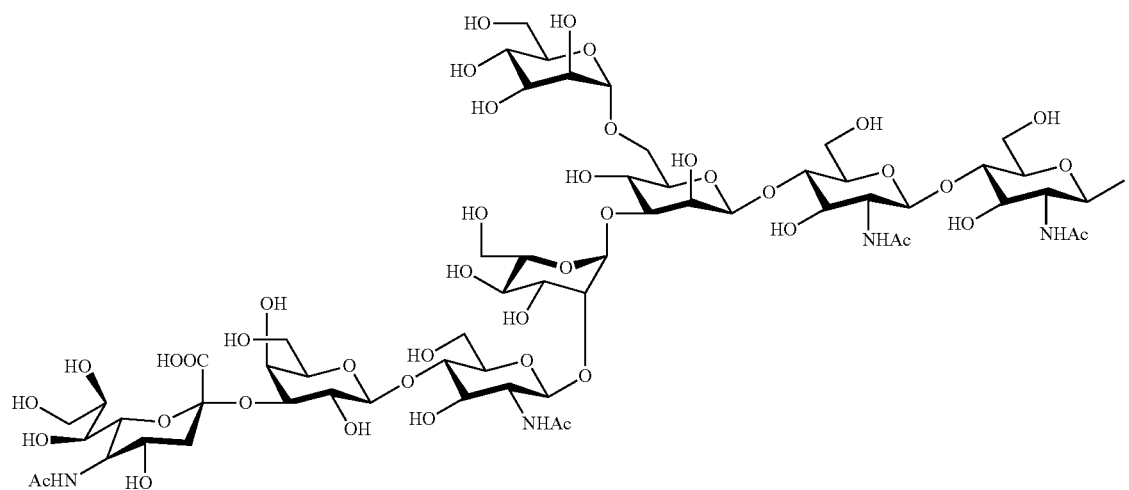
1M2S(3)-8NC, 32
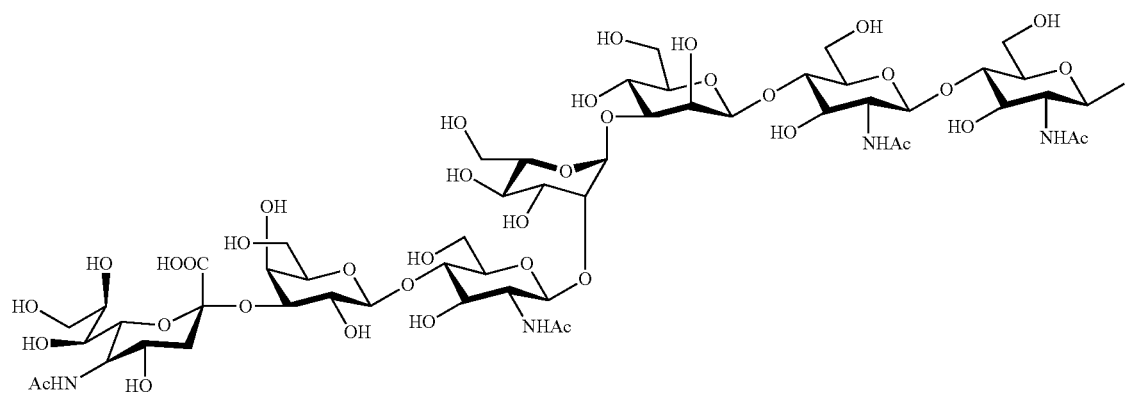
2S(3)-7NC, 33

TABLE 4
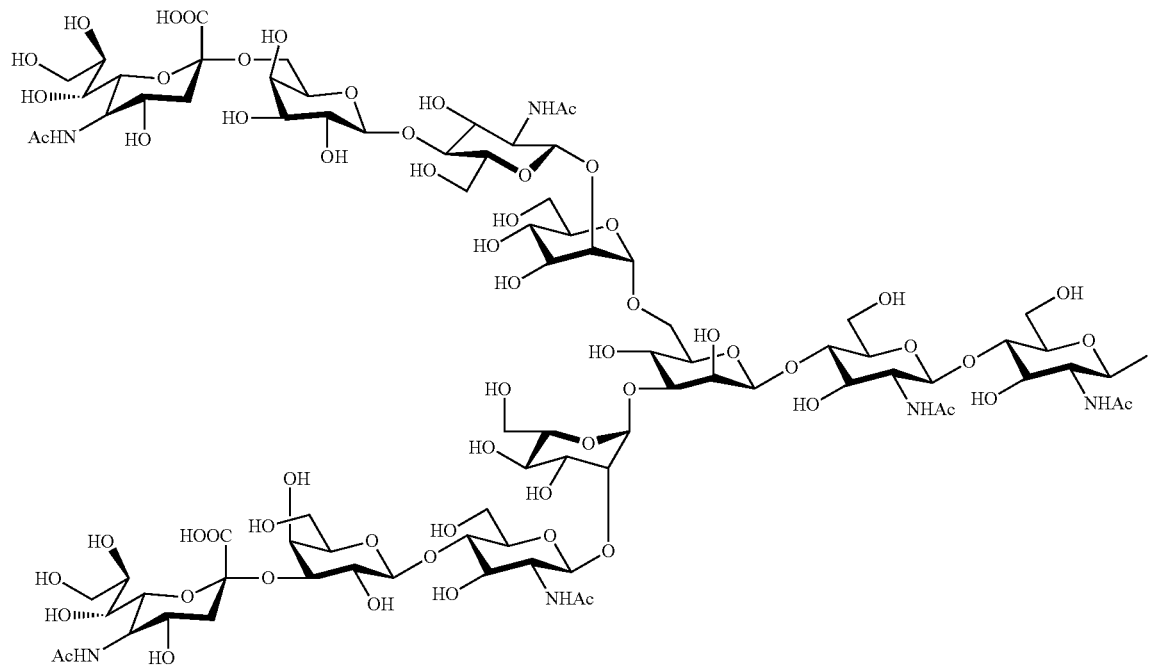
1S2S(3)-11NC, 34
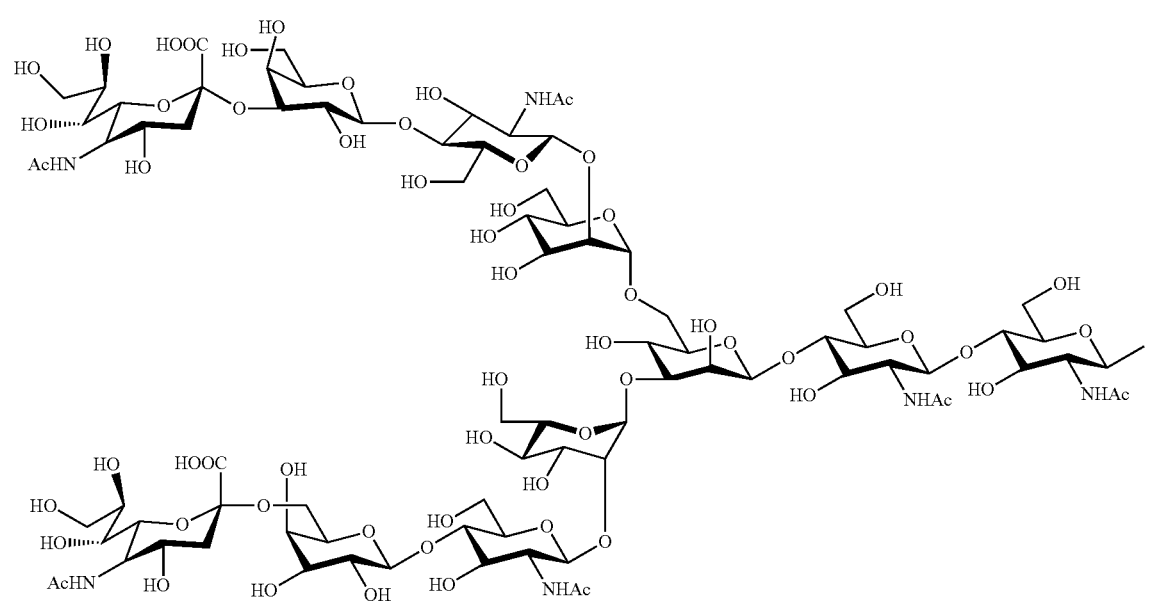
1S(3)2S-11NC, 35

In one aspect of the present invention, the oligosaccharide chain is preferably an oligosaccharide chain having a linear structure. Examples of such an oligosaccharide chain include oligo hyaluronic acid. The oligo hyaluronic acid used herein refers to an oligosaccharide chain wherein N-acetylglucosamine and glucuronic acid are alternately linked linearly to form di to dotriacontasaccharide, preferably di- to hexadecasaccharide, more preferably tetra- to octasaccharide.

Examples of particularly preferable oligo hyaluronic acid used in the present invention include an oligosaccharide chain having 2 (tetrasaccharide) or more and 8 (hexadecasaccharide) or less of units each consisting of N-acetylglucosamine and glucuronic acid. An oligosaccharide chain having 2 (tetrasaccharide) to 4 (octasaccharide) of the units is more preferable, and an oligosaccharide chain having 2 (tetrasaccharide) of the units is most preferable.

Examples of hyaluronic acids preferably used in the present invention include
oligo hyaluronic acid in the form of tetrasaccharide:

[Formula 13]

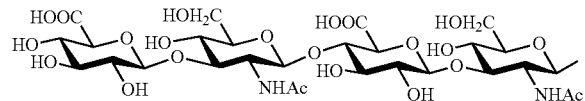

and
oligo hyaluronic acid in the form of octasaccharide:

[Formula 14]

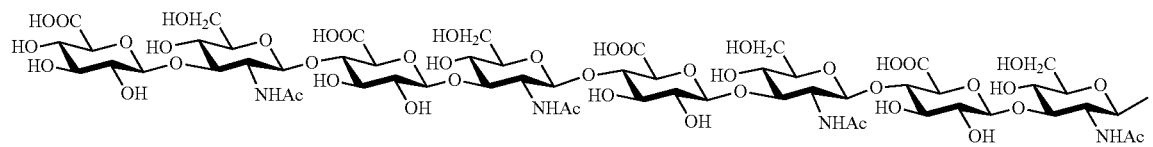

In a preferable aspect of the present invention, the glycopeptide of the present invention has a uniform oligosaccharide chain structure. The uniform oligosaccharide chain structure in the glycopeptide used herein refers to the same oligosaccharide chain added site in the peptide, the same type of each constituent sugar in the oligosaccharide chain, the same order wherein the sugars are linked, and the same pattern of linkages between the sugars, when compared among the glycopeptides, and means that the oligosaccharide chain structure has at least 90%, preferably at least 95%, more preferably at least 99% uniformity. The glycopeptides having a uniform oligosaccharide chain structure have constant quality and are particularly preferable in the field such as pharmaceutical production or assay. The proportion of uniform oligosaccharide chains can be measured by a method using, for example, HPLC, capillary electrophoresis, NMR, mass spectrometry, etc.

In the present invention, examples of preferable oligosaccharide chain added GLP-1 peptides may include oligosaccharide chain added GLP-1 peptides (SEQ ID NOs: 54 to 66) produced in Examples 1 to 15 described later, i.e., oligosaccharide chain added GLP-1 peptides having the sequence of
$His_7$-$Ala_8$-$Glu_9$-$Gly_{10}$-$Thr_{11}$-$Phe_{12}$-$Thr_{13}$-$Ser_{14}$-$Asp_{15}$-$Val_{16}$-$Ser_{17}$-$Ser_{18}$-$Tyr_{19}$-$Leu_{20}$-$Glu_{21}$-$Gly_{22}$-$Gln_{23}$-$Ala_{24}$-$Ala_{25}$-$Lys_{26}$-$Glu_{27}$-$Phe_{28}$-$Ile_{29}$-$Ala_{30}$-$Trp_{31}$-$Leu_{32}$-$Val_{33}$-$Lys_{34}$-$Gly_{35}$-$Arg_{36}$-$Gly_{37}$ (SEQ ID NO: 2, GLP-1) wherein:

(b1) 26Lys and 34Lys are each substituted with disialo oligosaccharide chain added Cys (Example 1) (SEQ ID NO: 54);

(b2) 18Ser and 36Arg are each substituted with disialo oligosaccharide chain added Cys (Example 2) (SEQ ID NO: 55);

(b3) 22Gly and 30Ala are each substituted with disialo oligosaccharide chain added Cys (Example 3) (SEQ ID NO: 56);

(b4) 22Gly and 36Arg are each substituted with disialo oligosaccharide chain added Cys (Example 4) (SEQ ID NO: 57);

(b5) 30Ala and 36Arg are each substituted with disialo oligosaccharide chain added Cys (Example 5) (SEQ ID NO: 58);

(b6) 30Ala is substituted with oligo hyaluronic acid tetrasaccharide (HA-4) added Cys (Example 6) (SEQ ID NO: 59);

(b7) 30Ala is substituted with oligo hyaluronic acid octasaccharide (HA-8) added Cys (Example 7) (SEQ ID NO: 60);

(b8) 36Arg is substituted with oligo hyaluronic acid tetrasaccharide (HA-4) added Cys (Example 8) (SEQ ID NO: 61);

(b9) 36Arg is substituted with oligo hyaluronic acid octasaccharide (HA-8) added Cys (Example 9) (SEQ ID NO: 62);

(b10) 30Ala is substituted with oligo hyaluronic acid hexadecasaccharide (HA-16) added Cys (Example 10) (SEQ ID NO: 63);

(b11) 36Arg is substituted with oligo hyaluronic acid hexadecasaccharide (HA-16) added Cys (Example 11) (SEQ ID NO: 64);

(b12) 36Arg is substituted with high-mannose type oligosaccharide chain (M5) added Cys (Example 12) (SEQ ID NO: 65); and (b13) asialo oligosaccharide chain added Asn is linked to 26Lys via a linker (Example 13) (SEQ ID NO: 66), and further include:

(b14) an oligosaccharide chain added GLP-1 peptide having the sequence of
$H$-$His_1$-$Gly_2$-$Glu_3$-$Gly_4$-$Thr_5$-$Phe_6$-$Thr_7$-$Ser_8$-$Asp_9$-$Leu_{10}$-$Ser_{11}$-$Lys_{12}$-$Gln_{13}$-$Met_{14}$-$Glu_{15}$-$Glu_{16}$-$Glu_{17}$-$Ala_{18}$-$Val_{19}$-$Arg_{20}$-$Leu_{21}$-$Phe_{22}$-$Ile_{23}$-$Glu_{24}$-$Trp_{25}$-$Leu_{26}$-$Lys_{27}$-$Asn_{28}$-$Gly_{29}$-$Gly_{30}$-$Pr_{31}$-$Ser_{32}$-$Ser_{33}$-$Gly_{34}$-$Ala_{35}$-$Pro_{36}$-$Pro_{37}$-$Pro_{38}$-$Ser_{39}$-$NH_2$ (SEQ ID NO: 50, exendin-4) wherein
30Gly is substituted with disialo oligosaccharide chain added Cys (Example 14) (SEQ ID NO: 67);

(b15) an oligosaccharide chain added GLP-1 peptide having the sequence of
$His_7$-$R2_8$-$Glu_9$-$Gly_{10}$-$Thr_{11}$-$Phe_{12}$-$Thr_{13}$-$Ser_{14}$-$Asp_{15}$-$Val_{16}$-$Ser_{17}$-$Ser_{18}$-$Tyr_{19}$-$Leu_{20}$-$Glu_{21}$-$Gly_{22}$-$Gln_{23}$-$Ala_{24}$-$Ala_{25}$-$Lys_{26}$-$Glu_{27}$-$Phe_{28}$-$Ile_{29}$-$Ala_{30}$-$Trp_{31}$-$Leu_{32}$-$Val_{33}$-$Lys_{34}$-$R2_{35}$-$Arg_{36}$-$NH_2$ wherein R2 represents α-methylalanine (SEQ ID NO: 52, BIM51077) wherein
26Lys is substituted with disialo oligosaccharide chain added Cys (Example 15) (SEQ ID NO: 68); and (b16) an oligosaccharide chain added GLP-1 peptide having the sequence of exendin-4 (SEQ ID NO: 50) wherein 30Gly is substituted with high-mannose type oligosaccharide chain (M5) added Cys (Example 16).

The oligosaccharide chain added GLP-1 peptide of the present invention can be produced by incorporating an oligosaccharide chain addition step to a peptide synthesis method known by those skilled in the art. For oligosaccharide chain addition, a method using reverse reaction of an enzyme typified by transglutaminase is also usable. However, this method presents problems such as a large amount of necessary oligosaccharide chains to be added, complicated purification after the final step, limited sites to which oligosaccharide chain is added, and limited types of oligosaccharide chains that can be added. Therefore, the method is not practical for large-scale production such as pharmaceutical production, though it may be used in synthesis in small amounts, e.g., for assay use.

A process for conveniently producing the oligosaccharide GLP-1 peptide of the present invention and for stably producing oligosaccharide chain added GLP-1 peptides having a uniform oligosaccharide chain structure is specifically exemplified below by a process for producing an oligosaccharide chain added GLP-1 peptide by using oligosaccharide chain added Asn as an oligosaccharide chain added amino acid and utilizing a peptide synthesis method known in the art such as solid-phase synthesis or liquid-phase synthesis (Process A) and a process for producing an oligosaccharide chain added GLP-1 peptide which comprises producing a peptide wherein any amino acid of GLP-1 is substituted with Cys, according to a peptide synthesis method known in the art and then adding an oligosaccharide chain to the Cys through chemical synthesis (Process B). A process for producing an oligosaccharide chain added GLP-1 peptide having an oligosaccharide chain added amino acid wherein the oligosaccharide chain is linked to the amino acid via a linker and the linker contains an amino acid at the terminal bound to the oligosaccharide chain is exemplified by a process for producing an oligosaccharide chain added GLP-1 peptide which comprises first binding one end of a linker to oligosaccharide chain added Asn, then binding an N-hydroxysuccinimidyl group to the other end of the linker and reacting the N-hydroxysuccinimidyl group with the side chain amino group of the Lys residue of a GLP-1 peptide (Process C). Those skilled in the art can produce various oligosaccharide chain added GLP-1 peptides with reference to these production processes. The oligosaccharide chain added GLP-1 peptides thus obtained and production processes thereof are very useful particularly in the field of pharmaceutical production. Two or more of these Processes A to C may be performed in combination. For synthesis in small amounts, e.g., for assay use, these processes may also be combined with oligosaccharide chain extension reaction catalyzed by transferase. The Processes A an B are described in the pamphlets of WO 2004/005330 (US2005222382 (A1)) and WO 2005/010053 (US2007060543 (A1)), respectively. The disclosures thereof are incorporated herein by reference in their entirety. Production of oligosaccharide chains having a uniform oligosaccharide chain structure used in the Processes A to C are described in the pamphlets of WO03/008431 (US2004181054 (A1)), WO2004/058984 (US2006228784 (A1)), WO2004/058824 (US2006009421 (A1)), WO2004/070046 (US2006205039 (A1)), WO2007/011055, etc. The disclosures thereof are incorporated herein by reference in their entirety.

Process for Producing Oligosaccharide Chain Added GLP-1 Peptide (Process A)

First, (1) a hydroxyl group of a resin having the hydroxyl group and a carboxyl group of an amino acid having amino group nitrogen protected with a fat-soluble protective group are subjected to an esterifying reaction. Since the amino group nitrogen of the amino acid is protected with a fat-soluble protective group, the hydroxyl group of the resin is reacted with the carboxyl group of the amino acid, with self-condensation of the amino acid prevented.

Next, (2) the fat-soluble protective group is removed from the resulting ester to form a free amino group, (3) the free amino group is amidated with a carboxyl group of a desired amino acid having amino group nitrogen protected with a fat-soluble protective group, (4) the fat-soluble protective group is removed to form a free amino group, and (5) the steps (3) and (4) are repeated at least once to thereby obtain a peptide having a desired number of desired amino acids as linked and having the resin attached to one end thereof and a free amino group at the other end thereof.

Next, (6) the free amino group is amidated with a carboxyl group of the asparagine portion of an asparagine-linked oligosaccharide (oligosaccharide chain added asparagine) having amino group nitrogen protected with a fat-soluble protective group, (7) the fat-soluble protective group is removed to form a free amino group, (8) the free amino group is amidated with a carboxyl group of a desired amino acid having amino group nitrogen protected with a fat-soluble protective group, (9) the steps (7) and (8) are repeated at least once, and

(10) the fat-soluble protective group is removed to form a free amino group and thereby obtain a glycopeptide having a desired number of desired amino acids as linked and having the resin attached to one end thereof, a free amino group at the other end thereof and an oligosaccharide chain added asparagine at an intermediate position.

(11) The resin is cut off with an acid, whereby a glycopeptide can be prepared which has an oligosaccharide chain added asparagine at a desired position of the peptide chain thereof.

Alternatively, the oligosaccharide chain added asparagine can be introduced into an end portion of the peptide chain.

The resin having a hydroxyl group may usually be a resin having hydroxyl useful for solid-phase synthesis. Examples of resins usable are Amino-PEGA resin (product of Merck), Wang resin (product of Merck), HMPA-PEGA resin (product of Merck), etc.

All amino acids are usable as such. Examples of amino acids usable are natural amino acids such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe) tryptophan (Trp) and proline (Pro).

Examples of fat-soluble protective groups are 9-fluorenylmethoxycarbonyl (Fmoc) group, tert-butyloxycarbonyl (Boc) group, benzyl group, allyl group, allyloxycarbonyl group, acetyl group and the like, which are carbonate-type or amide-type protective groups. The fat-soluble protective group, e.g., Fmoc group, can be introduced by adding 9-fluorenylmethyl-N-succinimidyl carbonate and sodium hydrogencarbonate to the contemplated compound for reaction. It is preferable to conduct the reaction at 0 to 50 DEG C, preferably at room temperature, for about 1 to about 5 hours.

The above amino acid can be protected with a fat-soluble protective group by the method described above. The above protected amino acid can be those available commercially. Examples are Fmoc-Ser, Fmoc-Asn, Fmoc-Val, Fmoc-Leu, Fmoc-Ile, Fmoc-Ala, Fmoc-Tyr, Fmoc-Gly, Fmoc-Lys, Fmoc-Arg, Fmoc-His, Fmoc-Asp, Fmoc-Glu, Fmoc-Gln, Fmoc-Thr, Fmoc-Cys, Fmoc-Met, Fmoc-Phe, Fmoc-Trp and Fmoc-Pro.

Usable as esterifying catalysts are dehydrating condensation agents such as 1-mesitylenesulfonyl-3-nitro-1,2,4-triazole (MSNT), dicyclohexylcarbodiimide (DCC) and diisopropylcarbodiimide (DIPCI). The dehydrating condensation agent is used in an amount of 1 to 10 wt %, preferably 2 to 5 wt %, based on 1 wt % of an amino acid.

The esterifying reaction is conducted preferably by placing a resin, for example, into a solid-phase column, washing the resin with a solvent and thereafter adding a solution of amino acid in a solvent to the resin. Examples of solvents for washing are dimethylformamide (DMF), 2-propanol, methylene chloride, etc. Examples of solvents for dissolving amino acids are dimethyl sulfoxide (DMSO), DMF, methylene chloride, etc. The reaction is conducted at 0 to 50 DEG C, preferably at room temperature, for about 10 to about 30 hours, preferably about 15 minutes to about 24 hours.

Preferably, the unreacted hydroxyl group remaining on the solid phase at this time is acetylated, for example, with acetic anhydride for capping.

The fat-soluble protective group can be removed, for example, by a treatment with a base. Examples of bases to be used are piperidine, morpholine, etc. This treatment is conducted preferably in the presence of a solvent. Examples of solvents usable are DMSO, DMF, methanol, etc.

The reaction of amidating the free amino group with a carboxyl group of a desired amino acid having amino group nitrogen protected with the fat-soluble group is conducted, preferably in the presence of an activator and a solvent.

Examples of useful activators are dicyclohexylcarbodiimide (DCC), 1-ethyl-3-(3-dimethylaminopropyl)carbodiimide/hydrochloride (WSC/HCl), diphenylphosphorylazide (DPPA), carbonyldiimidazole (CDI), diethylcyanophosphonate (DEPC), diisopropylcarbodiimide (DIPCI), benzotriazole-1-yloxy-trispyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazole-1-yl)-1,1,3,3-tetramethyluronium hexafluorophosphate (HBTU), O-(7-azabenzotriazole-1-yl)-1,1,3,3-tetramethyluronium hexafluorophosphonate (HATU), O-benzotriazole-1-yl-1,1,3,3-tetramethyluronium tetrafluoroborate (TBTU), 3,4-dihydro-3-hydrodi-4-oxo-1,2,3-benzotriazine (Dhbt).

The activator is used in an amount of 1 to 20 equivalents, preferably 1 to 10 equivalents, more preferably 1 to 5 equivalents, based on an amino acid having amino group nitrogen protected with a fat-soluble protective group.

Examples of useful solvents are DMSO, DMF, methylene chloride, etc. It is desired that the reaction be conducted at 0 to 50 DEG C, preferably at room temperature, for about 10 to about 30 hours, preferably about 15 minutes to about 24 hours. The fat-soluble protective group can be removed in the same manner as described above.

The peptide chain is cut off from the resin, preferably by a treatment with an acid. Examples of acids to be used are trifluoroacetic acid (TFA), hydrogen fluoride (HF), etc.

A glycopeptide having at least two oligosaccharide chain added asparagines at a desired position of the peptide chain thereof can be prepared by suitably adding the step (6) of causing amidation between the free amino group of the peptide and a carboxyl group of the asparagine portion of an oligosaccharide chain added asparagine having amino group nitrogen protected with a fat-soluble protective group and the step (7) of removing the fat-soluble protective group to form a free amino group. At this time, a glycopeptide having at least two kinds of oligosaccharide chain added asparagines at a desired position of the peptide chain thereof can also be prepared by using a different oligosaccharide chain added asparagine.

A glycopeptide having at least one oligosaccharide chain added asparagine at a desired position of the peptide chain thereof can be prepared by performing, as final steps, i.e., instead of the steps (9) and (10), the step (6) of causing amidation between the free amino group and a carboxyl group of the asparagine portion of an oligosaccharide chain added asparagine having amino group nitrogen protected with a fat-soluble protective group, and (7) of removing the fat-soluble protective group to form a free amino group.

A glycopeptide having an oligosaccharide chain added asparagine at the C terminal can be prepared by performing the step (1) of subjecting, to esterifying reaction, a hydroxyl group of a resin and a carboxyl group of the asparagine portion of an oligosaccharide chain added asparagine having amino group nitrogen protected with a fat-soluble protective group instead of an amino acid having amino group nitrogen protected with a fat-soluble protective group. In this case, the step (6) may or may not be further performed.

In this way, an oligosaccharide chain added GLP-1 peptide substituted at a desired position with oligosaccharide chain added Asn can be obtained.

Process for Producing Oligosaccharide Chain Added GLP-1 Peptide (Process B)

First, a peptide containing Cys is produced by a method such as solid-phase synthesis, liquid-phase synthesis, cell-based synthesis and separation and extraction of those existing naturally. An oligosaccharide chain can be added to a desired position by changing the position of Cys.

Next, a haloacetamide complex-type oligosaccharide chain derivative is allowed to react with the thus-obtained peptide containing Cys for production. The reaction may be conducted usually at 0 to 80° C., preferably 10 to 60° C., more preferably 15 to 35° C. The reaction time is usually preferably about 30 minutes to about 5 hours. After the completion of reaction, the reaction product may be purified appropriately by a method known in the art [e.g., high-performance liquid column chromatography (HPLC)].

The haloacetamide complex-type oligosaccharide chain derivative is, e.g., a compound wherein a hydroxyl group bound to carbon at position 1 of a complex-type asparagine-linked oligosaccharide chain is substituted with —NH—(CO)—$(CH_2)_a$—$CH_2X$, wherein X represents a halogen atom, and a represents an integer, preferably an integer of 0 to 4, but not limited to these numbers unless linker functions of interest are inhibited.

Specifically, the haloacetamide complex-type oligosaccharide chain derivative is allowed to react with the peptide containing Cys in a phosphate buffer at room temperature. After the completion of reaction, an oligosaccharide chain added GLP-1 peptide substituted with oligosaccharide chain added Cys can be obtained by HPLC purification.

Process for Producing Oligosaccharide Chain Added GLP-1 Peptide (Process C)

First, a peptide containing Lys is produced by a method such as solid-phase synthesis, liquid-phase synthesis, cell-based synthesis and separation and extraction of those existing naturally.

Next, glutaric acid is bound to an oligosaccharide chain added amino acid. For example, the oligosaccharide chain added amino acid is dissolved in a DMSO solution. To this solution, a DMSO solution containing a glutaric acid-EDC mixture is added and stirred at room temperature for 1 day. The reaction mixture can be diluted appropriately and then fractionated by size-exclusion gel filtration chromatography, etc., to obtain an oligosaccharide chain added amino acid wherein glutaric acid is bound to α-amino group.

Subsequently, to the DMSO solution of the glutaric acid-bound oligosaccharide chain added amino acid, a DMSO solution of N-hydroxysuccinimide and a DMSO solution of EDC are added and stirred at room temperature for 6 hours. Then, EDC can be inactivated to synthesize N-hydroxysuccinimidyl ester of the glutaric acid-bound oligosaccharide chain added amino acid.

Subsequently, DIPEA and the N-hydroxysuccinimidyl ester of the glutaric acid-bound oligosaccharide chain added amino acid are added to a DMSO solution of a GLP-1 peptide and stirred at room temperature for 2 hours. Then, the reaction is terminated by the addition of an aqueous glycine solution. The reaction solution can be subjected to appropriate purification to link the oligosaccharide chain added amino acid to the Lys residue of the GLP-1 peptide via the glutaric acid linker. In this way, oligosaccharide chain added GLP-1 having an oligosaccharide chain added amino acid wherein the oligosaccharide chain is linked to the amino acid (Lys) via a linker and the linker contains an amino acid (Asn) at the terminal bound to the oligosaccharide chain is obtained.

An oligosaccharide chain added GLP-1 peptide having an oligosaccharide chain added amino acid bound to a desired site can be obtained by substituting an amino acid at the desired site of the GLP-1 peptide with Lys or substituting a Lys residue contained in a wild-type GLP-1 peptide with another amino acid. According to the Process C, when an oligosaccharide chain is added to Lys contained in wild-type GLP-1, an oligosaccharide chain added GLP-1 peptide having the same peptide skeleton as that of the wild type can be obtained.

The oligosaccharide chain added GLP-1 peptide of the present invention has GLP-1 activity.

The "GLP-1 activity" used herein refers to some or all of biological activities known in the art as to GLP-1. GLP-1 has been known to have, in addition to the effect of controlling blood-sugar levels, e.g., insulin secretion associated with cAMP synthesis induction, pancreatic islet protection (apoptosis suppression) and pancreatic islet growth as effects on a pancreatic islet as well as appetite suppression, gastrointestinal motility suppression, calcitonin secretion promotion and cardioprotective action during ischemia as extra-pancreatic effects. Thus, the GLP-1 activity refers to all or some of biological activities associated with these effects, and these activities can be measured respectively using an approach known by those skilled in the art.

Of the GLP-1 activities, e.g., the activity of controlling blood-sugar levels can be measured using the measurement of the effect of lowering blood-sugar levels in diabetes mice (db/db mice) or the measurement of the effect of suppressing rise in blood-sugar levels in Oral Glucose Tolerance Test (OGTT). The phrase "controlling blood-sugar levels" used herein encompasses both concepts of suppressing rise in blood-sugar levels and lowering blood-sugar levels. Particularly, the effect of controlling blood-sugar levels in db/db mice is also referred to herein as the "effect of lowering blood-sugar levels", and the effect of controlling blood-sugar levels in OGTT is also referred to herein as the "effect of suppressing rise in blood-sugar levels".

The activity of controlling blood-sugar levels in OGTT can be determined by measuring suppression of rise in blood-sugar levels in mice forced to drink sugar. When, e.g., an approach of following Test Example 7 is used, a test compound is first administered to mice fasted overnight. 30 minutes after the administration, a glucose solution is orally administered to the mice. Mouse blood-sugar levels increase due to the glucose administration, reach the maximum about 30 minutes after the administration, and gradually decrease. The blood-sugar levels can be measured 30 minutes after the glucose administration and compared with those obtained by GLP-1 administration to thereby measure the effect of controlling blood-sugar levels by the oligosaccharide chain added GLP-1 peptide. When the blood-sugar levels measured 30 minutes thereafter are compared with those obtained by GLP-1 administration, the oligosaccharide chain added GLP-1 peptide of the present invention exhibits preferably 80% or lower, more preferably 60% or lower, even more preferably 40% or lower, particularly preferably 20% or lower of the control blood sugar levels. The strength of the activity of controlling blood-sugar levels by the oligosaccharide chain added GLP-1 peptide of the present invention can be determined by comparing doses confirmed in OGTT to bring about equivalent effects of suppressing rise in blood-sugar levels. When, e.g., 10 doses of GLP-1 and 1 dose of the oligosaccharide chain added GLP-1 peptide produce the same effects of controlling blood-sugar levels, the activity of controlling blood-sugar levels by the oligosaccharide chain added GLP-1 peptide is 10 times that of the GLP-1. The oligosaccharide chain added GLP-1 peptide of the present invention has the activity of controlling blood-sugar levels preferably at least 5 times, more preferably at least 10 times that of GLP-1.

When the oligosaccharide chain added GLP-1 peptide is an oligosaccharide chain added peptide having deletion, substitution or addition of one or several amino acids of GLP-1 or an oligosaccharide chain added GLP-1 analog, a GLP-1 analog or a GLP-1 peptide having an amino acid sequence identical to the oligosaccharide chain added GLP-1 peptide except the oligosaccharide chain added amino acid may be used as comparison material for GLP-1 activity.

The activity of controlling blood-sugar levels in db/db mice can be determined by measuring blood-sugar levels in diabetes mice after administration of a test compound. When, e.g., blood-sugar levels after test compound administration are measured over time. The effect of lowering blood-sugar levels can be confirmed, if blood-sugar levels measured, e.g., 120 minutes after the administration are lower than those measured at the time of administration. Alternatively, the durability of the effect of lowering blood-sugar levels can be determined by measuring blood-sugar levels, e.g., 300 minutes after the administration. When, e.g., blood-sugar levels measured 120 minutes after the administration are compared with those obtained by GLP-1 administration, the oligosaccharide chain added GLP-1 peptide of the present invention exhibits preferably 80% or lower, more preferably 70% or lower, particularly preferably 60% or lower of the control blood-sugar levels. Alternatively, when blood-sugar levels measured 120 minutes after the administration are compared with those measured at the time of administration, the oligosaccharide chain added GLP-1 peptide of the present invention exhibits preferably 70% or lower, more preferably 60% or lower, particularly preferably 50% or lower (e.g., 45% or lower) of the control blood-sugar levels. When blood-sugar levels measured 300 minutes after the administration are compared with those obtained by GLP-1 administration, the oligosaccharide chain added GLP-1 peptide of the present invention exhibits preferably 70% or lower, more preferably 50% or lower of the control blood-sugar levels. When blood-sugar levels measured 300 minutes after the administration are compared with those measured at the time of administration, the oligosaccharide chain added GLP-1 peptide of the present invention exhibits preferably 70% or lower, more preferably 50% or lower of the control blood-sugar levels.

Even if the activity of controlling blood-sugar levels by the oligosaccharide chain added GLP-1 peptide of the present invention is lower than that of GLP-1, this low activity can be compensated by enhanced stability in blood.

Of the GLP-1 activities, e.g., insulin secretion activity can be measured using an in-vitro test of the ability to synthesize cAMP. GLP-1 increases intracellular cAMP concentrations through the binding to its receptor and promotes insulin secretion. Thus, e.g., mouse GLP-1 receptor-expressing CHO-K1 cells are stimulated with the oligosaccharide chain added GLP-1 peptide and then, the amount of cAMP synthesized in the cells is measured. Its EC50 value can be compared with that obtained by GLP-1 to thereby measure the insulin secretion activity of the oligosaccharide chain added GLP-1 peptide.

The oligosaccharide chain added GLP-1 peptide of the present invention has higher stability in blood than that of GLP-1. The stability in blood can be measured using an approach known by those skilled in the art and can be determined by measuring, e.g., stability in plasma or resistance to DPP-IV (dipeptidyl peptidase IV) and using a half-life, AUC (area under the blood concentration time curve), etc., as an index. Increased renal clearance also contributes to enhancement in stability in blood.

The stability in plasma can be determined using, e.g., an approach described in following Test Example 1. The oligosaccharide chain added GLP-1 peptide of the present invention has higher stability in plasma than that of GLP-1.

The resistance to DPP-IV can be determined by measuring a half-life in a DPP-IV solution, as shown in, e.g., following Test Example 1. The oligosaccharide chain added GLP-1 peptide of the present invention has higher resistance to DPP-IV than that of GLP-1 and has a half-life at least 1.2 times (e.g., at least 2 times), preferably at least 5 times, more preferably at least 10 times, particularly preferably at least 20 times higher than that of GLP-1 (e.g. at least 100 times), when resistance to DPP-IV is measured using, e.g., the approach of following Test Example 1.

The oligosaccharide chain added GLP-1 peptide of the present invention also has a half-life of preferably at least 1 hour, more preferably at least 3, 5, 7, 10, 15 and 20 hours, even more preferably at least 24 hours, in blood.

Next, a pharmaceutical composition comprising the oligosaccharide chain added GLP-1 peptide of the present invention as an active ingredient will be described.

The pharmaceutical composition comprising the oligosaccharide chain added GLP-1 peptide of the present invention as an active ingredient is effective for the treatment or prevention of diseases associated with GLP-1. GLP-1 has been known to have various effects, as described above, and these effects are associated with various diseases. It has been found that, e.g., GLP-1 stimulates insulin release and thereby causes cellular uptake of glucose and reduction in blood-sugar levels. It has also been found that GLP-1 suppresses gastric and/or intestinal motility, gastric and/or intestinal emptying, and food ingestion. Thus, the diseases associated with GLP-1 encompass, e.g., non-insulin-dependent diabetes mellitus (NIDDM), insulin-dependent diabetes mellitus, stroke (see WO 00/16797 by Efendic), myocardial infarction (see WO 98/08531 by Efendic), obesity (see WO 98/19698 by Efendic), functional dyspepsia, irritable bowel syndrome (see WO 99/64060 by Efendic) and pancreatic islet transplantation. The pharmaceutical composition comprising the oligosaccharide chain added GLP-1 peptide of the present invention as an active ingredient is effective particularly for the treatment or prevention of diabetes, more specifically, for the prevention of type 1 diabetes and the treatment of type 2 diabetes.

The pharmaceutical composition may be formulated in a usual pharmaceutical composition form using diluents or excipients such as fillers, extenders, binders, wetting agents, disintegrants, surfactants and lubricants usually used.

Examples of such a pharmaceutical composition include tablets, pills, powders, liquid formulations, suspensions, emulsions, granules, capsules, suppositories and injections.

The amount of the oligosaccharide chain added GLP-1 peptide of the present invention contained in the pharmaceutical composition is not particularly limited and can be selected appropriately from within a wide range. The oligosaccharide chain added GLP-1 peptide of the present invention is usually contained in an amount of preferably 1 to 70 wt % in the pharmaceutical composition.

The pharmaceutical composition comprising the oligosaccharide chain added GLP-1 peptide of the present invention as an active ingredient may further contain an additional active ingredient or may also be used in combination with a pharmaceutical composition containing an additional active ingredient. Moreover, the pharmaceutical composition comprising the oligosaccharide chain added GLP-1 peptide of the present invention as an active ingredient may further comprise at least one different oligosaccharide chain added GLP-1 peptide of the present invention as an active ingredient or may also be used in combination with a pharmaceutical composition comprising at least one different oligosaccharide chain added GLP-1 peptide of the present invention as an active ingredient.

An administration method of the pharmaceutical composition according to the present invention is not particularly limited. The pharmaceutical composition according to the present invention is administered by a method suitable for various dosage forms, the age and sex of a patient, the severity of a disease and other conditions. Examples of administration methods of tablets, pills, liquid formulations, suspensions, emulsions, granules and capsules include oral administration. Injections can be administered intravenously, intramuscularly, intradermally, subcutaneously or intraperitoneally either alone or as a mixture with a usual glucose or amino acid infusion. Suppositories are administered rectally.

The dose of the pharmaceutical composition may be selected appropriately according to use, the age and sex of a patient, the severity of a disease and other conditions. The pharmaceutical composition is usually administered at a dose of 0.1 to 900 nmol, preferably 1 to 90 nmol, in terms of the oligosaccharide chain added GLP-1 peptide of the present invention per kg of body weight. The oligosaccharide chain added GLP-1 peptide of the present invention has much higher stability in blood than that of GLP-1. In one aspect, the oligosaccharide chain added GLP-1 peptide of the present invention has much higher activity of controlling blood-sugar levels than that of GLP-1. Therefore, its dose can be decreased advantageously.

The number of doses of the pharmaceutical composition may be selected appropriately according to use, the age and sex of a patient, the severity of a disease and other conditions and is, e.g., 3 doses/day, 2 doses/day or 1 dose/day. Alternatively, the pharmaceutical composition may be administered with less frequency (e.g., 1 dose/week, or 1 dose/month) according to its stability in blood. The number of doses of the pharmaceutical composition is preferably 1 dose or less/day. The oligosaccharide chain added GLP-1 peptide of the present invention has much higher stability in blood than that of GLP-1. Therefore, the number of doses can be decreased advantageously.

The oligosaccharide chain added to the oligosaccharide chain added GLP-1 peptide of the present invention is easily degraded in a metabolic system in vivo. In one aspect of the present invention, the oligosaccharide chain has a structure that is bound in a form of glycopeptide (or glycoprotein) in vivo. Thus, the oligosaccharide chain added GLP-1 peptide of the present invention and the pharmaceutical composition comprising this peptide as an active ingredient exhibits neither side effects nor antigenicity, even when administered to living bodies. Therefore, they advantageously produce neither allergic reactions nor a loss of efficacy attributed to antibody production.

Furthermore, the oligosaccharide chain added GLP-1 peptide of the present invention can be supplied stably and conveniently in large amounts and is also very useful from the viewpoint of providing a high-quality drug having stable quality.

The present invention also provides a method for treating or preventing a disease associated with GLP-1, comprising administering an effective amount of the oligosaccharide chain added GLP-1 peptide of the present invention.

The terms used herein are used for describing particular embodiments and are not intended to limit the present invention.

The term "comprise" or "comprising" used herein means the existence of a stated item (member, step, factor, number, etc) and does not exclude the existence of any other item (member, step, factor, number, etc), unless otherwise interpreted in the context.

All the terms (including technical terms and scientific terms) used herein have the same meanings as those broadly understood by those skilled in the art of the present invention, unless otherwise defined. The terms used herein should be interpreted as having a meaning that is consistent with their meanings in the context of the specification and relevant art and should not be interpreted in an idealized or overly formal sense, unless their different definitions are specified.

The embodiments of the present invention may be described with reference to schematic diagrams. These schematic diagrams may be exaggerated for purposes of illustration.

Terms such as "first", and "second" are used for expressing various factors. It will be understood that these factors should not be limited by these terms. These terms are used only for discriminating one factor from another factor. For example, the first factor can be described as a second factor, and vice versa, without departing from the scope of the present invention.

Hereinafter, the present invention will be described in more detail with reference to Examples. However, the present invention can be realized in various aspects and is not intended to be limited to Examples described herein.

EXAMPLE

Hereinafter, the present invention will be described specifically with reference to Examples. However, the present invention is not intended to be limited to them by any means.

Example 1

Synthesis of 26Cys,34Cys-disialo oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25'C for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids. Fmoc-Gly, Fmoc-Arg(Pbf), Fmoc-Gly, Fmoc-Cys(Trt), Fmoc-Val, Fmoc-Leu, Fmoc-Trp (Boc), Fmoc-Ala, Fmoc-Ile, Fmoc-Phe, Fmoc-Glu(OtBu), Fmoc-Cys(Trt), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp (OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Leu-Trp(Boc)-Ala-Ile-Phe-Glu(OtBu)-Cys(Trt)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt)-Boc (Sequence No. 69).

The obtained resin having a peptide formed thereon was partly taken in a solid-phase synthesis column.

Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain a peptide wherein 26Lys and 34Lys of GLP-1 were each substituted with Cys.

The following bromoacetamidyl disialo oligosaccharide (a) (a product of OTSUKA Chemical Co., Ltd.) (10.5 mg) and the peptide chain synthesized above (2.1 mg) were dissolved in 100 mM phosphate buffer (pH 7.5, 210 μl) and allowed to react at 37° C. for 4 hours.

[Formula 15]

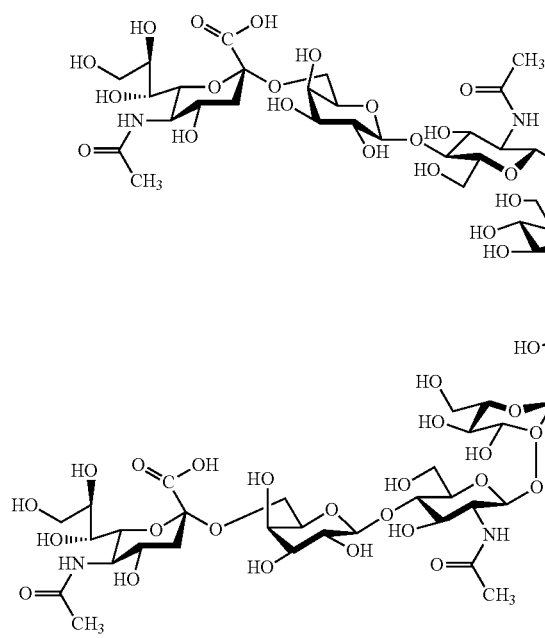

(a)

After complete consumption of the raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 0.1 mg of oligosaccharide chain added GLP-1 peptide wherein 26Lys and 34Lys of GLP-1 were each substituted with oligosaccharide chain added Cys (26,34Cys GLP-1-disialo).

Example 2

Synthesis of 18 and 36Cys-disialo oligosaccharide Chain Added GLP-1

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Cys(Trt), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Cys(Trt), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu), Fmoc-Ala and Fmoc-His(Trt) were used as the amino acids protected by Fmoc group to obtain a 31-residue peptide of Gly-Cys(Trt)-Gly-Lys(Boc)-Val-Leu-Trp(Boc)-Ala-Ile-Phe-Glu(OtBu)-Lys(Boc)-Ala-Ala-Gln(Trt)-Gly-Glu (OtBu)-Leu-Tyr(tBu)-Cys(Trt)-Ser(tBu)-Val-Asp(OtBu)-Ser(tBu)-Thr(tBu)-Phe-Thr(tBu)-Gly-Glu(OtBu)-Ala-His (Trt) (SEQ ID NO: 70) on a solid-phase resin.

The obtained resin having a peptide formed thereon was partly taken in a solid-phase synthesis column. Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain a peptide wherein 18Ser and 36Arg of GLP-1 were each substituted with Cys.

Bromoacetamidyl disialo oligosaccharide (a) (a product of OTSUKA Chemical Co., Ltd.) (10.5 mg) and the peptide chain synthesized above (2.1 mg) were dissolved in 100 mM phosphate buffer (pH 7.5, 210 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ4.6×250 mm, gradient: A solution: 0.1% TFA water, B solution: 0.09% TFA/10% water/90% AN 0.7 ml/min; 35→60% B, 20 min linear gradient] to obtain 0.8 mg of oligosaccharide chain added GLP-1 peptide wherein 18Ser and 36Arg of GLP-1 were each substituted with oligosaccharide chain added Cys (18,36Cys GLP-1-disialo).

Example 3

Synthesis of 22 and 30Cys-disialo oligosaccharide Chain Added GLP-1

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Cys(Trt), Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Cys(Trt), Fmoc-Glu(OtBu), Fmoc-Leu, Fmoc-Tyr(tBu), Fmoc-Ser (Trt), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Cys(Trt)-Ile-Phe-Glu(OtBu)-Lys(Boc)-Ala-Ala-Gln(Trt)-Cys(Trt)-Glu(OtBu)-Leu-Tyr(tBu)-Ser (tBu)-Ser(tBu)-Val-Asp(OtBu)-Ser(tBu)-Thr(tBu)-Phe-Thr (tBu)-Gly-Glu(OtBu)-Ala-His(Trt) (SEQ ID NO: 71) on a solid-phase resin.

The obtained resin having a peptide formed thereon was partly taken in a solid-phase synthesis column. Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 μm), φ20×250 mm, gradient: A solution: 0.1% TFA water, B solution: 0.09% TFA/10% water/90% AN 8.0 ml/min; 35→60% B, 20 min linear gradient] to obtain a peptide wherein 22Gly and 30Ala of GLP-1 were each substituted with Cys.

Bromoacetamidyl disialo oligosaccharide (a) (a product of OTSUKA Chemical Co., Ltd.) (7.9 mg) and the peptide chain synthesized above (1.3 mg) were dissolved in 100 mM phosphate buffer (pH 7.4, 200 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ4.6×250 mm, gradient: A solution: 0.1% TFA water, B solution: 0.09% TFA/10% water/90% AN 0.7 ml/min; 35→60% B, 20 min linear gradient] to obtain 1.0 mg of oligosaccharide chain added GLP-1 peptide wherein 22Gly and 30Ala of GLP-1 were each substituted with oligosaccharide chain added Cys (22,30Cys GLP-1-disialo).

Example 4

Synthesis of 22 and 36Cys-disialo oligosaccharide Chain Added GLP-1

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Cys(Trt), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Cys(Trt), Fmoc-Glu (OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala, Fmoc-His(Trt) were used as the amino acids protected by Fmoc group to obtain a 31-residue peptide of Gly-Cys(Trt)-Gly-Lys(Boc)-Val-Leu-Trp (Boc)-Ala-Ile-Phe-Glu(OtBu)-Lys(Boc)-Ala-Ala-Gln(Trt)-Cys(Trt)-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu (OtBu)-Ala-His(Trt)-Cys(Trt) (SEQ ID NO:72) on a solid-phase resin.

The obtained resin having a peptide formed thereon was partly taken in a solid-phase synthesis column. Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 μm), ϕ20×250 mm, gradient: A solution: 0.1% TFA water, B solution: 0.09% TFA/10% water/90% AN 8.0 ml/min; 35→60% B, 20 min linear gradient] to obtain a peptide wherein 22Gly and 36Arg of GLP-1 were each substituted with Cys.

Bromoacetamidyl disialo oligosaccharide (a) (a product of OTSUKA Chemical Co., Ltd.) (11.9 mg) and the peptide chain synthesized above (2.0 mg) were dissolved in 100 mM phosphate buffer (pH 7.4, 400 μl) and allowed to react at 37° C. for 1 hour. After complete consumption of raw materials were confirmed by HPLC, the reaction solution was directly subjected to purification by HPLC [column: SHISEIDO UG-120 (C18, 5 μm), ϕ4.6×250 mm, gradient: A solution: 0.1% TFA water, B solution: 0.09% TFA/10% water/90% AN 0.7 ml/min; 35→60% B, 20 min linear gradient] to obtain 2.9 mg of oligosaccharide chain added GLP-1 peptide wherein 22Gly and 36Arg of GLP-1 were each substituted with oligosaccharide chain added Cys (22,36Cys GLP-1-disialo).

Example 5

Synthesis of 30,36Cys-disialo oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Cys(Trt), Fmoc-Gly, Fmoc-Lys(Boc), Fmoc-Val, Fmoc-Leu, Fmoc-Trp(Boc), Cys(Trt), Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Cys(Trt)-Gly-Lys(Boc)-Val-Leu-Trp(Boc)-Cys(Trt)-Ile-Phe-Glu(OtBu)-Lys(Boc)-Ala-Ala-Gln(Trt)-Gly-Glu (OtBu)-Leu-Tyr(tBu)—Ser(tBu)-Ser(tBu)-Val-Asp(OtBu)-Ser(tBu)-Thr(tBu)-Phe-Thr(tBu)-Gly-Glu(OtBu)-Ala-His (Trt) (SEQ ID NO:73) on a solid-phase resin.

The obtained resin having a peptide formed thereon was partly taken in a solid-phase synthesis column.

Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 μm), ϕ20×250 mm, gradient: A solution: 0.1% TFA water, B solution: 0.09% TFA/10% water/90% AN 8.0 ml/min; 35→60% B, 20 min linear gradient] to obtain a peptide wherein 30Ala and 36Arg of GLP-1 were each substituted with Cys.

Bromoacetamidyl disialo oligosaccharide (a) (a product of OTSUKA Chemical Co., Ltd.) (11.4 mg) and the peptide chain synthesized above (2.1 mg) were dissolved in 100 mM phosphate buffer (pH 7.4, 400 μl) and allowed to react at 37° C. for 1 hour. After complete consumption of raw materials were confirmed by HPLC, the reaction solution was directly subjected to purification by HPLC [column: SHISEIDO UG-120 (C18, 5 μm), ϕ4.6×250 mm, gradient: A solution: 0.1% TFA water, B solution: 0.09% TFA/10% water/90% AN 0.7 ml/min; 35→60% B, 20 min linear gradient] to obtain 1.6 mg of oligosaccharide chain added GLP-1 peptide wherein 30Ala and 36Arg of GLP-1 were each substituted with oligosaccharide chain added Cys (30,36Cys GLP-1-disialo).

Example 6

Synthesis of 30Cys-hyaluronic acid tetrasaccharide (HA-4) Added GLP-1 Peptide

Hyaluronic acid tetrasaccharide (hereinafter, oligo hyaluronic acid is also simply referred to as "hyaluronic acid" in Examples) obtained in Synthesis Example 1 (12.7 mg) was dissolved by the addition of 25.4 μl of water and 483 μl of dimethyl sulfoxide (DMSO). This solution was treated with 200 mg of ammonium bicarbonate at 37° C. for 30 hours and then freeze-dried. To the obtained freeze-dried product, 22.4 mg of sodium hydrogencarbonate, 300 μl of water, and 34.9 mg of bromoacetic anhydride (a product of Sigma-Aldrich Corp.) dissolved in advance in 17 μl of N,N-dimethylformamide (DMF) were added and allowed to react for 1 hour with ice cooling. One hour later, the reaction system was returned to room temperature and allowed to react for additional 1 hour. The reaction solution was subjected to purification by gel filtration to obtain 11.5 mg of the following bromoacetamidyl hyaluronic acid tetrasaccharide (I):

[Formula 16]

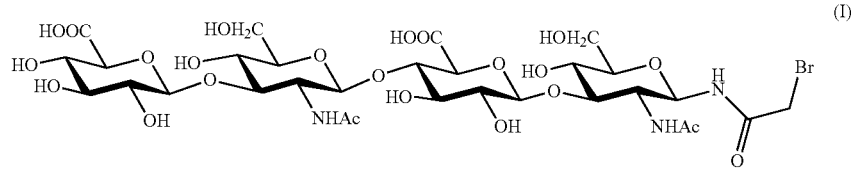

The obtained bromoacetamidyl hyaluronic acid tetrasaccharide (I) (2.4 mg) and a peptide wherein 30Ala of GLP-1 was substituted with Cys (SEQ ID NO: 76) (1.3 mg) synthesized in Synthesis Example 2 were dissolved in 100 mM phosphate buffer (pH 7.5, 130 µl) and allowed to react at 37° C. for 1.5 hours. After complete consumption of raw materials were confirmed by HPLC, the reaction solution was directly subjected to purification by HPLC [column: SHISEIDO UG-120 (C18, 5 µm), φ 4.6×250 mm, gradient: A solution: 0.1% TFA water, B solution: 0.09% TFA/10% water/90% AN 0.7 ml/min; 35→60% B, 20 min linear gradient] to obtain 1.0 mg of oligosaccharide chain added GLP-1 peptide wherein 30Ala of GLP-1 was substituted with hyaluronic acid tetrasaccharide added Cys (30Cys GLP-1-HA-4).

Example 7

Synthesis of 30Cys-hyaluronic acid octasaccharide (HA-8) Added GLP-1 Peptide

Hyaluronic acid octasaccharide obtained in Synthesis Example 1 (8.7 mg) was dissolved by the addition of 17.4 µl of water and 314 µl of dimethyl sulfoxide (DMSO). This solution was treated with 100 mg of ammonium bicarbonate at 37° C. for 45 hours and then freeze-dried. To the obtained freeze-dried product, 7.6 mg of sodium hydrogencarbonate, 180 µl of water, and 13.8 mg of bromoacetic anhydride (a product of Sigma-Aldrich Corp.) dissolved in advance in 7 pa of N,N-dimethylformamide (DMF) were added and allowed to react for 1 hour with ice cooling. One hour later, the reaction system was returned to room temperature and allowed to react for additional 1 hour. The reaction solution was subjected to purification by gel filtration to obtain 7.3 mg of the following bromoacetamidyl hyaluronic acid octasaccharide (II):

confirmed by HPLC, the reaction solution was directly subjected to purification by HPLC [column: SHISEIDO UG-120 (C18, 5 µm), φ4.6×250 mm, gradient: A solution: 0.1% TFA water, B solution: 0.09% TFA/10% water/90% AN 0.7 ml/min; 35→60% B, 20 min linear gradient] to obtain 0.5 mg of oligosaccharide chain added GLP-1 peptide wherein 30Ala of GLP-1 was substituted with hyaluronic acid octasaccharide added Cys (30Cys GLP-1-HA-8).

Example 8

Synthesis of 36Cys-hyaluronic acid tetrasaccharide (HA-4) Added GLP-1 Peptide

Hyaluronic acid tetrasaccharide obtained in Synthesis Example 1 (12.7 mg) was dissolved by the addition of 25.4 µl of water and 483 µl of dimethyl sulfoxide (DMSO). This solution was treated with 200 mg of ammonium bicarbonate at 37° C. for 30 hours and then freeze-dried. To the obtained freeze-dried product, 22.4 mg of sodium hydrogencarbonate, 300 µl of water, and 34.9 mg of bromoacetic anhydride (a product of Sigma-Aldrich Corp.) dissolved in advance in 17 µl of N,N-dimethylformamide (DMF) were added and allowed to react for 1 hour with ice cooling. One hour later, the reaction system was returned to room temperature and allowed to react for additional 1 hour. The reaction solution was subjected to purification by gel filtration to obtain 11.5 mg of bromoacetamidyl hyaluronic acid tetrasaccharide (I).

The obtained bromoacetamidyl hyaluronic acid tetrasaccharide (I) (1.1 mg) and a GLP-1 peptide wherein 36Arg of GLP-1 was substituted with Cys (SEQ ID NO: 78) (1.5 mg) synthesized in Synthesis Example 3 were dissolved in 100 mM phosphate buffer (pH 7.5, 130 µl) and allowed to react at 37° C. for 1.5 hours. After complete consumption of raw materials were confirmed by HPLC, the reaction solution was directly subjected to purification by HPLC [column:

[Formula 17]

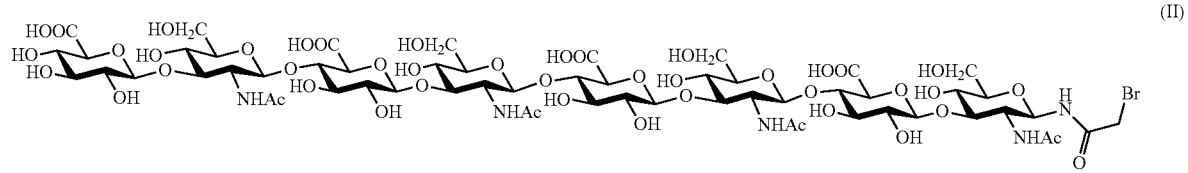

The obtained bromoacetamidyl hyaluronic acid octasaccharide (2.9 mg) and a peptide wherein 30Ala of GLP-1 was substituted with Cys (SEQ ID NO: 76) (1.5 mg) synthesized in Synthesis Example 2 were dissolved in 100 mM phosphate buffer (pH 7.5, 150 µl) and allowed to react at 37° C. for 1.5 hours. After complete consumption of raw materials were SHISEIDO UG-120 (C18, 5 µm), φ4.6×250 mm, gradient: A solution: 0.1% TFA water, B solution: 0.09% TFA/10% water/90% AN 0.7 ml/min; 35→60% B, 20 min linear gradient] to obtain 0.9 mg of oligosaccharide chain added GLP-1 peptide wherein 36Arg of GLP-1 was substituted with hyaluronic acid tetrasaccharide added Cys (36Cys GLP-1-HA-4).

Example 9

Synthesis of 36Cys-hyaluronic acid octasaccharide (HA-8) Added GLP-1 Peptide

Hyaluronic acid octasaccharide (8.7 mg) obtained in Synthesis Example 1 was dissolved by the addition of 17.4 μl of water and 314 μl of dimethyl sulfoxide (DMSO). This solution was treated with 100 mg of ammonium bicarbonate at 37° C. for 45 hours and then freeze-dried. To the obtained freeze-dried product, 7.6 mg of sodium hydrogencarbonate, 180 μl of water, and 13.8 mg of bromoacetic anhydride (a product of Sigma-Aldrich Corp.) dissolved in advance in 7 μl of N,N-dimethylformamide (DMF) were added and allowed to react for 1 hour with ice cooling. One hour later, the reaction system was returned to room temperature and allowed to react for additional 1 hour. The reaction solution was subjected to purification by gel filtration to obtain 7.3 mg of bromoacetamidyl hyaluronic acid octasaccharide (II).

The obtained bromoacetamidyl hyaluronic acid octasaccharide (2.4 mg) and a GLP-1 peptide wherein 36Arg of GLP-1 was substituted with Cys (SEQ ID NO: 78) (1.5 mg) synthesized in Synthesis Example 3 were dissolved in 100 mM phosphate buffer (pH 7.5, 130 μl) and allowed to react at 37° C. for 2 hours. After complete consumption of raw materials were confirmed by HPLC, the reaction solution was directly subjected to purification by HPLC [column: SHISEIDO UG-120 (C18, 5 μm), φ4.6×250 mm, gradient: A solution: 0.1% TFA water, B solution: 0.09% TFA/10% water/90% AN 0.7 ml/min; 35→60% B, 20 min linear gradient] to obtain 0.5 mg of oligosaccharide chain added GLP-1 peptide wherein 36Arg of GLP-1 was substituted with hyaluronic acid octasaccharide added Cys (36Cys GLP-1-HA-8).

Example 10

Synthesis of 30Cys-hyaluronic acid hexadecasaccharide (HA-16) Added GLP-1 Peptide Hyaluronic acid hexadecasaccharide (11.6 mg) obtained in Synthesis Example 1 was dissolved by the addition of 35 μl of water and 680 pa of dimethyl sulfoxide (DMSO). This solution was treated with 260 mg of ammonium bicarbonate at 37° C. for 75 hours and then freeze-dried. To the obtained freeze-dried product, 5.5 mg of sodium hydrogencarbonate, 230 μl of water, and 10.2 mg of bromoacetic anhydride (a product of Sigma-Aldrich Corp.) dissolved in advance in 5.1 μl of N,N-dimethylformamide (DMF) were added and allowed to react for 1 hour with ice cooling. One hour later, the reaction system was returned to room temperature and allowed to react for additional 1 hour. The reaction solution was subjected to purification by gel filtration to obtain 8.7 mg of the following bromoacetamidyl hyaluronic acid hexadecasaccharide (III):

[Formula 18]

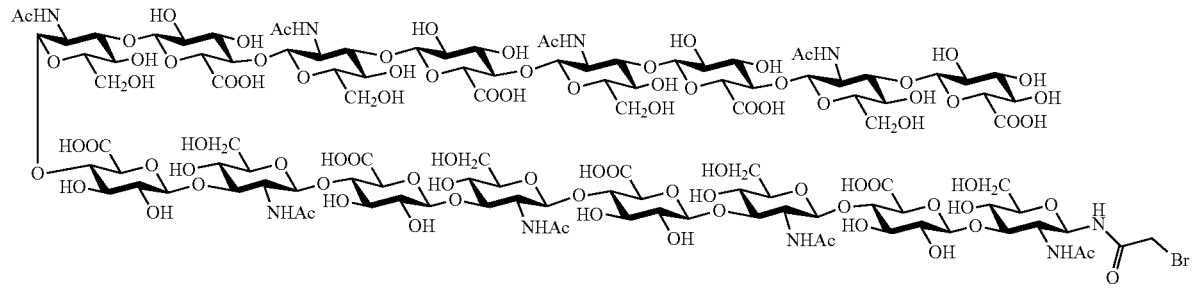

The bromoacetamidyl hyaluronic acid hexadecasaccharide (III) (3.1 mg) and a peptide chain synthesized in Synthesis Example 2 (SEQ ID NO: 76) (1.0 mg) were dissolved in 100 mM phosphate buffer (pH 7.5, 190 μl). After addition of a 10 mM aqueous tris(2-carboxyethyl)phosphine hydrochloride solution (10 μl), the mixture was allowed to react at 37° C. for 8 hours. Since no more reduction in raw materials was observed by HPLC, the reaction solution was directly subjected to purification by HPLC [column: SHISEIDO UG-120 (C18, 5 μm), φ4.6×250 mm, gradient: A solution: 0.1% TFA water, B solution: 0.09% TFA/10% water/90% AN 0.7 ml/min; 35→60% B, 20 min linear gradient] to obtain 0.4 mg of oligosaccharide chain added GLP-1 peptide wherein 30Ala of GLP-1 was substituted with hyaluronic acid hexadecasaccharide added Cys (30Cys GLP-1-HA-16).

Example 11

Synthesis of 36Cys-hyaluronic acid hexadecasaccharide (HA-16) Added GLP-1 Peptide The bromoacetamidyl hyaluronic acid hexadecasaccharide (III) prepared in Example 10 (4.9 mg) and a 36Cys GLP-1 peptide chain synthesized in Synthesis Example 3 (SEQ ID NO: 78) (1.2 mg) were dissolved in 100 mM phosphate buffer (pH 7.5, 190 μl). After addition of a 10 mM aqueous tris(2-carboxyethyl)phosphine hydrochloride solution (36 μl), the mixture was allowed to react at 37° C. for 4 hours. After complete consumption of raw materials were confirmed by HPLC, the reaction solution was directly subjected to purification by HPLC [column: SHISEIDO UG-120 (C18, 5 μm), φ4.6×250 mm, gradient: A solution: 0.1% TFA water, B solution: 0.09% TFA/10% water/90% AN 0.7 ml/min; 35→60% B, 20 min linear gradient] to obtain 0.3 mg of oligosaccharide chain added GLP-1 peptide wherein 36Arg of GLP-1 was substituted with hyaluronic acid hexadecasaccharide added Cys (36Cys GLP-1-HA-16).

Example 12

Synthesis of 36Cys-High-Mannose Type Oligosaccharide Chain (M5) Added GLP-1 Peptide Soybean powder (100 g) was washed twice with 500 ml of acetone and twice with 500 ml of methanol to obtain 61.4 g of defatted soybean powder.

To the obtained defatted soybean powder (43.0 g), 430 ml of water and 4.3 g of Liquefying Enzyme T (a product of HBI Enzymes Inc.) were added and allowed to react at 70° C. for 19 hours with stirring. The reaction solution was separated into a supernatant and precipitates by centrifugation (10000 G, 10 min) to obtain 800 ml of supernatant. To the precipitates, 430 ml of water and 4.3 g of Liquefying Enzyme T were further added and allowed to react again at 70° C. for 19 hours. The reaction solution was separated into a supernatant and precipitates by centrifugation (10000 G, 10 min) to obtain 600 ml of supernatant. The obtained supernatants were combined (1400 ml in total). After addition of 100 ml of 500 mM phosphate buffer (pH 7.0) and 3.0 g of Orientase ONS (a product of HBI Enzymes Inc.), the mixture was allowed to react at 50° C. for 19 hours with stirring. The reaction solution was filtered for removal of insoluble matter, and the filtrate was concentrated to a volume of 400 ml using a rotary evaporator. The obtained solution was subjected to ultrafiltration through an ultrafiltration membrane with molecular weight cutoff of 1 K (Minimate TFF Capsule 1K membrane, a product of PALL Corp.).

After treatment for 6 hours, 230 ml of a solution that did not penetrate the membrane was collected. To the collected solution, 20 ml of 1 M tris-HCl buffer (pH 8.0), 250 mg of sodium azide and 423.5 mg of Actinase E (a product of KAKEN PHARMACEUTICAL CO., LTD.) were added and allowed to react at 37° C. for 82 hours. The reaction solution was filtered for removal of insoluble matter, and the filtrate was then concentrated to a volume of 100 ml using a rotary evaporator. The concentrate was divided into halves, each of which was fractionated using a Sephadex-G25 ($\phi$25 mm×100 mm) column. Only a oligosaccharide chain-containing fraction was collected and concentrated to obtain 2.22 g.

The obtained oligosaccharide chain-containing fraction was dissolved by the addition of 21.0 ml of distilled water and 14.9 ml of ethanol. After addition of 1.13 g of sodium hydrogencarbonate and 2.02 g of Fmoc-OSu, the mixture was allowed to react at room temperature for 16 hours. After the reaction, 250 ml of acetone was added thereto, and the precipitates were filtered through a membrane filter $\phi$47 mm, pore size: 0.5 μm; a product of Advantec Toyo Kaisha, Ltd.). Insoluble matter remaining on the membrane was dissolved in distilled water, collected, and concentrated to a volume of 10 ml or lower using a rotary evaporator. The concentrate was fractionated using a Sephadex-G25 ($\phi$25 mm×100 mm) column. An oligosaccharide chain-containing fraction was collected and concentrated to obtain 1.37 g.

This fraction was further dissolved in 4 ml of distilled water and fractionated using an ODS column (Wakogel 100C18, $\phi$ 25 mm×150 mm). Only an oligosaccharide chain-containing fraction was collected and concentrated to obtain 48.6 mg of a semi-purified oligosaccharide chain. The semi-purified oligosaccharide chain was purified by HPLC [column: YMC-Pack ODS-AM (i) 20×250 mm, eluent: acetonitrile/25 mM ammonium acetate buffer=82/18, flow rate: 8.0 ml/min] to obtain 13.0 mg of a high-mannose type Man5GlcNAc$_2$ oligosaccharide chain (M5 oligosaccharide chain).

The obtained M5 oligosaccharide chain (11.0 mg) was dissolved by the addition of 165 μl of water. This solution was treated with 200 mg of ammonium bicarbonate at room temperature for 41 hours and then freeze-dried. To the obtained freeze-dried product, 12.5 mg of sodium hydrogencarbonate, 110 μl of water, and 19.9 mg of bromoacetic anhydride (a product of Sigma-Aldrich Corp.) dissolved in advance in 10 μl of N,N-dimethylformamide (DMF) were added and allowed to react for 1 hour with ice cooling. One hour later, the reaction system was returned to room temperature and allowed to react for additional 1 hour. The reaction solution was subjected to purification by gel filtration to obtain 7.9 mg of the following bromoacetamidyl M5 oligosaccharide chain (b):

[Formula 19]

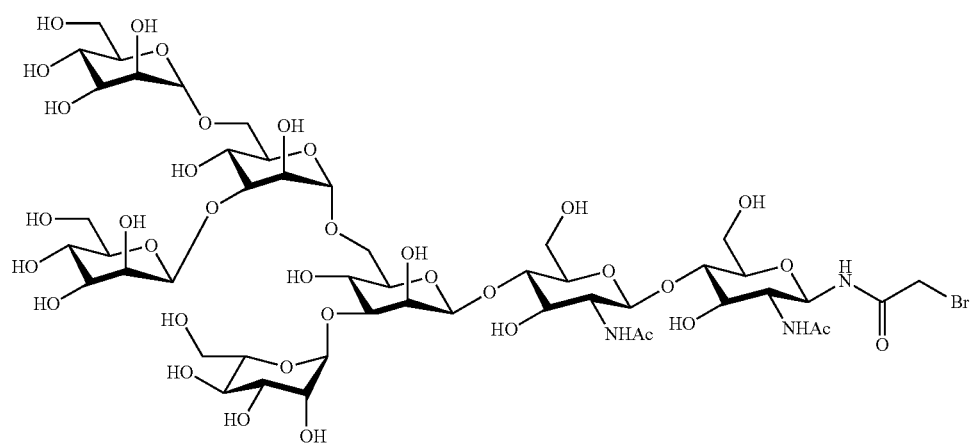

(b)

The obtained bromoacetamidyl M5 oligosaccharide chain (b) (4.1 mg) and a GLP-1 peptide wherein 36Arg was substituted with Cys (SEQ ID NO: 78) (1.2 mg) synthesized in Synthesis Example 3 were dissolved in 100 mM phosphate buffer (pH 7.5, 190 μl). After addition of a 100 mM aqueous tris(2-carboxyethyl)phosphine hydrochloride solution (24 μl), the mixture was allowed to react at 37° C. for 10 hours. After reaction, the reaction solution was subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 0.3 mg of oligosaccharide chain added GLP-1 peptide wherein 36Arg of GLP-1 was substituted with high-mannose type M5 oligosaccharide chain added Cys (36Cys GLP-1-M5).

DMSO-water (4:1, v/v, 1.5 mL). To this solution, a DMSO solution (100 μL, 51.7 μmol) containing a 0.52 M glutaric acid-EDC mixture (1:1, mol/mol) was added and stirred at room temperature for 1 day. The reaction mixture was diluted with distilled water (1.5 mL) and then fractionated repetitively three times by size-exclusion gel filtration chromatography (Sephadex G-25, φ 1.5×45 cm, distilled water). After freeze-drying, the following asparagine-linked asialo oligosaccharide chain glutaric acid (c) (51.4 mg) was obtained (MALDI TOF Mass calculated for [M+Na]+ 1891.66. found 1891.78):

[Formula 20]

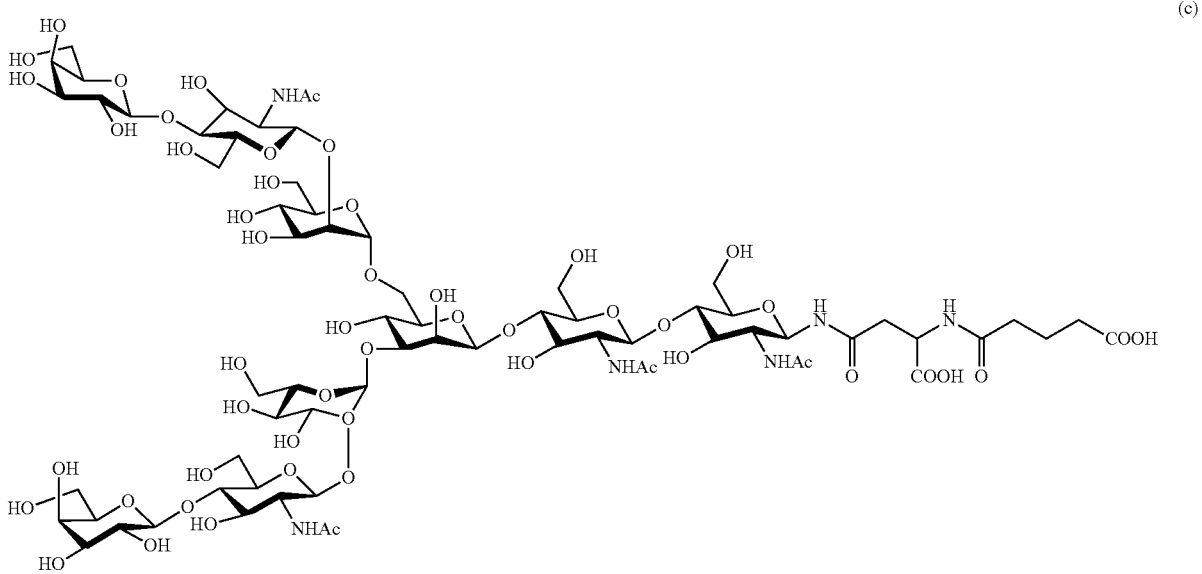

(c)

Example 13

Synthesis of 26Lys-Asialo Oligosaccharide Chain Asn Linker-Modified Arg34GLP-1 (7-37) Peptide (1) Synthesis of Asparagine-Linked Asialo Oligosaccharide Chain Glutaric Acid In a 10-mL eggplant flask, an asparagine-linked asialo oligosaccharide chain (50.6 mg, 28.7 μmol) was dissolved in (2) Synthesis of Asparagine-Linked Asialo Oligosaccharide Chain Glutaric Acid N-Hydroxysuccinimidyl Ester In a 1.5-mL Eppendorf tube, a DMSO solution (25 μL, 11.0 μmol) of 0.44 M N-hydroxysuccinimide and a DMSO solution (75 μL, 27.6 μmol) of 0.37 M EDC were added to a DMSO (200 μL) solution of the asparagine-linked asialo oligosaccharide chain glutaric acid (c) (17.2 mg, 9.2 μmol). After stirring at room temperature for 6 hours, EDC was inactivated by the addition of DTT (5.7 mg, 36.8 μmol) (Grabarek, Z., Gergely, J. Anal. Biochem. 1990, 185, 131-135). This solution mixture containing the following asparagine-linked asialo oligosaccharide chain glutaric acid N-hydroxysuccinimidyl ester (d) was directly used in peptide condensation as a sugar linker reagent (0.03 M solution):

[Formula 21]

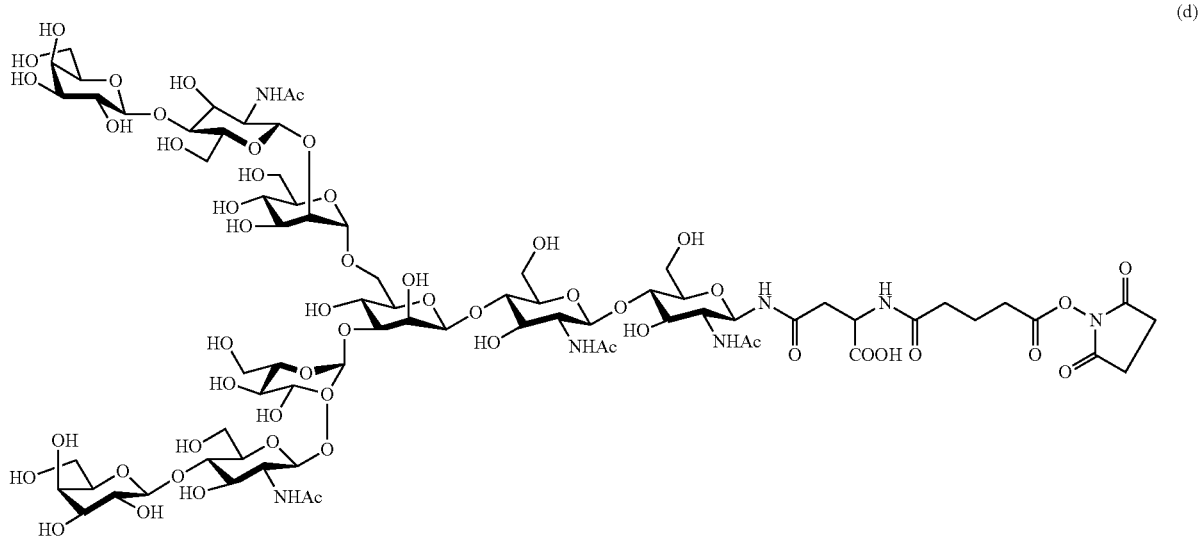

(d)

(3) Synthesis of 26Lys-Asialo Oligosaccharide Chain Asn Linker-Modified Arg34GLP-1 (7-37)

In a 1.5-mL Eppendorf tube, DIPEA (4.8 μL, 27.6 μmol) and the 0.03 M sugar linker reagent prepared above (15.0 μL, 4.5 μmol) were added to a DMSO (300 μL) solution of Lys$^{26}$Arg$^{34}$GLP-1(7-37) synthesized in Synthesis Example 4 (SEQ ID NO: 80) (2.8 mg, 0.83 μmol). After stirring at room temperature for 2 hours, the reaction was terminated by the addition of an aqueous solution (200 μL) of glycine (2 mg, 26.6 μmol). Fractions of peaks at a retention time of 15.5 min were directly collected by HPLC [column: Zorbax 300SB-CN, φ4.6×250 mm, gradient: A solution: 0.1% TFA water, B solution: 0.09% TFA/10% water/90% AN 1.0 ml/min; 10→40% B (0-8 min) 40-+50% B (8-20 min) linear gradient). After freeze-drying, the following 26Lys-asialo oligosaccharide chain Asn linker-modified Arg$^{34}$GLP-1(7-37) (0.7 mg) was obtained (MALDI TOF Mass calculated for [M (average)+H]$^+$ 5236.35. found 5236.1):

[Formula 22]

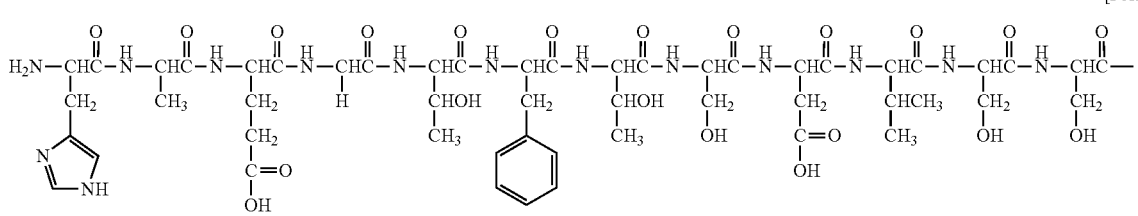

83
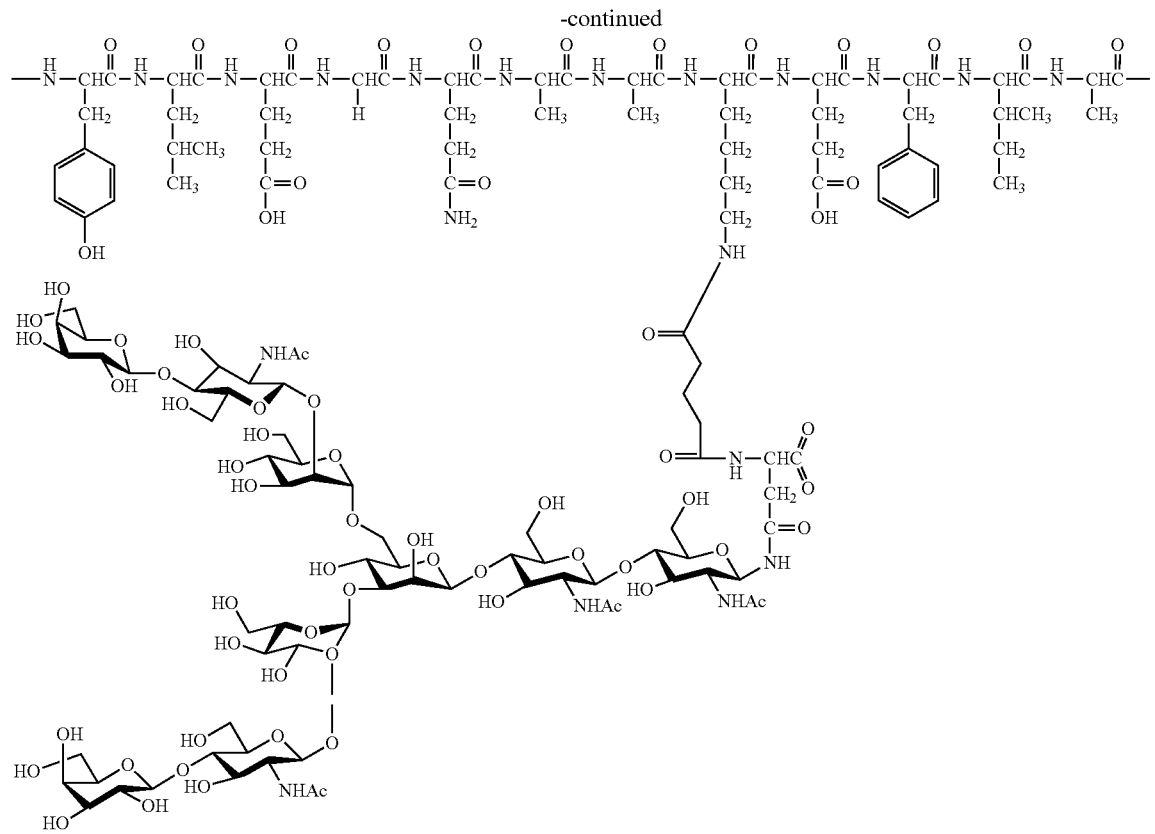
-continued
84
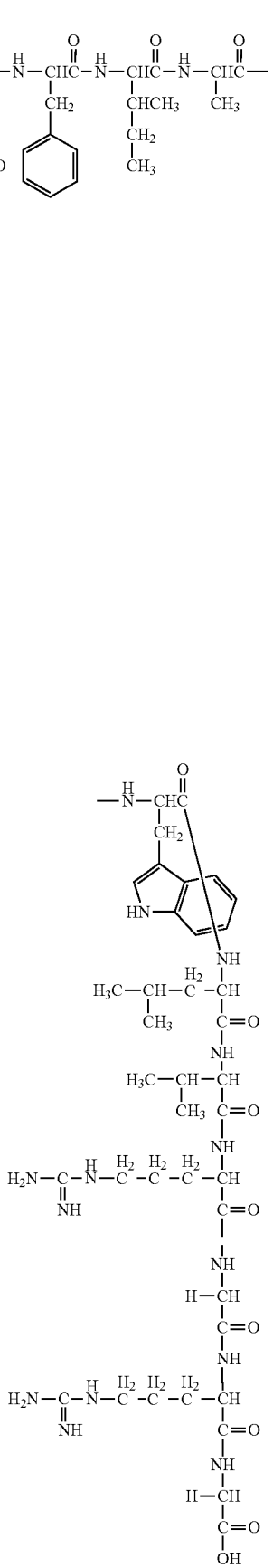

Example 14

Synthesis of 30-Cys-Disialo Oligosaccharide Chain Added Exendin-4

A 39-residue peptide wherein 30Gly of Ex-4 was substituted with Cys (12.0 mg) synthesized in Synthesis Example 5 and bromoacetamidyl disialo oligosaccharide (a) (a product of OTSUKA Chemical Co., Ltd.) (36 mg) were reacted in 100 mM sodium phosphate (pH 7.4) and 5 mM tris(carboxyethyl)phosphine (1 mL) at 37° C. for 1 hour. The reaction solution was directly subjected to purification by HPLC [column: SHISEIDO UG-120 (C18, 5 µm), ϕ20×250 mm, gradient: A solution: 0.1% TFA water, B solution: 0.09% TFA/10% water/90% AN 8 ml/min; 35→50% B, ϕ20 min linear gradient] to obtain 10.6 mg of oligosaccharide chain added Ex-4 peptide wherein 30Gly of Ex-4 was substituted with disialo oligosaccharide chain added Cys (30Cys Ex-4-disialo) (M:$C_{271}H_{422}N_{58}O_{123}S$ MALDI TOF Mass calculated for $[M+H]^+$ 6493.63. found 6494.33).

Example 15

Synthesis of 26Cys-Disialo Oligosaccharide Chain Added BIM51077

A 30-residue peptide wherein 26Lys of BIM51077 was substituted with Cys (2.4 mg, 0.72 µmol) synthesized in Synthesis Example 6 and guanidine (216 mg) were dissolved in distilled water (240 µL), and an aqueous TCEP solution (100 mM, 100 µL), bromoacetamidyl disialo oligosaccharide (a) (10 mg/mL, 100 µL, 4.2 µmol) and 500 mM sodium phosphate buffer (pH 7.4, 100 µL) were added thereto in this order. The mixture was allowed to react at 37° C. for 2 hours. The reaction solution was directly subjected to purification by HPLC [column: SHISEIDO UG-120 (C18, 5 µm), ϕ4.6×250 mm, gradient: A solution: 0.1% TFA water, B solution: 0.09% TFA/10% water/90% AN 0.7 ml/min; 35→60% B, 20 min linear gradient] to obtain 1.9 mg of oligosaccharide chain added BIM51077 peptide wherein 26Lys of BIM51077 was substituted with disialo oligosaccharide chain added Cys (26Cys BIM51077-disialo) (MALDI TOF Mass calculated for $[M\,(average)+H]^+$ 5578.72. found 5578.74).

Example 16

Synthesis of 30Cys-M5 Oligosaccharide Chain Added Exendin-4

A 39-residue peptide wherein 30Gly of Ex-4 was substituted with Cys (1.2 mg) synthesized in Synthesis Example 5 and the bromoacetamidyl M5 oligosaccharide chain (b) synthesized in Example 12 (3.9 mg) were reacted in 35 mM sodium phosphate buffer (pH 7.4) and 1 mM tris(carboxyethyl)phosphine (0.17 mL) at 37° C. for 3 hours. The reaction solution was directly subjected to purification by HPLC [column: SHISEIDO UG-120 (C18, 5 µm), ϕ4.6×250 mm, gradient: A solution: 0.1% TFA water, B solution: 0.09% TFA/10% water/90% AN 0.7 ml/min; 35→50% B, 20 min linear gradient] to obtain 0.5 mg of oligosaccharide chain added Ex-4 peptide wherein 30Gly of Ex-4 was substituted with high-mannose type M5 oligosaccharide chain added Cys (30Cys Ex-4-M5) (M:$C_{233}H_{362}N_{54}O_{97}S$ MALDI TOF Mass calculated for $[M\,(average)+H]^+$ 5504.74. found 5506.85).

Table 5 below shows MS data (MALDI-TOF mass) of the oligosaccharide chain added GLP-1 peptides obtained in Examples 1 to 16.

TABLE 5

| Example | Compound | | Formula | Ion | Calc. | | Found |
|---|---|---|---|---|---|---|---|
| Example 1 | 26,34Cys GLP-1-disialo | Calcurated for | $C_{317}H_{492}N_{52}O_{171}S_2$ | $[M+H]^+$ | 7828.1 | found. | 7828.8 |
| Example 2 | 18,36Cys GLP-1-disialo | Calcurated for | $C_{320}H_{449}N_{51}O_{170}S_2$ | $[M+H]^+$ | 7841.1 | found. | 7845.3 |
| Example 3 | 22,30Cys GLP-1-disialo | Calcurated for | $C_{324}H_{508}N_{54}O_{171}S_2$ | $[M+H]^+$ | 7960.9 | found. | 7960.6 |
| Example 4 | 22,36Cys GLP-1-disialo | Calcurated for | $C_{321}H_{501}N_{51}O_{171}S_2$ | $[M+H]^+$ | 7875.8 | found. | 7876.6 |
| Example 5 | 30,36Cys GLP-1-disialo | Calcurated for | $C_{320}H_{499}N_{51}O_{171}S_2$ | $[M+H]^+$ | 7861.8 | found. | 7860.4 |
| Example 6 | 30Cys GLP-1-HA-4 | Calcurated for | $C_{181}H_{274}N_{43}O_{70}S$ | $[M+H]^+$ | 4201.9 | found. | 4203.5 |
| Example 7 | 30Cys GLP-1-HA-8 | Calcurated for | $C_{209}H_{316}N_{45}O_{92}S$ | $[M+H]^+$ | 4960.1 | found. | 4961.9 |
| Example 8 | 36Cys GLP-1-HA-4 | Calcurated for | $C_{178}H_{267}N_{40}O_{70}S$ | $[M+H]^+$ | 4116.8 | found. | 4118.3 |
| Example 9 | 36Cys GLP-1-HA-8 | Calcurated for | $C_{206}H_{309}N_{42}O_{83}S$ | $[M+H]^+$ | 4875.1 | found. | 4876.9 |
| Example 10 | 30Cys GLP-1-HA-16 | Calcurated for | $C_{265}H_{399}N_{49}O_{136}S$ | $[M+H]+$ | 6476.6 | found. | 6477.8 |
| Example 11 | 36Cys GLP-1-H4-16 | Calcurated for | $C_{262}H_{392}N_{46}O_{136}S$ | $[M+H]+$ | 6391.5 | found. | 6394.1 |
| Example 12 | 36Cys GLP-1-M5 | Calcurated for | $C_{196}H_{300}N_{40}O_{83}S$ | $[M+H]+$ | 4575.0 | found. | 4576.2 |
| Example 13 | 26Lys asialo-Asn-linker | Calcurated for | $C_{222}H_{342}N_{48}O_{97}$ | $[M+H]+$ | 5236.35 | found | 5236.1 |
| Example 14 | 30Cys Ex-4-disialo | Calcurated for | $C_{271}H_{422}N_{58}O_{123}S$ | $[M+H]+$ | 6493.63 | found | 6494.33 |
| Example 15 | 26Cys-BIM51077-disialo | Calcurated for | $C_{235}H_{364}N_{46}O_{107}S$ | $[M+H]+$ | 5578.72 | found | 5578.74 |
| Example 16 | 30Cys Ex-4-M5 | Calcurated for | $C_{233}H_{362}N_{54}O_{97}S$ | $[M+H]+$ | 5504.74 | found | 5506.85 |

Comparative Example 1

A solid-phase synthesis column was charged with Amino-PEGA resin (100 µmol), washed thoroughly with DCM and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in NMP (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu (OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His (Trt) (SEQ ID NO:74) on a solid-phase resin.

After washing with DCM and DMF, the resin equivalent to 5 μmol of the 31-residue peptide was transferred to an Eppendorf tube.

The obtained resin having a peptide formed thereon was partly taken in a solid-phase synthesis column. Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC (Cadenza column C18 100×10 mm, developing solvent A: 0.1% aqueous TFA solution, B: 0.1% TFA acetonitrile:water=90:10, gradient A:B=95:5→5:95, 15 min, flow rate: 3.0 ml/min) to obtain GLP-1.

Synthesis Example 1

Synthesis of Oligo Hyaluronic Acid Oligosaccharide Chain

To 500 mg of hyaluronic acid (a product of Shiseido Co., Ltd., average molecular weight: 1,200,000), 100 ml of acetate buffer (pH 4) was added, and the mixture was well stirred until dissolution. After addition of 2.5 kU of hyaluronidase (a product of CALBIOCHEM, Bovine Testes-derived), the mixture was allowed to react at 37° C. for 2 days. This solution was concentrated and then dissolved again in 45 ml of acetate buffer (pH 4). After addition of 4.5 kU of hyaluronidase (a product of CALBIOCHEM, Bovine Testes-derived), the mixture was allowed to react at 37° C. for additional 2 days. The reaction solution was fractionated using ultrafiltration membranes with molecular weight cutoffs of 3 kDa and 1 kDa (products of Millipore). After freeze-drying, 268.4 mg of hyaluronic acid fractions with a molecular weight of 1 to 3 kDa was obtained.

Since the obtained hyaluronic acid fractions with a molecular weight of 1 to 3 kDa contained several kinds of oligo hyaluronic acids, preparative HPLC was performed for separating them. The oligo hyaluronic acid fractions with a molecular weight of 1 to 3 kDa were dissolved in a small amount of water and fractionated in several portions by HPLC purification [column: Shodex Asahipak NH2P-90 20F 9 μm, φ20.0×300 mm, mobile phase: 180 mM NaH2PO4 aq] to each elution peak. The obtained fractions were desalted by gel filtration and freeze-dried to obtain oligo hyaluronic acids (tetrasaccharide to octadecasaccharide). The yield of each oligo hyaluronic acid is shown below.

Oligo hyaluronic acid tetrasaccharide 22.5 mg ($t_R$=10.0 min)

Oligo hyaluronic acid hexasaccharide 51.1 mg ($t_R$=11.8 min)

Oligo hyaluronic acid octasaccharide 52.7 mg ($t_R$=14.0 min)

Oligo hyaluronic acid decasaccharide 27.0 mg ($t_R$=17.0 min)

Oligo hyaluronic acid dodecasaccharide 9.6 mg ($t_R$=21.4 min)

Oligo hyaluronic acid tetradecasaccharide 7.8 mg ($t_R$=27.6 min)

Oligo hyaluronic acid hexadecasaccharide 4.1 mg ($t_R$=36.0 min)

Oligo hyaluronic acid octadecasaccharide 2.0 mg ($t_R$=47.4 min)

Synthesis Example 2

Synthesis of Peptide Wherein Position 30 of GLP-1 was Substituted with Cys

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Cys(Trt), Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu (OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Cys(Trt)-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:75) on a solid-phase resin.

The obtained resin having a peptide formed thereon was partly taken in a solid-phase synthesis column.

Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 µm), φ20×250 mm, gradient: A solution: 0.1% TFA water, B solution: 0.09% TFA/10% water/90% AN 8.0 ml/min; 35→60% B, 20 min linear gradient] to obtain a 31-residue peptide wherein 30Ala of GLP-1 was substituted with Cys (SEQ ID NO: 76).

Synthesis Example 3

Synthesis of Peptide Wherein Position 36 of GLP-1 was Substituted with Cys

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Cys(Trt), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Cys(Trt)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO: 77) on a solid-phase resin.

The obtained resin having a peptide formed thereon was partly taken in a solid-phase synthesis column. Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% B, 20 min linear gradient] to obtain a 31-residue peptide wherein 36Arg of GLP-1 is substituted by Cys (SEQ ID NO: 78).

Synthesis Example 4

Synthesis of Peptide Wherein Position 34 of GLP-1 was Substituted with Arg

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU.HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Arg(Pbf), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Arg(Pbf)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:79) on a solid-phase resin.

The obtained resin having a peptide formed thereon was partly taken in a solid-phase synthesis column. Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 µm), φ 20×250 mm, gradient: A solution: 0.1% TFA water, B solution: 0.09% TFA/10% water/90% AN 8.0 ml/min; 35→60% B, 20 min linear gradient] to obtain a 31-residue peptide wherein 34Lys of GLP-1 was substituted with Arg (SEQ ID NO: 80).

Synthesis Example 5

Synthesis of Peptide Wherein Position 30 of Exendin-4 was Substituted with Cys

A solid-phase synthesis column was charged with Rink-Amide-PEGA resin (100 µmol) (product of Merck) and washed with DMF. Then, amino acids were sequentially condensed in accordance with the method shown below to extend a peptide chain.

The amino acid (0.5 mmol) having an amino group protected with Fmoc group was dissolved in 0.45 M HCTU-.HOBT/NMP (2.5 mmol), and the resulting mixture was loaded to a solid-phase synthesis column. Subsequently, 0.9 M DIPEA/NMP (2.5 mmol) was added thereto. After stirring at room temperature for 20 minutes, the resin was washed with DCM and DMF, and Fmoc group was removed by using a 20% piperidine/DMF solution (2 ml) for 15 minutes. This operation was repeatedly performed to sequentially condense amino acids.

Fmoc-Ser(tBu), Fmoc-Pro, Fmoc-Pro, Fmoc-Pro, Fmoc-Ala, Fmoc-Gly, Fmoc-Ser(tBu), Fmoc-Ser(tBu), Fmoc-Pro, Fmoc-Cys(Trt), Fmoc-Gly, Fmoc-Asn(Trt), Fmoc-Lys(Boc), Fmoc-Leu, Fmoc-Trp(Boc), Fmoc-Glu(OtBu), Fmoc-Ile, Fmoc-Phe, Fmoc-Leu, Fmoc-Arg(Pbf), Fmoc-Val, Fmoc-Ala, Fmoc-Glu(OtBu), Fmoc-Glu(OtBu), Fmoc-Glu(OtBu), Fmoc-Met, Fmoc-Gln(Trt), Fmoc-Lys(Boc), Fmoc-Ser(tBu), Fmoc-Leu, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Gly and Fmoc-His(Trt) were used as the amino acids protected by Fmoc group to obtain a 39-residue peptide of Ser(tBu)—Pro-Pro-Pro-Ala-Gly-Ser(tBu)-Ser(tBu)-Pro-Cys(Trt)-Gly -Asn(Trt)-Lys(Boc)-Leu-Trp(Boc)-Glu(OtBu)-Ile-Phe-Leu -Arg(Pbf)-Val-Ala-Glu(OtBu)-Glu(OtBu)-Glu(OtBu)-Met -Gln(Trt)-Lys(Boc)-Ser(tBu)-Leu-Asp(OtBu)-Ser(tBu)-Thr(tBu) -Phe-Thr(tBu)-Gly-Glu(OtBu)-Gly-His(Trt) (SEQ ID NO: 81) on a solid-phase resin.

The obtained resin having a peptide formed thereon was partly taken in a solid-phase synthesis column.

Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 µm), φ20×250 mm, gradient: A solution: 0.1%

TFA water, B solution: 0.09% TFA/10% water/90% AN 8.0 ml/min; 35→60% B, 20 min linear gradient] to obtain a 39-residue peptide wherein 30Gly of Ex-4 was substituted with Cys (MALDI TOF Mass calculated for [M+H]+ 4230.60. found 4231.27) (SEQ ID NO: 82).

Synthesis Example 6

Synthesis of Peptide Wherein Position 26 of GLP-1 was Substituted with Cys

A solid-phase synthesis column was charged with Rink-Amido-PEGA resin (100 µmol) (product of Merck) and washed with DMF. Then, amino acids were sequentially condensed in accordance with the method shown below to extend a peptide chain.

The amino acid (0.5 mmol) having an amino group protected with Fmoc group was dissolved in 0.45 M HCTU-.HOBT/NMP (2.5 mmol), the resulting mixture was loaded to a solid-phase synthesis column. Subsequently, 0.9 M DIPEA/NMP (2.5 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed to sequentially condense amino acids.

Fmoc-Arg(Pbf), Fmoc-Aminoisobutyric Acid(Aib), Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Cys(Trt), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Aib and Fmoc-His(Trt) were used as the amino acids protected by Fmoc group to obtain a 30-residue peptide of Arg(Pbf)-Aib-Lys(Boc)-Val-Leu-Trp(Boc)-Ala-Ile-Phe-Glu(OtBu)-Cys(Trt)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Aib-His(Trt) (SEQ ID NO:83) on a solid-phase resin.

The obtained resin having a peptide formed thereon was partly taken in a solid-phase synthesis column. Trifluoroacetic acid:water: TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18, 5 µm), φ 20×250 mM, gradient: A solution: 0.1% TFA water, B solution: 0.09% TFA/10% water/90% AN 8.0 ml/min; 35→60% B, 20 min linear gradient] to obtain 12 mg of a 30-residue peptide wherein 26Lys of BIM51077 was substituted with Cys (MALDI TOF Mass calculated for [M (average)+H]+ 3315.69. found 3314.72) (SEQ ID NO: 84).

The oligosaccharide chain added GLP-1 peptides produced in each Example above are oligosaccharide chain added GLP-1 peptides having the sequence of His$_7$-Ala$_8$-Glu$_9$-Gly$_{10}$-Thr$_{11}$-Phe$_{12}$-Thr$_{13}$-Ser$_{14}$-Asp$_{15}$-Val$_{16}$-Ser$_{17}$-Ser$_{18}$-Tyr$_{19}$-Leu$_{20}$-Glu$_{21}$-Gly$_{22}$-Gln$_{23}$-Ala$_{24}$-Ala$_{25}$-LYs$_{26}$-Glu$_{27}$-Phe$_{28}$-Ile$_{29}$-Ala$_{30}$-Trp$_{31}$-Leu$_{32}$-Val$_{33}$-Lys$_{34}$-Gly$_{35}$-Arg$_{36}$-Gly$_{37}$ (SEQ ID NO: 2, GLP-1) wherein:

(b1) 26Lys and 34Lys are each substituted with disialo oligosaccharide chain added Cys (Example 1) (SEQ ID NO: 54);

(b2) 18Ser and 36Arg are each substituted with disialo oligosaccharide chain added Cys (Example 2) (SEQ ID NO: 55);

(b3) 22Gly and 30Ala are each substituted with disialo oligosaccharide chain added Cys (Example 3) (SEQ ID NO: 56);

(b4) 22Gly and 36Arg are each substituted with disialo oligosaccharide chain added Cys (Example 4) (SEQ ID NO: 57);

(b5) 30Ala and 36Arg are each substituted with disialo oligosaccharide chain added Cys (Example 5) (SEQ ID NO: 58);

(b6) 30Ala is substituted with hyaluronic acid tetrasaccharide (HA-4) added Cys (Example 6) (SEQ ID NO: 59);

(b7) 30Ala is substituted with hyaluronic acid octasaccharide (HA-8) added Cys (Example 7) (SEQ ID NO: 60);

(b8) 36Arg is substituted with hyaluronic acid tetrasaccharide (HA-4) added Cys (Example 8) (SEQ ID NO: 61);

(b9) 36Arg is substituted with hyaluronic acid octasaccharide (HA-8) added Cys (Example 9) (SEQ ID NO: 62);

(b10) 30Ala is substituted with hyaluronic acid hexadecasaccharide (HA-16) added Cys (Example 10) (SEQ ID NO: 63);

(b11) 36Arg is substituted with hyaluronic acid hexadecasaccharide (HA-16) added Cys (Example 11) (SEQ ID NO: 64);

(b12) 36Arg is substituted with high-mannose type oligosaccharide chain (M5) added Cys (Example 12) (SEQ ID NO: 65); and (b13) asialo oligosaccharide chain added Asn is linked to 26Lys via a linker (Example 13) (SEQ ID NO: 66), and are also (b14) an oligosaccharide chain added GLP-1 peptide having the sequence of
H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO: 50, exendin-4) wherein
30Gly is substituted with disialo oligosaccharide chain added Cys (Example 14) (SEQ ID NO: 67);

(b15) an oligosaccharide chain added GLP-1 peptide having the sequence of
His-R2-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-R2-Arg-NH$_2$ wherein R2 represents α-methylalanine (SEQ ID NO: 52, BIM51077) wherein
26Lys is substituted with disialo oligosaccharide chain added Cys (Example 15) (SEQ ID NO: 68); and (b16) an oligosaccharide chain added GLP-1 peptide having the sequence of exendin-4 (SEQ ID NO: 50) wherein 30Gly is substituted with high-mannose type oligosaccharide chain (M5) added Cys (Example 16).

Some of the peptides of Examples 1 to 15 were subjected to Test Examples 1 and/or 2 below.

Test Example 1

Test of Resistance to Dipeptidyl Peptidase IV (DPP-IV)

17.7 nmol of the oligosaccharide chain added GLP-1 peptide prepared in each Example or the GLP-1 prepared in Comparative Example 1 was added together with 2.2 mU of DPP-IV (dipeptidyl peptidase IV from porcine kidney, product of SIGMA) to a 0.5-ml Eppendorf tube. Each solution mixture was adjusted with 100 mM sodium phosphate buffer to 100 μl in total and allowed to react at 37° C. A 10 μl aliquot of the reaction solution was mixed with 15 μl of 10% trifluoroacetic acid prepared in advance in another Eppendorf tube. 20 μl thereof was injected into HPLC to monitor complete consumption of raw materials (HPLC conditions: column: SHISEIDO CAPCELPAK C18 UG120, φ4.6×250 mm, developing solvent A: 0.1% aqueous TFA solution, developing solvent B: 0.09% TFA acetonitrile/water=90/10, gradient A/B=65/30→30/60, 20 min, flow rate: 0.7 ml/min). The half-life (t1/2), which serves as an index for resistance to DPP-IV, of the GLP-1 without oligosaccharide chain addition of Comparative Example 1 was defined as a standard (=1). A typical value evaluated on the oligosaccharide chain added GLP-1 peptide of each Example is shown in Table 6.

TABLE 6

| Compound | | Relative Resistance |
|---|---|---|
| Example 1 | 26,34Cys GLP-1-disialo | 23.6 |
| Example 2 | 18,36Cys GLP-1-disialo | 128.6 |
| Example 3 | 22,30Cys GLP-1-disialo | 32.5 |
| Example 4 | 22,36Cys CLP-1-disialo | 22.5 |
| Example 5 | 30,36Cys GLP-1-disialo | 7.5 |
| Example 6 | 30Cys GLP-1-HA-4 | 2.1 |
| Example 7 | 30Cys GLP-1-HA-8 | 3.4 |
| Example 8 | 36Cys GLP-1-HA-4 | 2.2 |
| Example 9 | 36Cys GLP-1-HA-8 | 3 |
| Example 10 | 30Cys GLP-1-HA-16 | 3.9 |
| Example 11 | 36Cys GLP-1-HA-16 | 3 |
| Example 13 | 26Lys GLP-1-linker-asialo | 5.7 |

The oligosaccharide chain added GLP-1 peptide of each Example exhibited DPP-IV resistance 2.1 to 128 times that of the GLP-1 of Comparative Example 1.

Test Example 2

Oral Glucose Tolerance Test (OGTT)

A PBS solution of the oligosaccharide chain added GLP-1 peptide prepared in each Example or the GLP-1 prepared in Comparative Example 1 was intraperitoneally administered at a dose of 10 ml/kg to C57BL/6JJcl mice (10 week old, male) fasted overnight. After 30 minutes, a glucose solution was orally administered at a dose of 1 mg/g. Blood was collected from the orbits before the glucose administration and 30 minutes, 60 minutes and 120 minutes after the glucose administration. Blood-sugar levels were measured using ACCU-CHEK Aviva (Roche Diagnostics). Typical results are shown in FIGS. 1 to 4. In the drawings below, for example, "26,34Cys GLP-1-disialo", which is an oligosaccharide chain added GLP-1 peptide wherein amino acids at positions 26 and 34 of GLP-1 are each substituted with disialo oligosaccharide chain added Cys, is referred to as "C26,C34", if necessary. The same holds true for other oligosaccharide chains and amino acid sites.

Figure 5:
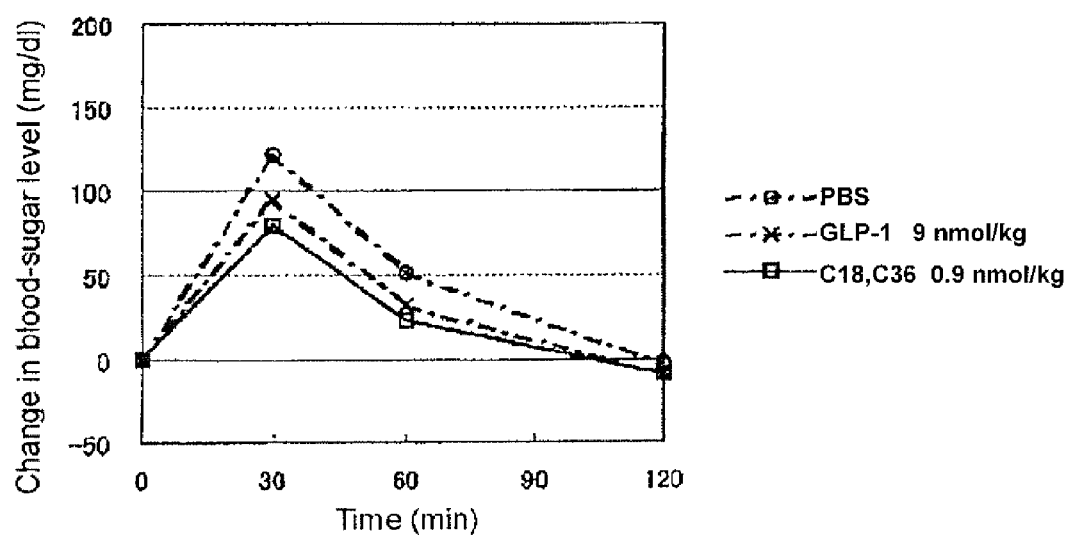
FIG. 5 shows the results of Oral Glucose Tolerance Test (OGTT) conducted for examining the influence of the dose of the oligosaccharide chain added GLP-1 peptide on the effect of suppressing rise in blood-sugar levels. The 18 and 36Cys-disialo oligosaccharide chain added GLP-1 is administered at a dose of 0.9 nmol/kg, while GLP-1 is administered at a dose of 9 nmol/kg.

Next, 18,36Cys GLP-1-disialo and GLP-1 were evaluated by OGTT using doses of 1/10 (0.9 nmol/kg) and 9 nmol/kg, respectively, and compared. The results are shown in FIG. 5.

The 18,36Cys GLP-1-disialo administered at a dose of 0.9 nmol/kg exhibited almost equal effect of suppressing rise in blood-sugar levels to that of GLP-1 administered at a dose of 9 nmol/kg. The 18,36Cys GLP-1-disialo had the effect of suppressing rise in blood-sugar levels about 10 times that of GLP-1.

Sequence Listing Free Text

SEQ ID NO: 1 is oligosaccharide chain added GLP-1 peptide represented by the general formula (1).

SEQ ID NO: 2 is GLP-1 (7-37).
SEQ ID NO: 3 is GLP-1 (7-36) NH$_2$.
SEQ ID NO: 4 is oligosaccharide chain added GLP-1 peptide represented by (a1).
SEQ ID NO: 5 is oligosaccharide chain added GLP-1 peptide represented by (a2).
SEQ ID NO: 6 is oligosaccharide chain added GLP-1 peptide represented by (a3).
SEQ ID NO: 7 is oligosaccharide chain added GLP-1 peptide represented by (a4).
SEQ ID NO: 8 is oligosaccharide chain added GLP-1 peptide represented by (a5).
SEQ ID NO: 9 is oligosaccharide chain added GLP-1 peptide represented by (a6).
SEQ ID NO: 10 is oligosaccharide chain added GLP-1 peptide represented by (a7).
SEQ ID NO: 11 is oligosaccharide chain added GLP-1 peptide represented by (a8).
SEQ ID NO: 12 is oligosaccharide chain added GLP-1 peptide represented by (a9).
SEQ ID NO: 13 is oligosaccharide chain added GLP-1 peptide represented by (a10).
SEQ ID NO: 14 is oligosaccharide chain added GLP-1 peptide represented by (a11).
SEQ ID NO: 15 is oligosaccharide chain added GLP-1 peptide represented by (a12).
SEQ ID NO: 16 is oligosaccharide chain added GLP-1 peptide represented by (a13).
SEQ ID NO: 17 is oligosaccharide chain added GLP-1 peptide represented by (a14).
SEQ ID NO: 18 is oligosaccharide chain added GLP-1 peptide represented by (a15).
SEQ ID NO: 19 is oligosaccharide chain added GLP-1 peptide represented by (a16).
SEQ ID NO: 20 is oligosaccharide chain added GLP-1 peptide represented by (a17).
SEQ ID NO: 21 is oligosaccharide chain added GLP-1 peptide represented by (a18).
SEQ ID NO: 22 is oligosaccharide chain added GLP-1 peptide represented by (a19).
SEQ ID NO: 23 is oligosaccharide chain added GLP-1 peptide represented by (a20).
SEQ ID NO: 24 is oligosaccharide chain added GLP-1 peptide represented by (a21).
SEQ ID NO: 25 is oligosaccharide chain added GLP-1 peptide represented by (a22).
SEQ ID NO: 26 is oligosaccharide chain added GLP-1 peptide represented by (a23).
SEQ ID NO: 27 is oligosaccharide chain added GLP-1 peptide represented by (a24).
SEQ ID NO: 28 is oligosaccharide chain added GLP-1 peptide represented by (a25).
SEQ ID NO: 29 is oligosaccharide chain added GLP-1 peptide represented by (a26).
SEQ ID NO: 30 is oligosaccharide chain added GLP-1 peptide represented by (a27).
SEQ ID NO: 31 is oligosaccharide chain GLP-1 peptide represented by (a28).
SEQ ID NO: 32 is oligosaccharide chain added GLP-1 peptide represented by (a29).
SEQ ID NO: 33 is oligosaccharide chain added GLP-1 peptide represented by (a30).
SEQ ID NO: 34 is oligosaccharide chain added GLP-1 peptide represented by (a31).
SEQ ID NO: 35 is oligosaccharide chain added GLP-1 peptide represented by (a32).
SEQ ID NO: 36 is oligosaccharide chain added GLP-1 peptide represented by (a33).
SEQ ID NO: 37 is oligosaccharide chain added GLP-1 peptide represented by (a34).
SEQ ID NO: 38 is oligosaccharide chain added GLP-1 peptide represented by (a35).
SEQ ID NO: 39 is oligosaccharide chain added GLP-1 peptide represented by (a36).
SEQ ID NO: 40 is oligosaccharide chain added GLP-1 peptide represented by (a37).
SEQ ID NO: 41 is oligosaccharide chain added GLP-1 peptide represented by (a38).
SEQ ID NO: 42 is oligosaccharide chain added GLP-1 peptide represented by (a39).
SEQ ID NO: 43 is oligosaccharide chain added GLP-1 peptide represented by (a40).
SEQ ID NO: 44 is oligosaccharide chain added GLP-1 peptide represented by (a41).
SEQ ID NO: 45 is oligosaccharide chain added GLP-1 peptide represented by (a42).
SEQ ID NO: 46 is oligosaccharide chain added GLP-1 peptide represented by (a43).
SEQ ID NO: 47 is oligosaccharide chain added GLP-1 peptide represented by (a44).
SEQ ID NO: 48 is oligosaccharide chain added GLP-1 peptide represented by (a45).
SEQ ID NO: 49 is oligosaccharide chain added GLP-1 peptide represented by (a46).
SEQ ID NO: 50 is exendin-4.
SEQ ID NO: 51 is oligosaccharide chain added exendin-4 represented by the general formula (2).
SEQ ID NO: 52 is BIM51077.
SEQ ID NO: 53 is oligosaccharide chain added BIM51077 represented by the general formula (3).
SEQ ID NO: 54 is oligosaccharide chain added GLP-1 peptide represented by (b1).
SEQ ID NO: 55 is oligosaccharide chain added GLP-1 peptide represented by (b2).
SEQ ID NO: 56 is oligosaccharide chain added GLP-1 peptide represented by (b3).
SEQ ID NO: 57 is oligosaccharide chain added GLP-1 peptide represented by (b4).
SEQ ID NO: 58 is oligosaccharide chain added GLP-1 peptide represented by (b5).
SEQ ID NO: 59 is oligosaccharide chain added GLP-1 peptide represented by (b6).
SEQ ID NO: 60 is oligosaccharide chain added GLP-1 peptide represented by (b7).
SEQ ID NO: 61 is oligosaccharide chain added GLP-1 peptide represented by (b8).
SEQ ID NO: 62 is oligosaccharide chain added GLP-1 peptide represented by (b9).
SEQ ID NO: 63 is oligosaccharide chain added GLP-1 peptide represented by (b10).
SEQ ID NO: 64 is oligosaccharide chain added GLP-1 peptide represented by (b11).
SEQ ID NO: 65 is oligosaccharide chain added GLP-1 peptide represented by (b12).
SEQ ID NO: 66 is oligosaccharide chain added GLP-1 peptide represented by (b13).
SEQ ID NO: 67 is oligosaccharide chain added exendin-4 represented by (b14).
SEQ ID NO: 68 is oligosaccharide chain added BIM51077 represented by (b15).
SEQ ID NO: 69 is 31-residue peptide with protective groups synthesized in Example 1.

SEQ ID NO: 70 is 31-residue peptide with protective groups synthesized in Example 2.
SEQ ID NO: 71 is 31-residue peptide with protective groups synthesized in Example 3.
SEQ ID NO: 72 is 31-residue peptide with protective groups synthesized in Example 4.
SEQ ID NO: 73 is 31-residue peptide with protective groups synthesized in Example 5.
SEQ ID NO: 74 is 31-residue peptide with protective groups synthesized in Comparative Example 1.
SEQ ID NO: 75 is 31-residue peptide with protective groups synthesized in Synthesis Example 2.
SEQ ID NO: 76 is 31-residue peptide synthesized in Synthesis Example 2.
SEQ ID NO: 77 is 31-residue peptide with protective groups synthesized in Synthesis Example 3.
SEQ ID NO: 78 is 31-residue peptide synthesized in Synthesis Example 3.
SEQ ID NO: 79 is 31-residue peptide with protective groups synthesized in Synthesis Example 4.
SEQ ID NO: 80 is 31-residue peptide synthesized in Synthesis Example 4.
SEQ ID NO: 81 is 39-residue peptide with protective groups synthesized in Synthesis Example 5.
SEQ ID NO: 82 is 39-residue peptide synthesized in Synthesis Example 5.
SEQ ID NO: 83 is 30-residue peptide with protective groups synthesized in Synthesis Example 6.
SEQ ID NO: 83 is 30-residue peptide synthesized in Synthesis Example 6.

INDUSTRIAL APPLICABILITY

The present invention provides an oligosaccharide chain added GLP-1 peptide that has higher stability in blood than that of GLP-1 and, preferably, exhibits higher activity of controlling blood-sugar levels than that of GLP-1. The present invention is useful particularly in pharmaceutical field.

SEQUENCE LISTING

```
<160> NUMBER OF SEQ ID NOS: 84

<210> SEQ ID NO 1
<211> LENGTH: 31
<212> TYPE: PRT
<213> ORGANISM: artificial sequence
<220> FEATURE:
<223> OTHER INFORMATION: glycosylated GLP-1 peptide
<220> FEATURE:
<221> NAME/KEY: MISC_FEATURE
<222> LOCATION: (12)..(12)
<223> OTHER INFORMATION: Xaa18: Ser, glycosylated Cys or glycosylated
      Asn.
<220> FEATURE:
<221> NAME/KEY: MISC_FEATURE
<222> LOCATION: (13)..(13)
<223> OTHER INFORMATION: Xaa19: Tyr, glycosylated Cys or glycosylated
      Asn.
<220> FEATURE:
<221> NAME/KEY: MISC_FEATURE
<222> LOCATION: (16)..(16)
<223> OTHER INFORMATION: Xaa22: Gly, glycosylated Cys or glycosylated
      Asn.
<220> FEATURE:
<221> NAME/KEY: MISC_FEATURE
<222> LOCATION: (20)..(20)
<223> OTHER INFORMATION: Xaa26: Lys, glycosylated Cys or glycosylated
      Asn.
<220> FEATURE:
<221> NAME/KEY: MISC_FEATURE
<222> LOCATION: (24)..(24)
<223> OTHER INFORMATION: Xaa30: Ala, glycosylated Cys or glycosylated
      Asn.
<220> FEATURE:
<221> NAME/KEY: MISC_FEATURE
<222> LOCATION: (28)..(28)
<223> OTHER INFORMATION: Xaa34: Lys, glycosylated Cys or glycosylated
      Asn.
<220> FEATURE:
<221> NAME/KEY: MISC_FEATURE
<222> LOCATION: (30)..(30)
<223> OTHER INFORMATION: Xaa36: Arg, glycosylated Cys or glycosylated
      Asn.
<220> FEATURE:
<221> NAME/KEY: MISC_FEATURE
<222> LOCATION: (31)..(31)
<223> OTHER INFORMATION: Xaa37: Gly, -NH2, Gly-glycosylated Cys or
      Gly-glycosylated Asn.
<220> FEATURE:
<221> NAME/KEY: MISC_FEATURE
<222> LOCATION: (31)..(31)
<223> OTHER INFORMATION: When Xaa18 is Ser, Xaa19 is Tyr, Xaa22 is Gly,
```

Xaa26 is Lys, Xaa30 is Ala, Xaa34 is Lys and Xaa36 is Arg,
    Xaa37 is Gly-glycosylated Cys or Gly-glycosylated Asn.

<400> SEQUENCE: 1

His Ala Glu Gly Thr Phe Thr Ser Asp Val Ser Xaa Xaa Leu Glu Xaa
1               5                   10                  15

Gln Ala Ala Xaa Glu Phe Ile Xaa Trp Leu Val Xaa Gly Xaa Xaa
            20                  25                  30

<210> SEQ ID NO 2
<211> LENGTH: 31
<212> TYPE: PRT
<213> ORGANISM: human
<220> FEATURE:
<223> OTHER INFORMATION: GLP-1(7-37)OH

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 30
<212> TYPE: PRT
<213> ORGANISM: artificial sequence
<220> FEATURE:
<223> OTHER INFORMATION: GLP-1(7-36)NH2
<220> FEATURE:
<221> NAME/KEY: MOD_RES
<222> LOCATION: (30)..(30)
<223> OTHER INFORMATION: AMIDATION

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: artificial sequence
<220> FEATURE:
<223> OTHER INFORMATION: amino acid sequence of (a1)
<220> FEATURE:
<221> NAME/KEY: CARBOHYD
<222> LOCATION: (12)..(12)
<223> OTHER INFORMATION: Synthetic

<400> SEQUENCE: 4

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
<211> LENGTH: 31
<212> TYPE: PRT
<213> ORGANISM: artificial sequence
<220> FEATURE:
<223> OTHER INFORMATION: amino acid sequence of (a2)
<220> FEATURE:
<221> NAME/KEY: CARBOHYD
<222> LOCATION: (16)..(16)
<223> OTHER INFORMATION: Synthetic

```
<400> SEQUENCE: 5

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: artificial sequence
<220> FEATURE:
<223> OTHER INFORMATION: amino acid sequence of (a3)
<220> FEATURE:
<221> NAME/KEY: CARBOHYD
<222> LOCATION: (20)..(20)
<223> OTHER INFORMATION: Synthetic

<400> SEQUENCE: 6

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Lys Gly Arg Gly
            20                  25                  30

<210> SEQ ID NO 7
<211> LENGTH: 31
<212> TYPE: PRT
<213> ORGANISM: artificial sequence
<220> FEATURE:
<223> OTHER INFORMATION: amino acid sequence of (a4)
<220> FEATURE:
<221> NAME/KEY: CARBOHYD
<222> LOCATION: (24)..(24)
<223> OTHER INFORMATION: Synthetic

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 8
<211> LENGTH: 31
<212> TYPE: PRT
<213> ORGANISM: artificial sequence
<220> FEATURE:
<223> OTHER INFORMATION: amino acid sequence of (a5)
<220> FEATURE:
<221> NAME/KEY: CARBOHYD
<222> LOCATION: (28)..(28)
<223> OTHER INFORMATION: Synthetic

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30

<210> SEQ ID NO 9
<211> LENGTH: 31
<212> TYPE: PRT
<213> ORGANISM: artificial sequence
<220> FEATURE:
<223> OTHER INFORMATION: amino acid sequence of (a6)
<220> FEATURE:
<221> NAME/KEY: CARBOHYD
<222> LOCATION: (30)..(30)
<223> OTHER INFORMATION: Synthetic
```

-continued

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 10
<211> LENGTH: 32
<212> TYPE: PRT
<213> ORGANISM: artificial sequence
<220> FEATURE:
<223> OTHER INFORMATION: amino acid sequence of (a7)
<220> FEATURE:
<221> NAME/KEY: CARBOHYD
<222> LOCATION: (32)..(32)
<223> OTHER INFORMATION: Synthetic

<400> SEQUENCE: 10

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Cys
            20                  25                  30

<210> SEQ ID NO 11
<211> LENGTH: 31
<212> TYPE: PRT
<213> ORGANISM: artificial sequence
<220> FEATURE:
<223> OTHER INFORMATION: amino acid sequence of (a8)
<220> FEATURE:
<221> NAME/KEY: CARBOHYD
<222> LOCATION: (13)..(13)
<223> OTHER INFORMATION: Synthetic

<400> SEQUENCE: 11

His Ala Glu Gly Thr Phe Thr Ser Asp Val Ser Ser Cys Leu Glu Gly
1               5                   10                  15

Gln Ala Ala Lys Glu Phe Ile Ala Trp Leu Val Lys Gly Arg Gly
            20                  25                  30

<210> SEQ ID NO 12
<211> LENGTH: 31
<212> TYPE: PRT
<213> ORGANISM: artificial sequence
<220> FEATURE:
<223> OTHER INFORMATION: amino acid sequence of (a9)
<220> FEATURE:
<221> NAME/KEY: CARBOHYD
<222> LOCATION: (12)..(12)
<223> OTHER INFORMATION: Synthetic

<400> SEQUENCE: 12

His Ala Glu Gly Thr Phe Thr Ser Asp Val Ser Asn Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 13
<211> LENGTH: 31
<212> TYPE: PRT
<213> ORGANISM: artificial sequence
<220> FEATURE:
<223> OTHER INFORMATION: amino acid sequence of (a11)
<220> FEATURE:
<221> NAME/KEY: CARBOHYD
<222> LOCATION: (16)..(16)

<223> OTHER INFORMATION: Synthetic

<400> SEQUENCE: 13

His Ala Glu Gly Thr Phe Thr Ser Asp Val Ser Ser Tyr Leu Glu Asn
1               5                   10                  15

Gln Ala Ala Lys Glu Phe Ile Ala Trp Leu Val Lys Gly Arg Gly
            20                  25                  30

<210> SEQ ID NO 14
<211> LENGTH: 31
<212> TYPE: PRT
<213> ORGANISM: artificial sequence
<220> FEATURE:
<223> OTHER INFORMATION: amino acid sequence of (a11)
<220> FEATURE:
<221> NAME/KEY: CARBOHYD
<222> LOCATION: (20)..(20)
<223> OTHER INFORMATION: Synthetic

<400> SEQUENCE: 14

His Ala Glu Gly Thr Phe Thr Ser Asp Val Ser Ser Tyr Leu Glu Gly
1               5                   10                  15

Gln Ala Ala Asn Glu Phe Ile Ala Trp Leu Val Lys Gly Arg Gly
            20                  25                  30

<210> SEQ ID NO 15
<211> LENGTH: 31
<212> TYPE: PRT
<213> ORGANISM: artificial sequence
<220> FEATURE:
<223> OTHER INFORMATION: amino acid sequence of (a12)
<220> FEATURE:
<221> NAME/KEY: CARBOHYD
<222> LOCATION: (24)..(24)
<223> OTHER INFORMATION: Synthetic

<400> SEQUENCE: 15

His Ala Glu Gly Thr Phe Thr Ser Asp Val Ser Ser Tyr Leu Glu Gly
1               5                   10                  15

Gln Ala Ala Lys Glu Phe Ile Asn Trp Leu Val Lys Gly Arg Gly
            20                  25                  30

<210> SEQ ID NO 16
<211> LENGTH: 31
<212> TYPE: PRT
<213> ORGANISM: artificial sequence
<220> FEATURE:
<223> OTHER INFORMATION: amino acid sequence of (a13)
<220> FEATURE:
<221> NAME/KEY: CARBOHYD
<222> LOCATION: (28)..(28)
<223> OTHER INFORMATION: Synthetic

<400> SEQUENCE: 16

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Asn Gly Arg Gly
            20                  25                  30

<210> SEQ ID NO 17
<211> LENGTH: 31
<212> TYPE: PRT
<213> ORGANISM: artificial sequence
<220> FEATURE:
<223> OTHER INFORMATION: amino acid sequence of (a14)
<220> FEATURE:
<221> NAME/KEY: CARBOHYD

```
<222> LOCATION: (30)..(30)
<223> OTHER INFORMATION: Synthetic

<400> SEQUENCE: 17

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Asn Gly
            20                  25                  30

<210> SEQ ID NO 18
<211> LENGTH: 32
<212> TYPE: PRT
<213> ORGANISM: artificial sequence
<220> FEATURE:
<223> OTHER INFORMATION: amino acid sequence of (a15)
<220> FEATURE:
<221> NAME/KEY: CARBOHYD
<222> LOCATION: (32)..(32)
<223> OTHER INFORMATION: Synthetic

<400> SEQUENCE: 18

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Asn
            20                  25                  30

<210> SEQ ID NO 19
<211> LENGTH: 31
<212> TYPE: PRT
<213> ORGANISM: artificial sequence
<220> FEATURE:
<223> OTHER INFORMATION: amino acid sequence of (a16)
<220> FEATURE:
<221> NAME/KEY: CARBOHYD
<222> LOCATION: (13)..(13)
<223> OTHER INFORMATION: Synthetic

<400> SEQUENCE: 19

His Ala Glu Gly Thr Phe Thr Ser Asp Val Ser Ser Asn Leu Glu Gly
1               5                   10                  15

Gln Ala Ala Lys Glu Phe Ile Ala Trp Leu Val Lys Gly Arg Gly
            20                  25                  30

<210> SEQ ID NO 20
<211> LENGTH: 30
<212> TYPE: PRT
<213> ORGANISM: artificial sequence
<220> FEATURE:
<223> OTHER INFORMATION: amino acid sequence of (a17)
<220> FEATURE:
<221> NAME/KEY: CARBOHYD
<222> LOCATION: (12)..(12)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 20

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Arg
            20                  25                  30

<210> SEQ ID NO 21
<211> LENGTH: 30
<212> TYPE: PRT
```

```
<213> ORGANISM: artificial sequence
<220> FEATURE:
<223> OTHER INFORMATION: amino acid sequence of (a18)
<220> FEATURE:
<221> NAME/KEY: CARBOHYD
<222> LOCATION: (16)..(16)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 21

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg
            20                  25                  30

<210> SEQ ID NO 22
<211> LENGTH: 30
<212> TYPE: PRT
<213> ORGANISM: artificial sequence
<220> FEATURE:
<223> OTHER INFORMATION: amino acid sequence of (a19)
<220> FEATURE:
<221> NAME/KEY: CARBOHYD
<222> LOCATION: (20)..(20)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 22

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Lys Gly Arg
            20                  25                  30

<210> SEQ ID NO 23
<211> LENGTH: 30
<212> TYPE: PRT
<213> ORGANISM: artificial sequence
<220> FEATURE:
<223> OTHER INFORMATION: amino acid sequence of (a20)
<220> FEATURE:
<221> NAME/KEY: CARBOHYD
<222> LOCATION: (24)..(24)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 23

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg
            20                  25                  30

<210> SEQ ID NO 24
<211> LENGTH: 30
<212> TYPE: PRT
<213> ORGANISM: artificial sequence
<220> FEATURE:
<223> OTHER INFORMATION: amino acid sequence of (a21)
<220> FEATURE:
<221> NAME/KEY: CARBOHYD
<222> LOCATION: (28)..(28)
<223> OTHER INFORMATION: Synthetic
```

```
<220> FEATURE:
<221> NAME/KEY: MOD_RES
<222> LOCATION: (30)..(30)
<223> OTHER INFORMATION: AMIDATION

<400> SEQUENCE: 24

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg
            20                  25                  30

<210> SEQ ID NO 25
<211> LENGTH: 30
<212> TYPE: PRT
<213> ORGANISM: artificial sequence
<220> FEATURE:
<223> OTHER INFORMATION: amino acid sequence of (a22)
<220> FEATURE:
<221> NAME/KEY: CARBOHYD
<222> LOCATION: (30)..(30)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 25

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys
            20                  25                  30

<210> SEQ ID NO 26
<211> LENGTH: 30
<212> TYPE: PRT
<213> ORGANISM: artificial sequence
<220> FEATURE:
<223> OTHER INFORMATION: amino acid sequence of (a23)
<220> FEATURE:
<221> NAME/KEY: CARBOHYD
<222> LOCATION: (13)..(13)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 26

His Ala Glu Gly Thr Phe Thr Ser Asp Val Ser Ser Cys Leu Glu Gly
1               5                   10                  15

Gln Ala Ala Lys Glu Phe Ile Ala Trp Leu Val Lys Gly Arg
            20                  25                  30

<210> SEQ ID NO 27
<211> LENGTH: 30
<212> TYPE: PRT
<213> ORGANISM: artificial sequence
<220> FEATURE:
<223> OTHER INFORMATION: amino acid sequence of (a24)
<220> FEATURE:
<221> NAME/KEY: CARBOHYD
<222> LOCATION: (12)..(12)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 27
```

His Ala Glu Gly Thr Phe Thr Ser Asp Val Ser Asn Tyr Leu Glu Gly
1               5                   10                  15

Gln Ala Ala Lys Glu Phe Ile Ala Trp Leu Val Lys Gly Arg
            20                  25                  30

<210> SEQ ID NO 28
<211> LENGTH: 30
<212> TYPE: PRT
<213> ORGANISM: artificial sequence
<220> FEATURE:
<223> OTHER INFORMATION: amino acid sequence of (a25)
<220> FEATURE:
<221> NAME/KEY: CARBOHYD
<222> LOCATION: (16)..(16)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 28

His Ala Glu Gly Thr Phe Thr Ser Asp Val Ser Ser Tyr Leu Glu Asn
1               5                   10                  15

Gln Ala Ala Lys Glu Phe Ile Ala Trp Leu Val Lys Gly Arg
            20                  25                  30

<210> SEQ ID NO 29
<211> LENGTH: 30
<212> TYPE: PRT
<213> ORGANISM: artificial sequence
<220> FEATURE:
<223> OTHER INFORMATION: amino acid sequence of (a26)
<220> FEATURE:
<221> NAME/KEY: CARBOHYD
<222> LOCATION: (20)..(20)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 29

His Ala Glu Gly Thr Phe Thr Ser Asp Val Ser Ser Tyr Leu Glu Gly
1               5                   10                  15

Gln Ala Ala Asn Glu Phe Ile Ala Trp Leu Val Lys Gly Arg
            20                  25                  30

<210> SEQ ID NO 30
<211> LENGTH: 30
<212> TYPE: PRT
<213> ORGANISM: artificial sequence
<220> FEATURE:
<223> OTHER INFORMATION: amino acid sequence of (a27)
<220> FEATURE:
<221> NAME/KEY: CARBOHYD
<222> LOCATION: (24)..(24)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 30

His Ala Glu Gly Thr Phe Thr Ser Asp Val Ser Ser Tyr Leu Glu Gly
1               5                   10                  15

Gln Ala Ala Lys Glu Phe Ile Asn Trp Leu Val Lys Gly Arg
            20                  25                  30

```
<210> SEQ ID NO 31
<211> LENGTH: 30
<212> TYPE: PRT
<213> ORGANISM: artificial sequence
<220> FEATURE:
<223> OTHER INFORMATION: amino acid sequence of (a28)
<220> FEATURE:
<221> NAME/KEY: CARBOHYD
<222> LOCATION: (28)..(28)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 31

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Asn Gly Arg
            20                  25                  30

<210> SEQ ID NO 32
<211> LENGTH: 30
<212> TYPE: PRT
<213> ORGANISM: artificial sequence
<220> FEATURE:
<223> OTHER INFORMATION: amino acid sequence of (a29)
<220> FEATURE:
<221> NAME/KEY: CARBOHYD
<222> LOCATION: (30)..(30)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 32

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Asn
            20                  25                  30

<210> SEQ ID NO 33
<211> LENGTH: 30
<212> TYPE: PRT
<213> ORGANISM: artificial sequence
<220> FEATURE:
<223> OTHER INFORMATION: amino acid sequence of (a30)
<220> FEATURE:
<221> NAME/KEY: CARBOHYD
<222> LOCATION: (13)..(13)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 33

His Ala Glu Gly Thr Phe Thr Ser Asp Val Ser Ser Asn Leu Glu Gly
1               5                   10                  15
Gln Ala Ala Lys Glu Phe Ile Ala Trp Leu Val Lys Gly Arg
            20                  25                  30

<210> SEQ ID NO 34
<211> LENGTH: 31
<212> TYPE: PRT
<213> ORGANISM: artificial sequence
<220> FEATURE:
<223> OTHER INFORMATION: amino acid sequence of (a31)
<220> FEATURE:
```

```
<221> NAME/KEY: CARBOHYD
<222> LOCATION: (20)..(20)
<223> OTHER INFORMATION: Synthetic

<400> SEQUENCE: 34

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 35
<211> LENGTH: 31
<212> TYPE: PRT
<213> ORGANISM: artificial sequence
<220> FEATURE:
<223> OTHER INFORMATION: amino acid sequence of (a32)
<220> FEATURE:
<221> NAME/KEY: CARBOHYD
<222> LOCATION: (28)..(28)
<223> OTHER INFORMATION: Synthetic

<400> SEQUENCE: 35

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 36
<211> LENGTH: 31
<212> TYPE: PRT
<213> ORGANISM: artificial sequence
<220> FEATURE:
<223> OTHER INFORMATION: amino acid sequence of (a33)
<220> FEATURE:
<221> NAME/KEY: CARBOHYD
<222> LOCATION: (12)..(12)
<223> OTHER INFORMATION: Synthetic
<220> FEATURE:
<221> NAME/KEY: CARBOHYD
<222> LOCATION: (30)..(30)
<223> OTHER INFORMATION: Synthetic

<400> SEQUENCE: 36

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 37
<211> LENGTH: 31
<212> TYPE: PRT
<213> ORGANISM: artificial sequence
<220> FEATURE:
<223> OTHER INFORMATION: amino acid sequence of (a34)
<220> FEATURE:
<221> NAME/KEY: CARBOHYD
<222> LOCATION: (16)..(16)
<223> OTHER INFORMATION: Synthetic
<220> FEATURE:
<221> NAME/KEY: CARBOHYD
<222> LOCATION: (24)..(24)
<223> OTHER INFORMATION: Synthetic

<400> SEQUENCE: 37

His Ala Glu Gly Thr Phe Thr Ser Asp Val Ser Ser Tyr Leu Glu Cys
1               5                   10                  15

Gln Ala Ala Lys Glu Phe Ile Cys Trp Leu Val Lys Gly Arg Gly
            20                  25                  30
```

```
<210> SEQ ID NO 38
<211> LENGTH: 31
<212> TYPE: PRT
<213> ORGANISM: artificial sequence
<220> FEATURE:
<223> OTHER INFORMATION: amino acid sequence of (a35)
<220> FEATURE:
<221> NAME/KEY: CARBOHYD
<222> LOCATION: (16)..(16)
<223> OTHER INFORMATION: Synthetic
<220> FEATURE:
<221> NAME/KEY: CARBOHYD
<222> LOCATION: (30)..(30)
<223> OTHER INFORMATION: Synthetic

<400> SEQUENCE: 38

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Cys Gly
            20                  25                  30

<210> SEQ ID NO 39
<211> LENGTH: 31
<212> TYPE: PRT
<213> ORGANISM: artificial sequence
<220> FEATURE:
<223> OTHER INFORMATION: amino acid sequence of (a36)
<220> FEATURE:
<221> NAME/KEY: CARBOHYD
<222> LOCATION: (20)..(20)
<223> OTHER INFORMATION: Synthetic
<220> FEATURE:
<221> NAME/KEY: CARBOHYD
<222> LOCATION: (28)..(28)
<223> OTHER INFORMATION: Synthetic

<400> SEQUENCE: 39

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Cys Gly Arg Gly
            20                  25                  30

<210> SEQ ID NO 40
<211> LENGTH: 31
<212> TYPE: PRT
<213> ORGANISM: artificial sequence
<220> FEATURE:
<223> OTHER INFORMATION: amino acid sequence of (a37)
<220> FEATURE:
<221> NAME/KEY: CARBOHYD
<222> LOCATION: (24)..(24)
<223> OTHER INFORMATION: Synthetic
<220> FEATURE:
<221> NAME/KEY: CARBOHYD
<222> LOCATION: (30)..(30)
<223> OTHER INFORMATION: Synthetic

<400> SEQUENCE: 40

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Cys Gly
            20                  25                  30

<210> SEQ ID NO 41
<211> LENGTH: 31
<212> TYPE: PRT
<213> ORGANISM: artificial sequence
<220> FEATURE:
```

```
<223> OTHER INFORMATION: amino acid sequence of (a38)
<220> FEATURE:
<221> NAME/KEY: CARBOHYD
<222> LOCATION: (12)..(12)
<223> OTHER INFORMATION: Synthetic
<220> FEATURE:
<221> NAME/KEY: CARBOHYD
<222> LOCATION: (30)..(30)
<223> OTHER INFORMATION: Synthetic

<400> SEQUENCE: 41

His Ala Glu Gly Thr Phe Thr Ser Asp Val Ser Asn Tyr Leu Glu Gly
1               5                   10                  15

Gln Ala Ala Lys Glu Phe Ile Ala Trp Leu Val Lys Gly Asn Gly
            20                  25                  30

<210> SEQ ID NO 42
<211> LENGTH: 31
<212> TYPE: PRT
<213> ORGANISM: artificial sequence
<220> FEATURE:
<223> OTHER INFORMATION: amino acid sequence of (a39)
<220> FEATURE:
<221> NAME/KEY: CARBOHYD
<222> LOCATION: (16)..(16)
<223> OTHER INFORMATION: Synthetic
<220> FEATURE:
<221> NAME/KEY: CARBOHYD
<222> LOCATION: (24)..(24)
<223> OTHER INFORMATION: Synthetic

<400> SEQUENCE: 42

His Ala Glu Gly Thr Phe Thr Ser Asp Val Ser Ser Tyr Leu Glu Asn
1               5                   10                  15

Gln Ala Ala Lys Glu Phe Ile Asn Trp Leu Val Lys Gly Arg Gly
            20                  25                  30

<210> SEQ ID NO 43
<211> LENGTH: 31
<212> TYPE: PRT
<213> ORGANISM: artificial sequence
<220> FEATURE:
<223> OTHER INFORMATION: amino acid sequence of (a40)
<220> FEATURE:
<221> NAME/KEY: CARBOHYD
<222> LOCATION: (16)..(16)
<223> OTHER INFORMATION: Synthetic
<220> FEATURE:
<221> NAME/KEY: CARBOHYD
<222> LOCATION: (30)..(30)
<223> OTHER INFORMATION: Synthetic

<400> SEQUENCE: 43

His Ala Glu Gly Thr Phe Thr Ser Asp Val Ser Ser Tyr Leu Glu Asn
1               5                   10                  15

Gln Ala Ala Lys Glu Phe Ile Ala Trp Leu Val Lys Gly Asn Gly
            20                  25                  30

<210> SEQ ID NO 44
<211> LENGTH: 31
<212> TYPE: PRT
<213> ORGANISM: artificial sequence
<220> FEATURE:
<223> OTHER INFORMATION: amino acid sequence of (a41)
<220> FEATURE:
<221> NAME/KEY: CARBOHYD
<222> LOCATION: (20)..(20)
<223> OTHER INFORMATION: Synthetic
<220> FEATURE:
<221> NAME/KEY: CARBOHYD
```

<222> LOCATION: (28)..(28)
<223> OTHER INFORMATION: Synthetic

<400> SEQUENCE: 44

His Ala Glu Gly Thr Phe Thr Ser Asp Val Ser Ser Tyr Leu Glu Gly
1               5                   10                  15

Gln Ala Ala Asn Glu Phe Ile Ala Trp Leu Val Asn Gly Arg Gly
            20                  25                  30

<210> SEQ ID NO 45
<211> LENGTH: 31
<212> TYPE: PRT
<213> ORGANISM: artificial sequence
<220> FEATURE:
<223> OTHER INFORMATION: amino acid sequence of (a42)
<220> FEATURE:
<221> NAME/KEY: CARBOHYD
<222> LOCATION: (24)..(24)
<223> OTHER INFORMATION: Synthetic
<220> FEATURE:
<221> NAME/KEY: CARBOHYD
<222> LOCATION: (30)..(30)
<223> OTHER INFORMATION: Synthetic

<400> SEQUENCE: 45

His Ala Glu Gly Thr Phe Thr Ser Asp Val Ser Ser Tyr Leu Glu Gly
1               5                   10                  15

Gln Ala Ala Lys Glu Phe Ile Asn Trp Leu Val Lys Gly Asn Gly
            20                  25                  30

<210> SEQ ID NO 46
<211> LENGTH: 32
<212> TYPE: PRT
<213> ORGANISM: artificial sequence
<220> FEATURE:
<223> OTHER INFORMATION: amino acid sequence of (a43)
<220> FEATURE:
<221> NAME/KEY: CARBOHYD
<222> LOCATION: (12)..(12)
<223> OTHER INFORMATION: Synthetic
<220> FEATURE:
<221> NAME/KEY: CARBOHYD
<222> LOCATION: (16)..(16)
<223> OTHER INFORMATION: Synthetic
<220> FEATURE:
<221> NAME/KEY: CARBOHYD
<222> LOCATION: (32)..(32)
<223> OTHER INFORMATION: Synthetic

<400> SEQUENCE: 46

His Ala Glu Gly Thr Phe Thr Ser Asp Val Ser Cys Tyr Leu Glu Cys
1               5                   10                  15

Gln Ala Ala Lys Glu Phe Ile Ala Trp Leu Val Lys Gly Arg Gly Cys
            20                  25                  30

<210> SEQ ID NO 47
<211> LENGTH: 31
<212> TYPE: PRT
<213> ORGANISM: artificial sequence
<220> FEATURE:
<223> OTHER INFORMATION: amino acid sequence of (a44)
<220> FEATURE:
<221> NAME/KEY: CARBOHYD
<222> LOCATION: (12)..(12)
<223> OTHER INFORMATION: Synthetic
<220> FEATURE:
<221> NAME/KEY: CARBOHYD
<222> LOCATION: (16)..(16)
<223> OTHER INFORMATION: Synthetic
<220> FEATURE:

```
<221> NAME/KEY: CARBOHYD
<222> LOCATION: (20)..(20)
<223> OTHER INFORMATION: Synthetic

<400> SEQUENCE: 47

His Ala Glu Gly Thr Phe Thr Ser Asp Val Ser Cys Tyr Leu Glu Cys
1               5                   10                  15

Gln Ala Ala Cys Glu Phe Ile Ala Trp Leu Val Lys Gly Arg Gly
            20                  25                  30

<210> SEQ ID NO 48
<211> LENGTH: 32
<212> TYPE: PRT
<213> ORGANISM: artificial sequence
<220> FEATURE:
<223> OTHER INFORMATION: amino acid sequence of (a45)
<220> FEATURE:
<221> NAME/KEY: CARBOHYD
<222> LOCATION: (20)..(20)
<223> OTHER INFORMATION: Synthetic
<220> FEATURE:
<221> NAME/KEY: CARBOHYD
<222> LOCATION: (30)..(30)
<223> OTHER INFORMATION: Synthetic
<220> FEATURE:
<221> NAME/KEY: CARBOHYD
<222> LOCATION: (32)..(32)
<223> OTHER INFORMATION: Synthetic

<400> SEQUENCE: 48

His Ala Glu Gly Thr Phe Thr Ser Asp Val Ser Ser Tyr Leu Glu Gly
1               5                   10                  15

Gln Ala Ala Asn Glu Phe Ile Ala Trp Leu Val Lys Gly Asn Gly Asn
            20                  25                  30

<210> SEQ ID NO 49
<211> LENGTH: 30
<212> TYPE: PRT
<213> ORGANISM: artificial sequence
<220> FEATURE:
<223> OTHER INFORMATION: amino acid sequence of (a46)
<220> FEATURE:
<221> NAME/KEY: CARBOHYD
<222> LOCATION: (12)..(12)
<223> OTHER INFORMATION: Synthetic
<220> FEATURE:
<221> NAME/KEY: CARBOHYD
<222> LOCATION: (16)..(16)
<223> OTHER INFORMATION: Synthetic
<220> FEATURE:
<221> NAME/KEY: CARBOHYD
<222> LOCATION: (20)..(20)
<223> OTHER INFORMATION: Synthetic
<220> FEATURE:
<221> NAME/KEY: MOD_RES
<222> LOCATION: (30)..(30)
<223> OTHER INFORMATION: AMIDATION

<400> SEQUENCE: 49

His Ala Glu Gly Thr Phe Thr Ser Asp Val Ser Asn Tyr Leu Glu Asn
1               5                   10                  15

Gln Ala Ala Asn Glu Phe Ile Ala Trp Leu Val Lys Gly Arg
            20                  25                  30

<210> SEQ ID NO 50
<211> LENGTH: 39
<212> TYPE: PRT
<213> ORGANISM: Heloderma
<220> FEATURE:
<223> OTHER INFORMATION: Exendin-4
```

```
<220> FEATURE:
<221> NAME/KEY: MOD_RES
<222> LOCATION: (39)..(39)
<223> OTHER INFORMATION: AMIDATION

<400> SEQUENCE: 50

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: artificial sequence
<220> FEATURE:
<223> OTHER INFORMATION: glycosylated Exendin-4
<220> FEATURE:
<221> NAME/KEY: MISC_FEATURE
<222> LOCATION: (12)..(12)
<223> OTHER INFORMATION: Xaa12: Lys, glycosylated Cys or glycosylated
      Asn
<220> FEATURE:
<221> NAME/KEY: MISC_FEATURE
<222> LOCATION: (14)..(14)
<223> OTHER INFORMATION: Xaa14: Met, glycosylated Cys or glycosylated
      Asn
<220> FEATURE:
<221> NAME/KEY: MISC_FEATURE
<222> LOCATION: (16)..(16)
<223> OTHER INFORMATION: Xaa16: Glu, glycosylated Cys or glycosylated
      Asn
<220> FEATURE:
<221> NAME/KEY: MISC_FEATURE
<222> LOCATION: (20)..(20)
<223> OTHER INFORMATION: Xaa20: Arg, glycosylated Cys or glycosylated
      Asn
<220> FEATURE:
<221> NAME/KEY: MISC_FEATURE
<222> LOCATION: (24)..(24)
<223> OTHER INFORMATION: Xaa24: Glu, glycosylated Cys or glycosylated
      Asn
<220> FEATURE:
<221> NAME/KEY: MISC_FEATURE
<222> LOCATION: (28)..(28)
<223> OTHER INFORMATION: Xaa28: Asn, glycosylated Cys or glycosylated
      Asn
<220> FEATURE:
<221> NAME/KEY: MISC_FEATURE
<222> LOCATION: (30)..(30)
<223> OTHER INFORMATION: Xaa30: Gly, glycosylated Cys or glycosylated
      Asn
<220> FEATURE:
<221> NAME/KEY: MOD_RES
<222> LOCATION: (39)..(39)
<223> OTHER INFORMATION: AMIDATION
<220> FEATURE:
<223> OTHER INFORMATION: At least one of Xaa12, Xaa14, Xaa16, Xaa20,
      Xaa24, Xaa28 and Xaa30 is glycosylated Cys or glycosylated Asn.

<400> SEQUENCE: 51

His Gly Glu Gly Thr Phe Thr Ser Asp Leu Ser Xaa Gln Xaa Glu Xaa
1               5                   10                  15

Glu Ala Val Xaa Leu Phe Ile Xaa Trp Leu Lys Xaa Gly Xaa Pro Ser
            20                  25                  30

Ser Gly Ala Pro Pro Pro Ser
        35

<210> SEQ ID NO 52
```

```
<211> LENGTH: 30
<212> TYPE: PRT
<213> ORGANISM: artificial sequence
<220> FEATURE:
<223> OTHER INFORMATION: BIM51077
<220> FEATURE:
<221> NAME/KEY: MISC_FEATURE
<222> LOCATION: (2)..(2)
<223> OTHER INFORMATION: Xaa8: Aib
<220> FEATURE:
<221> NAME/KEY: MISC_FEATURE
<222> LOCATION: (29)..(29)
<223> OTHER INFORMATION: Xaa35: Aib
<220> FEATURE:
<221> NAME/KEY: MOD_RES
<222> LOCATION: (30)..(30)
<223> OTHER INFORMATION: AMIDATION

<400> SEQUENCE: 52

His Xaa Glu Gly Thr Phe Thr Ser Asp Val Ser Ser Tyr Leu Glu Gly
1               5                   10                  15
Gln Ala Ala Lys Glu Phe Ile Ala Trp Leu Val Lys Xaa Arg
            20                  25                  30

<210> SEQ ID NO 53
<211> LENGTH: 30
<212> TYPE: PRT
<213> ORGANISM: artificial sequence
<220> FEATURE:
<223> OTHER INFORMATION: glycosylated BIM51077
<220> FEATURE:
<221> NAME/KEY: MISC_FEATURE
<222> LOCATION: (2)..(2)
<223> OTHER INFORMATION: Xaa8: Aib
<220> FEATURE:
<221> NAME/KEY: MISC_FEATURE
<222> LOCATION: (12)..(12)
<223> OTHER INFORMATION: Xaa18: Ser, glycosylated Cys or glycosylated
      Asn
<220> FEATURE:
<221> NAME/KEY: MISC_FEATURE
<222> LOCATION: (14)..(14)
<223> OTHER INFORMATION: Xaa20: Leu, glycosylated Cys or glycosylated
      Asn
<220> FEATURE:
<221> NAME/KEY: MISC_FEATURE
<222> LOCATION: (16)..(16)
<223> OTHER INFORMATION: Xaa22: Gly, glycosylated Cys or glycosylated
      Asn
<220> FEATURE:
<221> NAME/KEY: MISC_FEATURE
<222> LOCATION: (20)..(20)
<223> OTHER INFORMATION: Xaa26: Lys, glycosylated Cys or glycosylated
      Asn
<220> FEATURE:
<221> NAME/KEY: MISC_FEATURE
<222> LOCATION: (24)..(24)
<223> OTHER INFORMATION: Xaa30: Ala, glycosylated Cys or glycosylated
      Asn
<220> FEATURE:
<221> NAME/KEY: MISC_FEATURE
<222> LOCATION: (28)..(28)
<223> OTHER INFORMATION: Xaa34: Lys, glycosylated Cys or glycosylated
      Asn
<220> FEATURE:
<221> NAME/KEY: MISC_FEATURE
<222> LOCATION: (29)..(29)
<223> OTHER INFORMATION: Xaa35: Aib
<220> FEATURE:
<221> NAME/KEY: MISC_FEATURE
<222> LOCATION: (30)..(30)
<223> OTHER INFORMATION: Xaa36: Arg, glycosylated Cys or glycosylated
      Asn
<220> FEATURE:
<221> NAME/KEY: MOD_RES
<222> LOCATION: (30)..(30)
```

```
<223> OTHER INFORMATION: AMIDATION
<220> FEATURE:
<223> OTHER INFORMATION: At least one of Xaa18, Xaa20, Xaa22, Xaa26,
      Xaa30, Xaa34 and Xaa36 is glycosylated Cys or glycosylated Asn.

<400> SEQUENCE: 53

His Xaa Glu Gly Thr Phe Thr Ser Asp Val Ser Xaa Tyr Xaa Glu Xaa
1               5                   10                  15

Gln Ala Ala Xaa Glu Phe Ile Xaa Trp Leu Val Xaa Xaa Xaa
            20                  25                  30

<210> SEQ ID NO 54
<211> LENGTH: 31
<212> TYPE: PRT
<213> ORGANISM: artificial sequence
<220> FEATURE:
<223> OTHER INFORMATION: amino acid sequence of (b1) (Example 1)
<220> FEATURE:
<221> NAME/KEY: CARBOHYD
<222> LOCATION: (20)..(20)
<223> OTHER INFORMATION: Cys glycosylated by disialo oligosaccharide
<220> FEATURE:
<221> NAME/KEY: CARBOHYD
<222> LOCATION: (28)..(28)
<223> OTHER INFORMATION: Cys glycosylated by disialo oligosaccharide

<400> SEQUENCE: 54

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Cys Gly Arg Gly
            20                  25                  30

<210> SEQ ID NO 55
<211> LENGTH: 31
<212> TYPE: PRT
<213> ORGANISM: artificial sequence
<220> FEATURE:
<223> OTHER INFORMATION: amino acid sequence of (b2) (Example 2)
<220> FEATURE:
<221> NAME/KEY: CARBOHYD
<222> LOCATION: (12)..(12)
<223> OTHER INFORMATION: Cys glycosylated by disialo oligosaccharide
<220> FEATURE:
<221> NAME/KEY: CARBOHYD
<222> LOCATION: (30)..(30)
<223> OTHER INFORMATION: Cys glycosylated by disialo oligosaccharide

<400> SEQUENCE: 55

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 56
<211> LENGTH: 31
<212> TYPE: PRT
<213> ORGANISM: artificial sequence
<220> FEATURE:
<223> OTHER INFORMATION: amino acid sequence of (b3) (Example 3)
<220> FEATURE:
<221> NAME/KEY: CARBOHYD
<222> LOCATION: (16)..(16)
<223> OTHER INFORMATION: Cys glycosylated by disialo oligosaccharide
<220> FEATURE:
<221> NAME/KEY: CARBOHYD
<222> LOCATION: (24)..(24)
<223> OTHER INFORMATION: Cys glycosylated by disialo oligosaccharide

<400> SEQUENCE: 56
```

His Ala Glu Gly Thr Phe Thr Ser Asp Val Ser Ser Tyr Leu Glu Cys
1               5                   10                  15

Gln Ala Ala Lys Glu Phe Ile Cys Trp Leu Val Lys Gly Arg Gly
            20                  25                  30

<210> SEQ ID NO 57
<211> LENGTH: 31
<212> TYPE: PRT
<213> ORGANISM: artificial sequence
<220> FEATURE:
<223> OTHER INFORMATION: amino acid sequence of (b4) (Example 4)
<220> FEATURE:
<221> NAME/KEY: CARBOHYD
<222> LOCATION: (16)..(16)
<223> OTHER INFORMATION: Cys glycosylated by disialo oligosaccharide
<220> FEATURE:
<221> NAME/KEY: CARBOHYD
<222> LOCATION: (30)..(30)
<223> OTHER INFORMATION: Cys glycosylated by disialo oligosaccharide

<400> SEQUENCE: 57

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Cys Gly
            20                  25                  30

<210> SEQ ID NO 58
<211> LENGTH: 31
<212> TYPE: PRT
<213> ORGANISM: artificial sequence
<220> FEATURE:
<223> OTHER INFORMATION: amino acid sequence of (b5) (Example 5)
<220> FEATURE:
<221> NAME/KEY: CARBOHYD
<222> LOCATION: (24)..(24)
<223> OTHER INFORMATION: Cys glycosylated by disialo oligosaccharide
<220> FEATURE:
<221> NAME/KEY: CARBOHYD
<222> LOCATION: (30)..(30)
<223> OTHER INFORMATION: Cys glycosylated by disialo oligosaccharide

<400> SEQUENCE: 58

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Cys Gly
            20                  25                  30

<210> SEQ ID NO 59
<211> LENGTH: 31
<212> TYPE: PRT
<213> ORGANISM: artificial sequence
<220> FEATURE:
<223> OTHER INFORMATION: amino acid sequence of (b6) (Example 6)
<220> FEATURE:
<221> NAME/KEY: CARBOHYD
<222> LOCATION: (24)..(24)
<223> OTHER INFORMATION: Cys glycosylated by hyaluronan tetra
      saccharides

<400> SEQUENCE: 59

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 60
<211> LENGTH: 31
<212> TYPE: PRT

```
<213> ORGANISM: artificial sequence
<220> FEATURE:
<223> OTHER INFORMATION: amino acid sequence of (b7) (Example 7)
<220> FEATURE:
<221> NAME/KEY: CARBOHYD
<222> LOCATION: (24)..(24)
<223> OTHER INFORMATION: Cys glycosylated by hyaluronan octa saccharides

<400> SEQUENCE: 60

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 61
<211> LENGTH: 31
<212> TYPE: PRT
<213> ORGANISM: artificial sequence
<220> FEATURE:
<223> OTHER INFORMATION: amino acid sequence of (b8) (Example 8)
<220> FEATURE:
<221> NAME/KEY: CARBOHYD
<222> LOCATION: (30)..(30)
<223> OTHER INFORMATION: Cys glycosylated by hyaluronan tetra
      saccharides

<400> SEQUENCE: 61

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 62
<211> LENGTH: 31
<212> TYPE: PRT
<213> ORGANISM: artificial sequence
<220> FEATURE:
<223> OTHER INFORMATION: amino acid sequence of (b9) (Example 9)
<220> FEATURE:
<221> NAME/KEY: CARBOHYD
<222> LOCATION: (30)..(30)
<223> OTHER INFORMATION: Cys glycosylated by hyaluronan octa saccharides

<400> SEQUENCE: 62

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 63
<211> LENGTH: 31
<212> TYPE: PRT
<213> ORGANISM: artificial sequence
<220> FEATURE:
<223> OTHER INFORMATION: amino acid sequence of (b10) (Example 10)
<220> FEATURE:
<221> NAME/KEY: CARBOHYD
<222> LOCATION: (24)..(24)
<223> OTHER INFORMATION: Cys glycosylated by hyaluronan hexa-deca
      saccharides

<400> SEQUENCE: 63

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30
```

```
<210> SEQ ID NO 64
<211> LENGTH: 31
<212> TYPE: PRT
<213> ORGANISM: artificial sequence
<220> FEATURE:
<223> OTHER INFORMATION: amino acid sequence of (b11) (Example 11)
<220> FEATURE:
<221> NAME/KEY: CARBOHYD
<222> LOCATION: (30)..(30)
<223> OTHER INFORMATION: Cys glycosylated by hyaluronan hexa-deca
      saccharides

<400> SEQUENCE: 64

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 65
<211> LENGTH: 31
<212> TYPE: PRT
<213> ORGANISM: artificial sequence
<220> FEATURE:
<223> OTHER INFORMATION: amino acid sequence of (b12) (Example 12)
<220> FEATURE:
<221> NAME/KEY: CARBOHYD
<222> LOCATION: (30)..(30)
<223> OTHER INFORMATION: Cys glycosylated by high mannose-type
      heptaoligosaccharide

<400> SEQUENCE: 65

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 66
<211> LENGTH: 31
<212> TYPE: PRT
<213> ORGANISM: artificial sequence
<220> FEATURE:
<223> OTHER INFORMATION: amino acid sequence of (b13) (Example 13)
<220> FEATURE:
<221> NAME/KEY: CARBOHYD
<222> LOCATION: (20)..(20)
<223> OTHER INFORMATION: Lys glycosylated by asialo oligosaccharide

<400> SEQUENCE: 66

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 67
<211> LENGTH: 39
<212> TYPE: PRT
<213> ORGANISM: artificial sequence
<220> FEATURE:
<223> OTHER INFORMATION: amino acid sequence of (b14) (Example 14)
<220> FEATURE:
<221> NAME/KEY: CARBOHYD
<222> LOCATION: (30)..(30)
<223> OTHER INFORMATION: Cys glycosylated by disialo oligosaccharide
<220> FEATURE:
<221> NAME/KEY: MOD_RES
<222> LOCATION: (39)..(39)
<223> OTHER INFORMATION: AMIDATION

<400> SEQUENCE: 67
```

-continued

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Cys Pro Ser
            20                  25                  30

Ser Gly Ala Pro Pro Ser
        35

<210> SEQ ID NO 68
<211> LENGTH: 30
<212> TYPE: PRT
<213> ORGANISM: artificial sequence
<220> FEATURE:
<223> OTHER INFORMATION: amino acid sequence of (b15) (Example 15)
<220> FEATURE:
<221> NAME/KEY: MISC_FEATURE
<222> LOCATION: (2)..(2)
<223> OTHER INFORMATION: Aib
<220> FEATURE:
<221> NAME/KEY: CARBOHYD
<222> LOCATION: (20)..(20)
<223> OTHER INFORMATION: Cys glycosylated by disialo oligosaccharide
<220> FEATURE:
<221> NAME/KEY: MISC_FEATURE
<222> LOCATION: (29)..(29)
<223> OTHER INFORMATION: Aib
<220> FEATURE:
<221> NAME/KEY: MOD_RES
<222> LOCATION: (30)..(30)
<223> OTHER INFORMATION: AMIDATION

<400> SEQUENCE: 68

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Lys Xaa Arg
            20                  25                  30

<210> SEQ ID NO 69
<211> LENGTH: 31
<212> TYPE: PRT
<213> ORGANISM: artificial sequence
<220> FEATURE:
<223> OTHER INFORMATION: amino acid sequence having blocking groups
      (Example 1)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
```

```
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Cys having blocking group Trt
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Cys having blocking group Trt
<220> FEATURE:
<221> NAME/KEY: MISC_FEATURE
<222> LOCATION: (30)..(30)
<223> OTHER INFORMATION: Arg having blocking group Pbf

<400> SEQUENCE: 69

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Cys Gly Arg Gly
            20                  25                  30

<210> SEQ ID NO 70
<211> LENGTH: 31
<212> TYPE: PRT
<213> ORGANISM: artificial sequence
<220> FEATURE:
<223> OTHER INFORMATION: amino acid sequence having blocking groups
      (Example 2)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
```

```
<220> FEATURE:
<221> NAME/KEY: MISC_FEATURE
<222> LOCATION: (12)..(12)
<223> OTHER INFORMATION: Cys having blocking group Trt
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Cys having blocking group Trt

<400> SEQUENCE: 70

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 71
<211> LENGTH: 31
<212> TYPE: PRT
<213> ORGANISM: artificial sequence
<220> FEATURE:
<223> OTHER INFORMATION: amino acid sequence having blocking groups
      (Example 3)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
```

```
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (16)..(16)
<223> OTHER INFORMATION: Cys having blocking group Trt
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (24)..(24)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 71

His Ala Glu Gly Thr Phe Thr Ser Asp Val Ser Ser Tyr Leu Glu Cys
1               5                   10                  15

Gln Ala Ala Lys Glu Phe Ile Cys Trp Leu Val Lys Gly Arg Gly
            20                  25                  30

<210> SEQ ID NO 72
<211> LENGTH: 31
<212> TYPE: PRT
<213> ORGANISM: artificial sequence
<220> FEATURE:
<223> OTHER INFORMATION: amino acid sequence having blocking groups
      (Example 4)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
```

```
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (16)..(16)
<223> OTHER INFORMATION: Cys having blocking group Trt
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Cys having blocking group Trt

<400> SEQUENCE: 72

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Cys Gly
            20                  25                  30

<210> SEQ ID NO 73
<211> LENGTH: 31
<212> TYPE: PRT
<213> ORGANISM: artificial sequence
<220> FEATURE:
<223> OTHER INFORMATION: amino acid sequence having blocking groups
      (Example 5)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
```

<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (24)..(24)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Cys having blocking group Trt

<400> SEQUENCE: 73

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Cys Gly
            20                  25                  30

<210> SEQ ID NO 74
<211> LENGTH: 31
<212> TYPE: PRT
<213> ORGANISM: artificial sequence
<220> FEATURE:
<223> OTHER INFORMATION: amino acid sequence having blocking groups
      (Comparative Example 1)
<220> FEATURE:
<221> NAME/KEY: MISC_FEATURE
<222> LOCATION: (1)..(1)
<223> OTHER INFORMATION: His having blocking group Trt

```
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 74

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 75
<211> LENGTH: 31
<212> TYPE: PRT
<213> ORGANISM: artificial sequence
<220> FEATURE:
<223> OTHER INFORMATION: amino acid sequence having blocking groups
      (Synthetic Example 2)
<220> FEATURE:
<221> NAME/KEY: MISC_FEATURE
```

```
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (24)..(24)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 75

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 76
<211> LENGTH: 31
<212> TYPE: PRT
```

```
<213> ORGANISM: artificial sequence
<220> FEATURE:
<223> OTHER INFORMATION: amino acid sequence (Synthetic Example 2)

<400> SEQUENCE: 76

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 77
<211> LENGTH: 31
<212> TYPE: PRT
<213> ORGANISM: artificial sequence
<220> FEATURE:
<223> OTHER INFORMATION: amino acid sequence having blocking groups
      (Synthetic Example 3)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
```

```
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Cys having blocking group Trt

<400> SEQUENCE: 77

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 78
<211> LENGTH: 31
<212> TYPE: PRT
<213> ORGANISM: artificial sequence
<220> FEATURE:
<223> OTHER INFORMATION: amino acid sequence (Synthetic Example 3)

<400> SEQUENCE: 78

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 79
<211> LENGTH: 31
<212> TYPE: PRT
<213> ORGANISM: artificial sequence
<220> FEATURE:
<223> OTHER INFORMATION: amino acid sequence having blocking groups
      (Synthetic Example 4)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
```

```
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Arg having blocking group Pbf
<220> FEATURE:
<221> NAME/KEY: MISC_FEATURE
<222> LOCATION: (30)..(30)
<223> OTHER INFORMATION: Arg having blocking group Pbf

<400> SEQUENCE: 79

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Arg Gly Arg Gly
            20                  25                  30

<210> SEQ ID NO 80
<211> LENGTH: 31
<212> TYPE: PRT
<213> ORGANISM: artificial sequence
<220> FEATURE:
<223> OTHER INFORMATION: amino acid sequence (Synthetic Example 4)

<400> SEQUENCE: 80

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 81
<211> LENGTH: 39
<212> TYPE: PRT
<213> ORGANISM: artificial sequence
<220> FEATURE:
<223> OTHER INFORMATION: amino acid sequence having blocking groups
      (Synthetic Example 5)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
```

```
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Lys having blocking group Boc
<220> FEATURE:
<221> NAME/KEY: MISC_FEATURE
<222> LOCATION: (13)..(13)
<223> OTHER INFORMATION: Gln having blocking group Trt
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (16)..(16)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Glu having blocking group OtBu
<220> FEATURE:
<221> NAME/KEY: MISC_FEATURE
<222> LOCATION: (20)..(20)
<223> OTHER INFORMATION: Arg having blocking group Pbf
<220> FEATURE:
<221> NAME/KEY: MISC_FEATURE
<222> LOCATION: (24)..(24)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (27)..(27)
<223> OTHER INFORMATION: Lys having blocking group Boc
<220> FEATURE:
<221> NAME/KEY: MISC_FEATURE
<222> LOCATION: (28)..(28)
<223> OTHER INFORMATION: Asn having blocking group Trt
<220> FEATURE:
<221> NAME/KEY: MISC_FEATURE
<222> LOCATION: (30)..(30)
<223> OTHER INFORMATION: Cys having blocking group Trt
<220> FEATURE:
<221> NAME/KEY: MISC_FEATURE
<222> LOCATION: (32)..(32)
<223> OTHER INFORMATION: Ser having blocking group tBu
<220> FEATURE:
<221> NAME/KEY: MISC_FEATURE
<222> LOCATION: (33)..(33)
<223> OTHER INFORMATION: Ser having blocking group tBu
<220> FEATURE:
<221> NAME/KEY: MISC_FEATURE
<222> LOCATION: (39)..(39)
<223> OTHER INFORMATION: Ser having blocking group tBu
<220> FEATURE:
<221> NAME/KEY: MOD_RES
<222> LOCATION: (39)..(39)
<223> OTHER INFORMATION: AMIDATION

<400> SEQUENCE: 81

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Cys Pro Ser
            20                  25                  30

Ser Gly Ala Pro Pro Pro Ser
        35

<210> SEQ ID NO 82
```

```
<211> LENGTH: 39
<212> TYPE: PRT
<213> ORGANISM: artificial sequence
<220> FEATURE:
<223> OTHER INFORMATION: amino acid sequence (Synthetic Example 5)
<220> FEATURE:
<221> NAME/KEY: MOD_RES
<222> LOCATION: (39)..(39)
<223> OTHER INFORMATION: AMIDATION

<400> SEQUENCE: 82

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Cys Pro Ser
             20                  25                  30

Ser Gly Ala Pro Pro Pro Ser
                 35

<210> SEQ ID NO 83
<211> LENGTH: 30
<212> TYPE: PRT
<213> ORGANISM: artificial sequence
<220> FEATURE:
<223> OTHER INFORMATION: amino acid sequence having blocking groups
      (Synthetic Example 6)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (2)..(2)
<223> OTHER INFORMATION: Xaa8: Aib
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
```

```
<222> LOCATION: (20)..(20)
<223> OTHER INFORMATION: Cys having blocking group Trt
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (29)..(29)
<223> OTHER INFORMATION: Xaa35: Aib
<220> FEATURE:
<221> NAME/KEY: MISC_FEATURE
<222> LOCATION: (30)..(30)
<223> OTHER INFORMATION: Arg having blocking group Pbf
<220> FEATURE:
<221> NAME/KEY: MOD_RES
<222> LOCATION: (30)..(30)
<223> OTHER INFORMATION: AMIDATION

<400> SEQUENCE: 83

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Lys Xaa Arg
            20                  25                  30

<210> SEQ ID NO 84
<211> LENGTH: 30
<212> TYPE: PRT
<213> ORGANISM: artificial sequence
<220> FEATURE:
<223> OTHER INFORMATION: amino acid sequence (Synthetic Example 6)
<220> FEATURE:
<221> NAME/KEY: MISC_FEATURE
<222> LOCATION: (2)..(2)
<223> OTHER INFORMATION: Xaa8: Aib
<220> FEATURE:
<221> NAME/KEY: MISC_FEATURE
<222> LOCATION: (29)..(29)
<223> OTHER INFORMATION: Xaa35: Aib
<220> FEATURE:
<221> NAME/KEY: MOD_RES
<222> LOCATION: (30)..(30)
<223> OTHER INFORMATION: AMIDATION

<400> SEQUENCE: 84

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Lys Xaa Arg
            20                  25                  30
```

The invention claimed is:

1. An oligosaccharide chain added GLP-1 peptide having GLP-1 activity, wherein at least two amino acids are each substituted with an oligosaccharide chain added amino acid, wherein the GLP-1 peptide is:
   (a) GLP-1; or
   (b) a peptide having the amino acid sequence of GLP-1 with deletion, substitution or addition of 1-3 amino acids, wherein each of the substituted sites is selected from the group consisting of the positions 18, 20, 22, 26, 30, 34, and 36 of GLP-1, and wherein each of said oligosaccharide chains is independently a biantennary complex-type oligosaccharide chain and represented by the following formula:

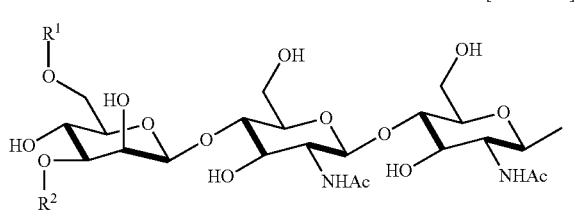

[Formula 1]

wherein
R$^1$ and R$^2$ are the same or different and each represents

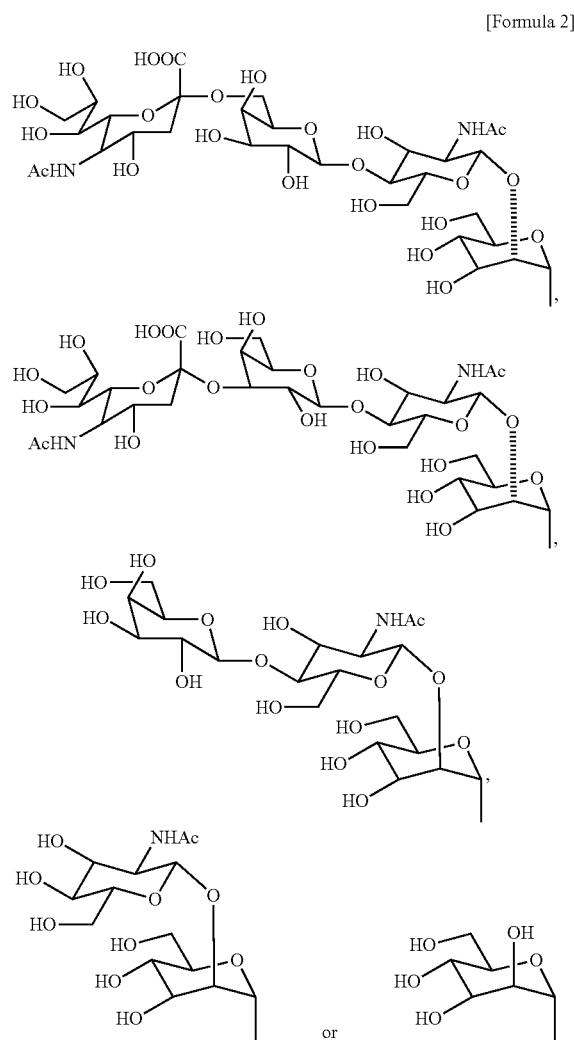

[Formula 2]

and Ac represents an acetyl group;
or a pharmaceutically acceptable salt thereof.

2. The oligosaccharide chain added GLP-1 peptide according to claim 1, wherein each of said oligosaccharide chain added amino acids is independently oligosaccharide chain added Asn and/or oligosaccharide chain added Cys.

3. The oligosaccharide chain added GLP-1 peptide according to claim 1, wherein in said oligosaccharide chain added amino acid, the oligosaccharide chain is linked to the amino acid without a linker.

4. The oligosaccharide chain added GLP-1 peptide according to claim 1, wherein said oligosaccharide chain is substantially uniform.

5. The oligosaccharide chain added GLP-1 peptide according to to claim 1, wherein:
   each of said oligosaccharide chain added amino acids is oligosaccharide chain added Asn;
      in said oligosaccharide chain added amino acid, the oligosaccharide chain is linked to the amino acid without a linker;
   said oligosaccharide chains each consist of four or more sugars;
   and
   said oligosaccharide chain is substantially uniform.

6. The oligosaccharide chain added GLP-1 peptide according to claim 1, having at least one of the following properties:
   a higher stability in blood than that of GLP-1;
   an activity of controlling blood-sugar levels at least 10 times that of GLP-1 in OGTT (Oral Glucose Tolerance Test); and
   DPP-IV resistance at least 30 times that of GLP-1.

7. A pharmaceutical composition comprising the oligosaccharide chain added GLP-1 peptide according to claim 1 as an active ingredient.

8. The pharmaceutical composition according to claim 7 for treating or preventing disease associated with GLP-1.

9. The pharmaceutical composition according to claim 8, wherein said disease associated with GLP-1 is diabetes.

10. A method for treating or preventing disease associated with GLP-1 comprising administering effective amount of the oligosaccharide chain added GLP-1 peptide according to claim 1.

11. An oligosaccharide chain added GLP-1 peptide having GLP-1 activity according to claim 1, wherein, in said oligosaccharide chain added amino acid, the oligosaccharide chain is linked to the amino acid via a linker, and said linker contains an amino acid at the terminal bound to said oligosaccharide chain.

12. The oligosaccharide chain added GLP-1 peptide according to claim 11, the amino acid bound to said linker is Lys.

13. The oligosaccharide chain added GLP-1 peptide according to claim 11, wherein the amino acid contained in said linker is Asn.

14. The oligosaccharide chain added GLP-1 peptide according to claim 11, wherein the oligosaccharide chain is substantially uniform.

15. A pharmaceutical composition comprising the oligosaccharide chain added GLP-1 peptide according to claim 11 as an active ingredient.

* * * * *